(12) United States Patent
Mardor et al.

(10) Patent No.: US 11,892,530 B2
(45) Date of Patent: *Feb. 6, 2024

(54) MAGNETIC RESONANCE MAPS FOR ANALYZING TISSUE

(71) Applicants: Tel HaShomer Medical Research Infrastructure and Services Ltd., Ramat-Gan (IL); Ramot at Tel-Aviv University Ltd., Tel-Aviv (IL)

(72) Inventors: Yael Mardor, Natania (IL); Leor Zach, Rehovot (IL); David Guez, Tel-Aviv (IL); David Last, Jerusalem (IL); Dianne Daniels Elmakias, Ramat-HaSharon (IL)

(73) Assignees: Tel HaShomer Medical Research Infrastructure and Services Ltd., Ramat-Gan (IL); Ramot at Tel-Aviv University Ltd., Tel-Aviv (IL)

( * ) Notice: Subject to any disclaimer, the term of this patent is extended or adjusted under 35 U.S.C. 154(b) by 659 days.

This patent is subject to a terminal disclaimer.

(21) Appl. No.: 16/992,163

(22) Filed: Aug. 13, 2020

(65) Prior Publication Data
US 2020/0371174 A1 Nov. 26, 2020

Related U.S. Application Data

(63) Continuation of application No. 14/787,040, filed as application No. PCT/IB2014/060981 on Apr. 24, 2014, now Pat. No. 10,809,323.
(Continued)

(51) Int. Cl.
*G01R 33/28* (2006.01)
*G01R 33/56* (2006.01)
(Continued)

(52) U.S. Cl.
CPC .......... *G01R 33/281* (2013.01); *A61B 5/0042* (2013.01); *A61B 5/055* (2013.01);
(Continued)

(58) Field of Classification Search
CPC ..... A61B 5/055; A61B 5/0042; A61B 5/4848; A61B 5/7275; G01R 33/281; G01R 33/4806; G01R 33/5601; G01R 33/5608
See application file for complete search history.

(56) References Cited

U.S. PATENT DOCUMENTS 4,439,451 A 3/1984 Coleman
4,801,575 A 1/1989 Pardridge
(Continued)

FOREIGN PATENT DOCUMENTS

JP 2010-526636 8/2010
WO WO 03/025606 3/2003
(Continued)

OTHER PUBLICATIONS

Advisory Action Before the Filing of an Appeal Brief Dated Jun. 18, 2013 From the US Patent and Trademark Office Re. U.S. Appl. No. 13/342,222.
(Continued)

*Primary Examiner* — Baisakhi Roy

(57) ABSTRACT

Apparatus for operating MRI is disclosed. The apparatus comprises: a control for operating an MRI scanner to carry out an MRI scan; an input for receiving first and second MRI scans respectively at the beginning and end of a predetermined time interval post contrast administration; a subtraction map former for forming a subtraction map from the first and the second MRI scans by analyzing the scans to distinguish between a population in which contrast clearance from the tissue is slower than contrast accumulation, and a population in which clearance is faster than accumulation;
(Continued)

and an output to provide an indication of distribution of the populations. The control is configured to carry out the first scan at least five minutes and no more than twenty minutes post contrast administration and to carry out the second scan such that the predetermined time period is at least twenty minutes.

**33 Claims, 35 Drawing Sheets
(29 of 35 Drawing Sheet(s) Filed in Color)**

Related U.S. Application Data

(60) Provisional application No. 61/815,343, filed on Apr. 24, 2013.

(51) Int. Cl.
| | | |
|---|---|---|
| *G01R 33/48* | (2006.01) | |
| *A61B 5/055* | (2006.01) | |
| *A61B 5/00* | (2006.01) | |
| *G06T 7/00* | (2017.01) | |
| *G16H 40/40* | (2018.01) | |
| *G16H 30/40* | (2018.01) | |
| *G16H 40/63* | (2018.01) | |
| *A61K 31/166* | (2006.01) | |
| *A61K 31/7068* | (2006.01) | |
| *A61K 31/555* | (2006.01) | |

(52) U.S. Cl.
CPC .......... *A61B 5/4842* (2013.01); *A61B 5/4848* (2013.01); *A61B 5/7275* (2013.01); *G01R 33/4806* (2013.01); *G01R 33/5601* (2013.01); *G01R 33/5608* (2013.01); *G06T 7/0016* (2013.01); *G16H 30/40* (2018.01); *G16H 40/40* (2018.01); *G16H 40/63* (2018.01); *A61B 2576/026* (2013.01); *A61K 31/166* (2013.01); *A61K 31/555* (2013.01); *A61K 31/7068* (2013.01); *A61K 2300/00* (2013.01); *G06T 2207/10096* (2013.01); *G06T 2207/30016* (2013.01); *G06T 2207/30096* (2013.01)

(56) References Cited

U.S. PATENT DOCUMENTS

| | | | |
|---|---|---|---|
| 5,004,697 A | 4/1991 | Pardridge | |
| 5,004,949 A | 4/1991 | Latassa et al. | |
| 5,059,415 A | 10/1991 | Neuwelt | |
| 5,186,924 A | 2/1993 | Fishman | |
| 5,213,788 A * | 5/1993 | Ranney | A61K 49/1845 424/617 |
| 5,260,050 A * | 11/1993 | Ranney | G01R 33/5601 424/617 |
| 5,266,480 A | 11/1993 | Naughton et al. | |
| 5,434,137 A | 7/1995 | Black | |
| 5,506,206 A | 4/1996 | Kozarich et al. | |
| 5,550,933 A | 8/1996 | Stetten | |
| 5,591,715 A | 1/1997 | Coon et al. | |
| 5,670,477 A | 9/1997 | Poduslo et al. | |
| 5,672,334 A * | 9/1997 | Ranney | C08B 37/0069 424/9.34 |
| 5,707,604 A * | 1/1998 | Ranney | C08B 37/0063 514/56 |
| 5,752,515 A | 5/1998 | Jolesz et al. | |
| 6,106,866 A * | 8/2000 | Ranney | A61K 49/12 424/548 |
| 6,294,520 B1 | 9/2001 | Naito | |
| 6,419,949 B1 | 7/2002 | Gasco | |
| 6,574,501 B2 | 6/2003 | Lambert et al. | |
| 6,703,381 B1 | 3/2004 | Ekwuribe et al. | |
| 10,275,680 B2 * | 4/2019 | Zach | G06T 7/0012 |
| 10,809,323 B2 * | 10/2020 | Mardor | G01R 33/4806 |
| 10,970,594 B2 * | 4/2021 | Zach | A61B 5/0042 |
| 2002/0026116 A1 | 2/2002 | Schmainda | |
| 2003/0050552 A1 | 3/2003 | Vu | |
| 2004/0052730 A1 * | 3/2004 | Hochman | G01N 33/5005 424/9.2 |
| 2004/0096395 A1 | 5/2004 | Xiong et al. | |
| 2004/0220644 A1 | 11/2004 | Shalev et al. | |
| 2005/0171423 A1 | 8/2005 | Ho et al. | |
| 2006/0052690 A1 | 3/2006 | Sirohey et al. | |
| 2006/0058624 A1 | 3/2006 | Kimura | |
| 2006/0183998 A1 | 8/2006 | Biglieri et al. | |
| 2006/0204443 A1 * | 9/2006 | Kobayashi | A61K 49/124 600/1 |
| 2006/0226836 A1 | 10/2006 | Shu et al. | |
| 2006/0245629 A1 | 11/2006 | Huo et al. | |
| 2007/0263769 A1 | 11/2007 | Roell | |
| 2008/0100612 A1 | 5/2008 | Dastmalchi et al. | |
| 2009/0232829 A1 * | 9/2009 | Xing | C07K 16/2863 514/44 R |
| 2009/0264734 A1 | 10/2009 | Degani et al. | |
| 2010/0106007 A1 | 4/2010 | Wacker et al. | |
| 2010/0142786 A1 * | 6/2010 | Degani | G06T 7/0012 382/128 |
| 2010/0172842 A1 * | 7/2010 | Israeli | A61B 5/4836 600/420 |
| 2010/0259263 A1 | 10/2010 | Holland et al. | |
| 2011/0150309 A1 * | 6/2011 | Barfett | G06T 7/33 382/131 |
| 2011/0152692 A1 | 6/2011 | Nie et al. | |
| 2012/0101365 A1 | 4/2012 | Israeli et al. | |
| 2013/0119985 A1 | 5/2013 | Lin et al. | |
| 2013/0274281 A1 | 10/2013 | Bradley | |
| 2014/0270451 A1 * | 9/2014 | Zach | A61B 5/055 382/131 |
| 2015/0265210 A1 | 9/2015 | Israeli et al. | |
| 2016/0008619 A1 | 1/2016 | Pell et al. | |
| 2016/0109539 A1 | 4/2016 | Mardor et al. | |
| 2019/0180139 A1 * | 6/2019 | Zach | A61B 5/055 |
| 2020/0371173 A1 | 11/2020 | Mardor et al. | |

FOREIGN PATENT DOCUMENTS

| | | |
|---|---|---|
| WO | WO 2006/035443 | 4/2006 |
| WO | WO 2007/035721 | 3/2007 |
| WO | WO 2008/139480 | 11/2008 |
| WO | WO 2012/011069 | 1/2012 |
| WO | WO 2013/057697 | 4/2013 |
| WO | WO 2014/174480 | 10/2014 |

OTHER PUBLICATIONS

Applicant-Initiated Interview Summary dated Aug. 2, 2018 From the US Patent and Trademark Office Re. U.S. Appl. No. 14/352,099. (3 pages).
Communication Pursuant to Article 94(3) EPC dated Feb. 5, 2016 From the European Patent Office Re. Application No. 08751361.0.
Communication Pursuant to Article 94(3) EPC dated Apr. 13, 2015 From the European Patent Office Re. Application No. 08751361.0.
Communication Pursuant to Article 94(3) EPC dated Feb. 18, 2020 From the European Patent Office Re. Application No. 12841602.1. (4 Pages).
Communication Pursuant to Article 94(3) EPC dated Jul. 20, 2018 From the European Patent Office Re. Application No. 14789048.7. (7 Pages).
Communication Pursuant to Article 94(3) EPC dated May 22, 2014 From the European Patent Office Re. Application No. 08751361.0.
Examination Report Under Sections 12 & 13 of the Patents Act, 1970 and the Patents Rules, 2003 dated Jul. 20, 2017 From the Government of India, Patent Office, Intellectual Property Building Re. Application No. 7341/CHENP/2009. (4 Pages).
Final Official Action dated Aug. 7, 2020 from the US Patent and Trademark Office Re. U.S. Appl. No. 16/280,089. (27 pages).
International Preliminary Report on Patentability dated May 1, 2014 From the International Bureau of WIPO Re. Application No. PCT/IB2012/055703.

(56) References Cited

OTHER PUBLICATIONS

International Preliminary Report on Patentability dated Nov. 5, 2015 From the International Bureau of WIPO Re. Application No. PCT/IB2014/060981.
International Preliminary Report on Patentability dated Nov. 26, 2009 From the International Bureau of WIPO Re. Application No. PCT/IL2008/000673.
International Search Report and the Written Opinion dated Sep. 10, 2014 From the International Searching Authority Re. Application No. PCT/IB2014/060981.
International Search Report and the Written Opinion dated Mar. 19, 2013 From the International Searching Authority Re. Application No. PCT/IB2012/055703.
International Search Report dated Jun. 3, 2009 From the International Searching Authority Re. Application No. PCT/IL2008/000673.
Invitation Pursuant to Rule 63(1) EPC dated May 22, 2014 From the European Patent Office Re. Application No. 12151382.4.
Notice of Allowance dated Nov. 20, 2018 From the US Patent and Trademark Office Re. U.S. Appl. No. 14/352,099. (21 pages).
Notification of Reasons for Rejection dated Jan. 30, 2018 From the Japan Patent Office Re. Application No. 2016-509589 and Its Translation Into English. (10 Pages).
Notification of Reasons for Rejection dated Oct. 30, 2018 From the Japan Patent Office Re. Application No. 2016-509589 and Its Translation Into English. (4 Pages).
Office Action dated Mar. 3, 2013 From the Israel Patent Office Re. Application No. 223743 and Its Translation Into English.
Office Action dated Feb. 13, 2013 From the Israel Patent Office Re. Application No. 217360 and Its Translation Into English.
Office Action dated May 13, 2018 From the Israel Patent Office Re. Application No. 232176 and Its Translation Into English. (4 Pages).
Office Action dated Feb. 19, 2012 From the Israel Patent Office Re. Application No. 202118 and Its Translation Into English.
Office Action dated Feb. 20, 2012 From the Israel Patent Office Re. Application No. 217360 and Its Translation Into English.
Official Action dated Jul. 1, 2016 From the US Patent and Trademark Office Re. U.S. Appl. No. 12/451,477.
Official Action dated Oct. 2, 2015 From the US Patent and Trademark Office Re. U.S. Appl. No. 12/451,477.
Official Action dated Dec. 4, 2019 From the US Patent and Trademark Office Re. U.S. Appl. No. 14/787,040. (10 pages).
Official Action dated Jun. 5, 2014 From the US Patent and Trademark Office Re. U.S. Appl. No. 13/342,222.
Official Action dated Apr. 6, 2018 From the US Patent and Trademark Office Re. U.S. Appl. No. 14/787,040. (43 pages).
Official Action dated Jan. 7, 2019 From the US Patent and Trademark Office Re. U.S. Appl. No. 14/787,040. (14 pages).
Official Action dated Aug. 8, 2017 From the US Patent and Trademark Office Re. U.S. Appl. No. 14/726,629. (52 pages).
Official Action dated Feb. 11, 2013 From the US Patent and Trademark Office Re. U.S. Appl. No. 12/451,477.
Official Action dated Jan. 14, 2016 From the US Patent and Trademark Office Re. U.S. Appl. No. 14/352,099.
Official Action dated Jun. 15, 2017 From the US Patent and Trademark Office Re. U.S. Appl. No. 14/352,099. (34 Pages).
Official Action dated Dec. 18, 2012 From the US Patent and Trademark Office Re. U.S. Appl. No. 13/342,222.
Official Action dated Dec. 18, 2014 From the US Patent and Trademark Office Re. U.S. Appl. No. 12/451,477.
Official Action dated Apr. 19, 2018 From the US Patent and Trademark Office Re. U.S. Appl. No. 14/352,099. (40 pages).
Official Action dated Dec. 20, 2013 From the US Patent and Trademark Office Re. U.S. Appl. No. 13/342,222.
Official Action dated Oct. 20, 2016 From the US Patent and Trademark Office Re. U.S. Appl. No. 14/352,099.
Official Action dated Apr. 23, 2012 From the US Patent and Trademark Office Re. U.S. Appl. No. 12/451,477.
Official Action dated Mar. 23, 2017 From the US Patent and Trademark Office Re. U.S. Appl. No. 12/451,477. (25 pages).
Official Action dated Jul. 25, 2012 From the US Patent and Trademark Office Re. U.S. Appl. No. 13/342,222.
Official Action dated Jun. 28, 2019 From the US Patent and Trademark Office Re. U.S. Appl. No. 14/787,040. (9 pages).
Official Action dated Dec. 30, 2014 From the US Patent and Trademark Office Re. U.S. Appl. No. 13/342,222.
Official Action dated Oct. 31, 2019 From the US Patent and Trademark Office Re. U.S. Appl. No. 16/280,089. (34 Pages).
Partial European Search Report and the European Search Opinion dated Oct. 7, 2014 From the European Patent Office Re. Application No. 12151382.4.
Restriction Official Action dated Apr. 13, 2012 From the US Patent and Trademark Office Re. U.S. Appl. No. 13/342,222.
Summons to Attend Oral Proceedings Pursuant to Rule 115(1) EPC dated Jul. 12, 2016 From the European Patent Office Re. Application No. 12151382.4.
Supplementary European Search Report and the European Search Opinion dated Dec. 19, 2016 From the European Patent Office Re. Application No. 14789048.7. (7 Pages).
Supplementary European Search Report and the European Search Opinion dated Apr. 23, 2015 From the European Patent Office Re. Application No. 12841602.1.
Translation of Notice of Reason for Rejection dated Apr. 19, 2013 From the Japanese Patent Office Re. Application No. 2010-508031.
Written Opinion dated Jun. 3, 2009 From the International Searching Authority Re. Application No. PCT/IL2008/000673.
Abbott et al. "Astrocyte-Endothelial Interactions at the Blood-Brain Barrier", Nature Reviews Neuroscience, 7: 41-53, 2006.
Aicher et al. "Contrast-Enhanced Magnetic Resonance Imaging of Tumor-Bearing Mice Treated With Human Recombinant Tumor Necrosis Factor Alpha", Cancer Research, 50: 7376-7381, Nov. 15, 1990. Abstract, Fig.1, p. 7377, col. 1, Para 4-p. 7379, col. 2, Para 3, Figs.1, 2.
Ballabh et al. "The Blood-Brain Barrier: An Overview Structure, Regulation, and Clinical Implications", Neurobiology of Disease, 16: 1-13, 2004.
Bennett et al. "Detection of Blood-Brain Barrier Disruption in Rat Brain After Osmotic Shock Using Manganese-Enhanced Magnetic Resonance Imaging (MEMRI)", Proceedings of the International Society for Magnetic Resonance in Medicine, 14: 2324, May 6, 2006.
Blanchette et al. "Real Time Monitoring of Hyperosmolar Blood Brain Barrier Disruption Using MRI", Proceedings of the International Society for Magnetic Resonance in Medicine, 14: 998, May 6, 2006.
Choi et al. "New subtraction Algorithms for Evaluation of Lesions on Dynamic Contrast-Enhanced MR Mammography", European Radiology1,12: 3018-3022, Dec. 18, 2002.
Choi et al. "Three-Phase Dynamic Breast Magnetic Resonance Imaging With Two-Way Subtraction", Journal of Computer Assisted Tomography, 29(6): 834-841, Nov./Dec. 2005.
Ding et al. "Contrast-Enhanced Subtraction Harmonic Sonography for Evaluating Treatment Response in Patients With Hepatocellular Carcinoma", American Journal of Roentgenology, AJR, 176: 661-666, Mar. 2001.
Ewing et al. "Patlak Plots of Gd-DTPA MRI Data Yield Blood-Brain Transfer Constants Concordant With Those of 14C-Sucrose in Areas of Blood-Brain Opening", Magnetic Resonance in Medicine, 50: 283-292, 2003.
Fiscus "Molecular Mechanisms of Endothelium-Mediated Vasodilation", Seminars in Thrombosis and Hemostasis, 14(Suppl.): 12-22, 1988.
Furman-Haran et al. "Critical Role of Spatial Resolution in Dynamic Contrast?Enhanced Breast MRI." Journal of Magnetic Resonance Imaging: An Official Journal of the International Society for Magnetic Resonance in Medicine, 13(6): 862-867, Jun. 2001.
Furman-Haran et al. "Response of MCF7 Human Breast Cancer to Tamoxifen: Evaluation by the Three-Time-Point, Contrast-Enhanced Magnetic Resonance Imaging Method1", Clinical Cancer Research,4: 2299-2304, Oct. 1998.
Gabata et al. "Delayed MR Imaging of the Liver: Correlation of Delayed Enhancement of Hepatic Tumors and Pathologic Appearance", Abdominal Imaging, 23:309-313, 1998.

(56) References Cited

OTHER PUBLICATIONS

Gahramanov et al. "Potential for Differentiation of Pseudoprogression From True Tumor Progression With Dynamic Susceptibility-Weighted Contrast-Enahnced Magnetic Resonance Imaging Using Perumoxytol Vs. Gadoteridol: A Pilot Study", International Journal of Radiation: Oncology Biology Physics, XP027581301, 79(2): 514-523, Feb. 1, 2011.
Harris et al. "MRI Measurement of Blood-Brain Barrier Permeability Following Spontaneous Reperfusion in the Starch Microsphere Model of Ischemia", Magnetic Resonance Imaging, 20: 221-230, 2002.
Hazle et al. "Dynamic Imaging of Intracranial Lesions Using Fast Spin-Echo Imaging: Differentiation of Brain Tumors and Treatment Effects", Journal of Magnetic Resonance Imaging, 7(6): 1084-1093, Nov.-Dec. 1997.
Hu et al. "Support Vector Machine Multiparametric MRI Identification of Pseudoprogression From Tumor Recurrence in Patients With Resected Glioblastoma", Journal of Magnetic Resonance Imaging, XP055156185, 33(2): 296-305, Feb. 27, 2011.
Hynynen et al. "Local and Reversible Blood-Brain Barrier Disruption by Noninvasive Focused Ultrasound at Frequencies Suitable for Transl-Skull Sonication", NeuroImage, 24: 12-20, 2005.
Israeli et al. "The Application of MRI for Depiction of Subtle Blood Brain Barrier Disruption in Stroke", International Journal of Biological Sciences, XP003031151, 7(1): 1-8, Dec. 26, 2010. Abstract, Fig.1, p. 2-3, p. 2, col. 1, Para 1, 3, p. 2, col. 2, Para 3-p. 6, col. 1, Para 1, p. 7, col. 1, Para 1-col. 2, Para 2, Figs.
Kilmer et al. "Brainsway Reports Positive Preliminary Results of Study Using Deep TMS to Open the Blood-Brain Barrier in Patients With Brain Tumors", Brainsway, Marketwire L.P., 2 P., Sep. 1, 2011.
Kinoshita et al. "Targeted Delivery of Antibodies Through the Blood-Brain Barrier by MRI-Guided Focused Ultrasound", Biochemical and Biophysical Research Communications, BBRC, 340: 1085-1090, 2006.
Knight et al. "Quantitation and Localization of Blood-to-Brain Influx by Magnetic Resonance Imaging and Quantitative Autoradiography in a Model of Transient Focal Ischemia", Magnetic Resonance in Medicine, 54: 813-821, 2005.
Kratz et al. "Seizure in a Nonpredisposed Individual Induced by Single-Pulse Transcranial Magentic Stimulation", The Journal of ECT, 27(1): 48-50, Mar. 2011. Abstract.
Latour et al. "Early Blood-Brain Barrier Disruption in Human Focal Brain Ischemia", Annals of Neurology, 56: 468-477, 2004.
Lewin et al. "Dual-Energy Constrast-Enhanced Digital Subtraction Mammography: Feasibility", Radiology, 229: 261-268, Mar. 2003.
Li et al. "Prefrontal Cortex Transcranial Magnetic Stimulation Does Not Change Local Diffusion: A Magnetic Resonance Imaging Study in Patients With Depression", Cognitive Behavioral Neurology, XP008169430, 16(2): 128-135, Jun. 2003. Abstract.
Liess et al. "Assessing the Extent of Blood Brain Barrier Breakdown Using Signal Vs. Time Curves and rCBV Maps in Patients With High-Grade Brain Tumours", Proceedings of the International Society for Magnetic Resonance in Medicine, 10: 2085, May 18, 2002.
Macdonald et al. "Response Criteria for Phase II Studies of Supratentorial Malignant Glioma", Journal of Clinical Oncology, 8(7): 1277-1280, Jul. 1990.
Mannelli et al. "Evaluation of Nonenhancing Tumor Fraction Assessed by Dynamic Contrast-Enhanced MRI Subtraction as a Predictor of Decrease in Tumor Volume in Response to Chemoradiotherapy in Advanced Cervical Cancer", American Journal of Roentgenology, AJR, XP003031152, 195(2): 524-527, Aug. 2010. Abstract, p. 525, 2nd Col. "Voxel-by-Voxel Subtraction Was Performed on a Dedicated Workstation".
Marchi et al. "The Etiological Role of Blood-Brain Barrier Dysfunction in Seizure Disorders", Cardiovascular Psychiatry and Neurology, 2011(Article ID): 382415-1-482415-9, 2011.

Miyati "The 1st Multi-Modality Symposium—'Versus' Brain Perfusion—3. From MRI's Perspective", Innervision, 18(2): 17-22, Dec. 2003.
Newatia et al. "Subtraction Imaging: Applications for Nonvascular Abdominal MRI", American Journal of Roentgenology, AJR, 188(4): 1018-1025, Apr. 2007.
Nitsche et al. "MRI Study of Human Brain Exposed to Weak Direct Current Stimulation of the Frontal Cortex", Clinical Neurophysiology, XP004559987, 115(10): 2419-2423, Available Online Jun. 8, 2004. Abstract.
Oberman et al. "Safety of Theta Burst Transcranial Magnetic Stimulation: A Systematic Review of the Literature", Journal of Clinical Neurophysiology, 28(1): 67-74, Feb. 2011.
Pandit "Non-Cartesian MR Microscopy for Cancer Imaging in Small Animals", Dissertation Submitted to Department of Biomedical Engineering, Duke University, 149 pages, 2010.
Plewnia et al. "Transient Suppression of Tinnitus by Transcranial Magnetic Stimulation", Annals in Neurology, 53: 263-266, 2003.
Powers et al. "The High-Resolution, Three-Dimensional Solution Structure of Human Interleukin-4 Determined by Multidimensional Heteronuclear Magnetic Resonance Spectroscopy", Biochemistry, 32: 6744-6762, 1993. p. 6746, Lines 16-24.
Ravnborg et al. "No Effect of Pulsed Magnetic Stimulation on the Blood-Brain Barrier in Rats", Neuroscience, 38(1): 277-280, 1990. Abstract.
Sheikov et al. "Cellular Mechanisms of the Blood-Brain Barrier Opening Induced by Ultrasound in Presence of Microbubbles", Ultrasound in Medicine & Biology, 30(7): 979-989, 2004.
Shindo et al. "Blood-Brain Barrier Dysfunction in White Matter Lesions of Elderly Patients With Dementia", The Journal of Tokyo Medical University, Japan, 63(5): 395-400, Sep. 2005. Abstract in English.
Taheri et al. "Kalman Filtering for Reliable Estimation of BBB Permeability", Magnetic Resonance Imaging, 24: 1039-1049, 2006.
Tofts "Optimal Detection of Blood-Brain Barrier Defects With Gd-DTPA MRI—The Influences of Delayed Imaging and Optimised Repetition Time", Magnetic Resonance Imaging, 14(4): 373-380, 1996.
Tomkins et al. "Blood-Brain Barrier Disruption in Post-Traumatic Epilepsy", Journal of Neurology, Neurosurgery, and Psychiatry, 79(7): 774-777, Published Online Nov. 8, 2007.
Van den Bent et al. "End Point Assessment in Gliomas: Novel Treatments Limit Usefulness of Classical Macdonald's Criteria", Journal of Clinical Oncology, 27(18): 2905-2908, Jun. 20, 2009.
Vovk et al. "A Review of Methods for Correction of Intensity Inhomogeneity in MRI", IEEE Transactions on Medical Imaging, 26(3): 405-421, Mar. 2007.
Wang et al. "Vascular Volume and Blood-Brain Barrier Permeability Measured by Dynamic Contrast Enhanced MRI in Hippocampus and Cerebellum of Patients With MCI and Normal Controls", Journal of Magnetic Resonance Imaging, 24: 695-700, 2006.
Wen et al. "Malignant Gliomas in Adults", The New England Journal of Medicine, 359(5): 492-507, Jul. 31, 2008.
Wong et al. "Outcomes and Prognostic Factors in Recurrent Glioma Patients Enrolled Onto Phase II Clinical Trials", Journal of Clinical Oncology, 17(8): 2572-2578, Aug. 1999.
Yahaghi et al. "Estimation of Contrast Agent Concentration in Intra- and Extra-Vascular Spaces of Brain Tissue", Mathematical Biosciences, 204: 102-118, 2006.
Zach et al. "Delayed Contrast Extravasation MRI for Depicting Tumor and Non-Tumoral Tissues in Primary and Metastatic Brain Tumors", POS One, XP055320974, 7(12): e52008-1-e52008-17, Dec. 14, 2012. p. 4-6, 9.
Official Action dated Aug. 31, 2023 from the US Patent and Trademark Office Re. U.S. Appl. No. 16/992,160. (9 pages).
Official Action dated May 24, 2023 from the US Patent and Trademark Office Re. U.S. Appl. No. 16/992,160. (33 pages).
Notice of Allowance dated Nov. 24, 2023 from the US Patent and Trademark Office Re. U.S. Appl. No. 16/992,160. (8 pages).

* cited by examiner

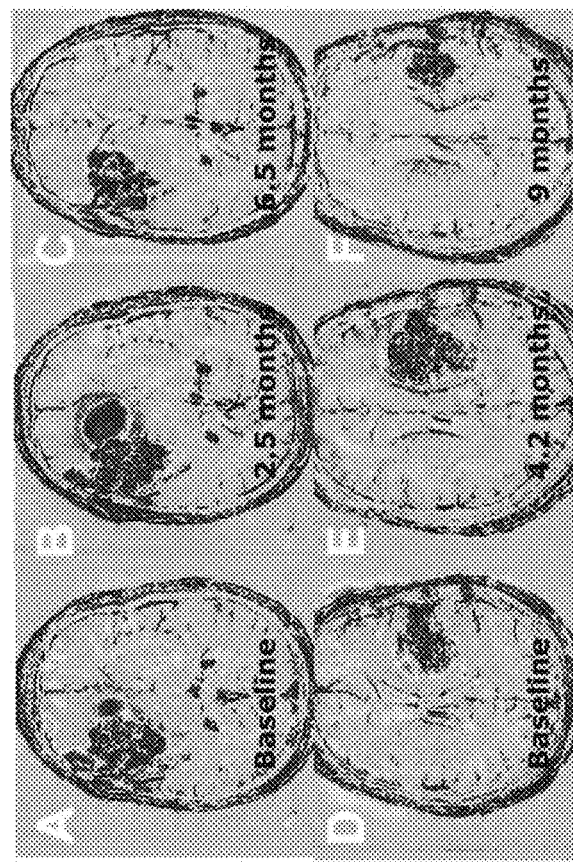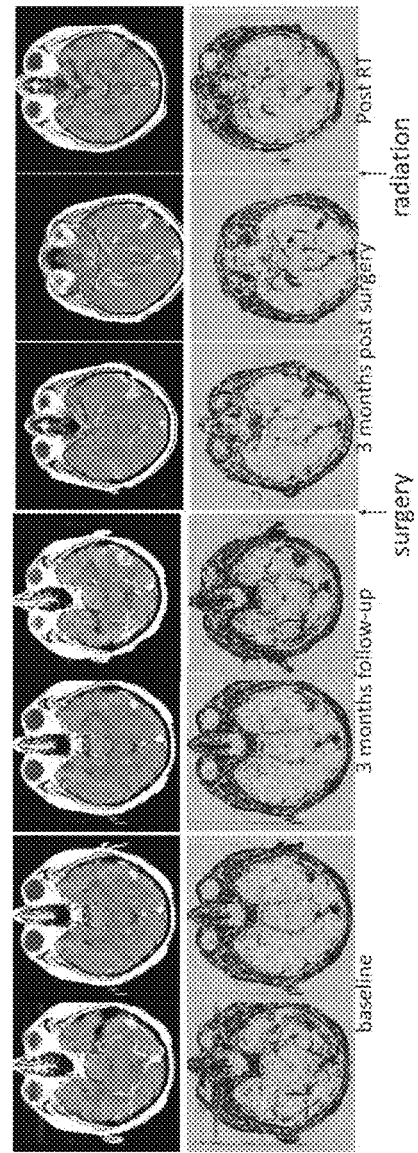

FIG. 18A  FIG. 18B  FIG. 18C
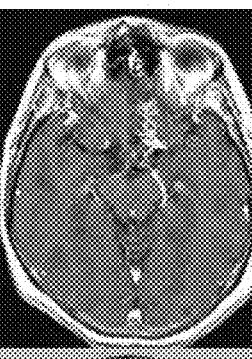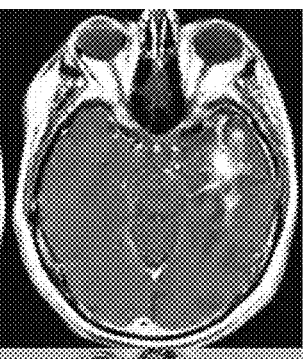
FIG. 18D  FIG. 18E  FIG. 18F
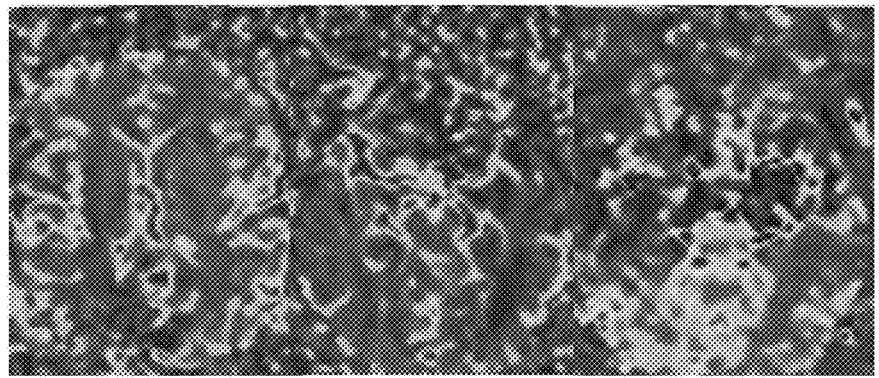
FIG. 18G  FIG. 18H  FIG. 18I

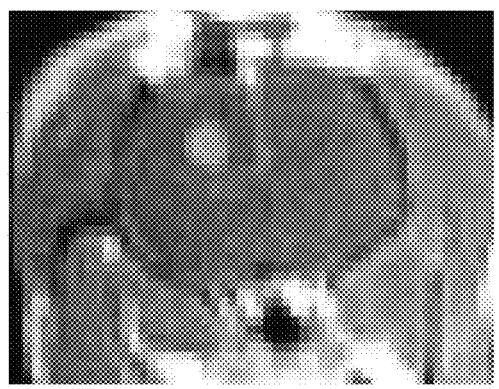 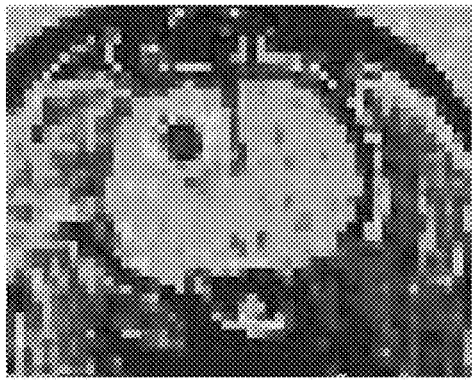
FIG. 25A        FIG. 25B
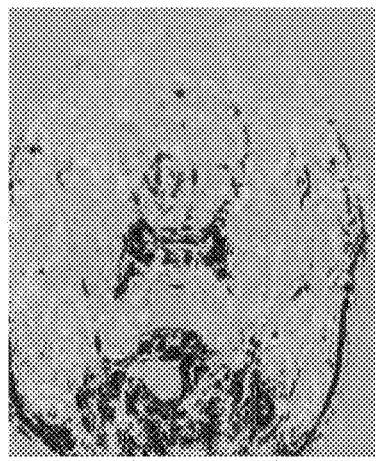 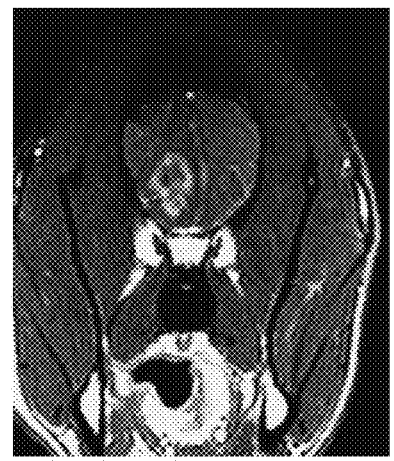
FIG. 26A        FIG. 26B
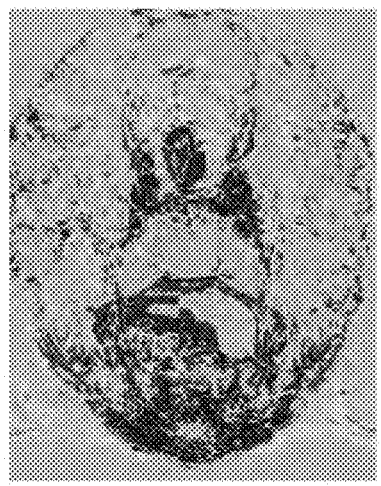 
FIG. 26C        FIG. 26D

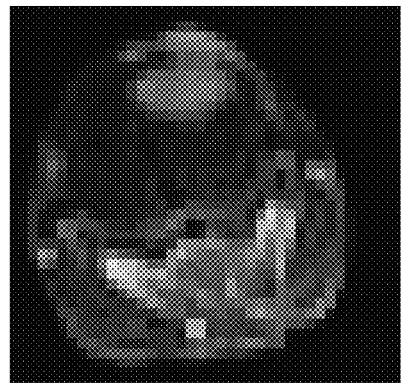
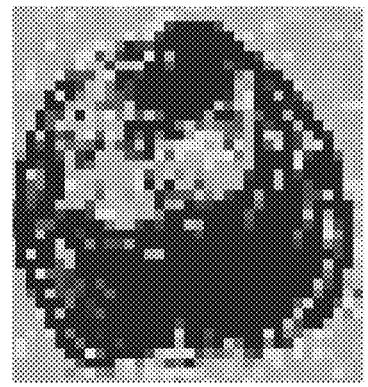
FIG. 27A  FIG. 27B
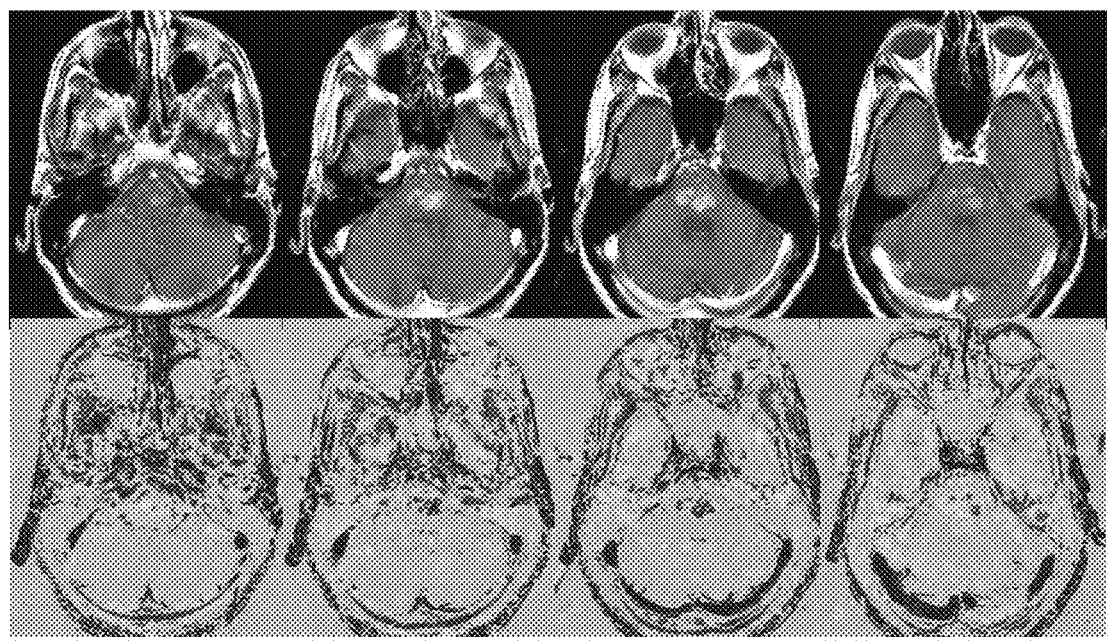
FIG. 28A

MAGNETIC RESONANCE MAPS FOR ANALYZING TISSUE

RELATED APPLICATIONS

This application is a continuation of U.S. patent application Ser. No. 14/787,040 filed on Oct. 26, 2015, which is a National Phase of PCT Patent Application No. PCT/IB2014/060981 having International Filing Date of Apr. 24, 2014, which claims the benefit of priority under 35 USC § 119(e) of U.S. Provisional Patent Application No. 61/815,343 filed on Apr. 24, 2013. The contents of the above applications are all incorporated by reference as if fully set forth herein in their entirety.

FIELD AND BACKGROUND OF THE INVENTION

The present invention relates to method and apparatus for producing magnetic resonance (MR) maps and, more particularly, but not exclusively to using such maps to identify and study tumors.

MRI is considered the gold standard imaging modality for the brain. Although MRI provides high resolution and good sensitivity, standard MR sequences still suffer of low specificity especially in the case of tumors, e.g., brain tumors (during/after treatment).

Gliomas are the most common malignant primary brain tumors in adults, with an annual incidence of 4-5 per 100,000 people (Central Brain Tumor Registry; Wen and Kesari, 2008).

The standard of care for glioblastoma includes surgery, chemotherapy during and after radiotherapy. The use of temozolomide (TMZ) both during radiotherapy and for six months post radiotherapy results in a significant increase in median survival with minimal additional toxicity. This treatment regime is now standard for most cases of glioblastoma where the patient is not enrolled in a clinical trial.

Temozolomide seems to work by sensitizing the tumor cells to radiation. The U.S. Food and Drug Administration approved Bevacizumab (Avastin) to treat patients with glioblastoma at progression after standard therapy based on the results of 2 studies that showed Bevacizumab reduced tumor size in some glioblastoma patients.

Treatment efficacy assessment of high-grade gliomas is currently based on overall survival or, more commonly in patients with recurrent disease, on progression-free survival (PFS) (Wong et al, 1999; Lamborn et al, 2008), determined by radiographic response. The Macdonald criteria (Macdonald et al, 1990), published in 1990, provided an objective radiologic assessment of tumor response, based on the product of the maximal cross-sectional enhancing diameters as the primary tumor measure. In the Macdonald Criteria, a significant increase (at least 25%) in the contrast-enhancing lesion is used as a reliable surrogate marker for tumor progression, and its presence mandates a change in therapy. However, increased enhancement can also be induced by a variety of non-tumoral processes such as treatment-related inflammation, seizure activity, postsurgical changes, ischemia, sub-acute radiation effects, and radiation necrosis (Van den Bent et al, 2009).

In this context, post-treatment radiographic changes observed within several months of temozolomide-based chemoradiation, have been recently referred to as pseudo-progression. This treatment related effect has implications for patient management and may result in premature discontinuation of effective adjuvant therapy. This limits the validity of a progression free survival end point unless tissue-based confirmation of tumor progression is obtained. It also has significant implications for selecting appropriate patients for participation in clinical trials for recurrent gliomas. Pseudoprogression was widely reported within the last 5 years in glioma patients undergoing standard chemoradiation. These papers demonstrate that 26-58% of the patients suffer early disease progression at first post-concomitant chemoradiation imaging. Within those patients which continued treatment, 28-66% showed radiologic improvement or stabilization and were defined retrospectively as manifesting pseudoprogression.

Thus, treatment decisions, as to whether to operate on a patient with radiographic deterioration, continue chemotherapy or change to another non-surgical treatment is a day to day struggle involving interdisciplinary teams of neurosurgeons, neuro-oncologists and neuro-radiologists who are often unable to reach a unanimous interpretation of the patient status.

For glioblastoma patients treated by radiation and TMZ, conventional MRI is unable to provide a reliable distinction between tumor progression and treatment effects (also referred to as pseudoprogression). For glioblastoma patients conventional MRI is unable to reliable depict the tumor or pseudoprogression after treatment with Bevacizumab.

MRS can distinguish residual or recurrent tumors from pure treatment-related necrosis, but not from mixed necrosis and tumor tissue. Diffusion weighted MRI (DWMRI) has also been assessed for differentiating tumor/necrosis after RT, however, the specificity of DWMRI is less than MRS. It has been suggested that combining DWMRI with MRS may improve the differentiation. FDG-PET has been shown to be useful in differentiating necrosis from recurrence, but the reported sensitivity and specificity were again low.

A number of MRI techniques have been applied to study microvasculature parameters in this context. The two most commonly used methods are dynamic contrast-enhanced MRI (DCE MRI) and dynamic susceptibility-weighted contrast MRI. DCE MRI measures the changes in T1 relaxation associated with disrupted blood brain barrier following contrast administration using parameters such as fractional blood volume (fBV) and permeability (Kps or Ktrans). DSC MRI uses echo planar sequences with a rapid bolus of gadolinium-based contrast agents to assess changes in T2* within the vasculature and interstitial space. Typical calculated parameters are the relative peak height (rPH), relative cerebral blood volume (rCBV) and the percentage recovery (% REC) or recirculation factor (RF).

Parametric maps that are derived from DCE and DSC data have been proposed as noninvasive methods for assessing response to therapy. Radiation necrosis typically shows decreased rCBV, whereas recurrence shows high rCBV. Unfortunately, there was significant overlap between the two groups. More encouraging results were obtained using delayed T1-weighted MRI (T1-MRI) permeability methods, which image beyond the first pass circulation of contrast, sometimes as long as 10-15 min. using such a delay, one group was able to reliably distinguish between recurrence, radiation necrosis, and a combination of both factors. They found that radiation necrosis and tumor enhance at different rates, enabling significant differentiation between recurrent tumor, radiation necrosis and mixed radiation necrosis and tumor (p<0.001). One group showed that using intra-tumoral and peri-tumoral MRI information it was possible to predict activation of hypoxia and proliferation gene-expression programs, respectively. Furthermore, the intratumoral distribution of gene-expression patterns was found to predict patient outcome.

DSC was recently applied, demonstrating the feasibility for differentiating pseudoprogression from real tumor progression using ferumoxytol. One group applied DCE to a cohort of 29 patients with gliomas and brain metastasis suspected of treatment-induced necrosis or recurrent/progressive tumor and demonstrated the feasibility of predicting real progression. Another group applied DSC MRI for differentiating tumor progression from radiation necrosis in glioblastoma multiforme (GBM) patients undergoing external beam radiation therapy. Their analysis showed that rPH and rCBV were significantly higher in patients with recurrent GBM than in patients with radiation necrosis while the % REC values were significantly lower.

Brain metastases are the most common intracranial tumor in adults, occurring in approximately 10% to 30% of adult cancer patients. It is believed that the annual incidence is rising (due to better treatment of systemic disease and improved imaging modalities). The prognosis of patients diagnosed with brain metastases is generally poor.

Stereotactic radiosurgery (SRS) is a radiotherapy technique which permits the delivery of a single large dose of radiation to the tumor while minimizing irradiation of adjacent normal tissue. It is applied to treat both benign and malignant tumors as well as for vascular lesions and functional disorders. Among the reported complications of SRS is radiation-induced necrosis which, similarly to pseudoprogression, can be difficult to differentiate both clinically and radiologically from recurrent tumor at the treatment site. The incidence of radiation induced necrosis may vary between 5% to 11% according to the volume of the treated lesion and the applied dose (19).

Tumor progression, inflammation, infection and treatment-induced changes (such as radiotherapy-induced changes) can induce similar changes in enhancement which are impossible to differentiate.

Previous studies suggest that ~50% of glioblastoma multiforme (GBM, the most frequent and aggressive high grade primary brain tumor) patients and up to ~20% of patients with brain metastases who present radiological deterioration after treatment do not suffer from tumor recurrence but from treatment effects (TEs). These changes, induced by the treatment, often termed pseudoprogression in the case of GBM and radiation necrosis in the case of brain metastases, are depicted as increasing volumes of contrast-enhancing lesions on conventional MRI, mimicking tumor progression. Treatment decision, as whether to operate on a patient with radiographic deterioration, continue current treatment/follow-up or change to another non-surgical treatment is a daily struggle involving interdisciplinary teams of neurosurgeons, neuro-oncologists and neuro-radiologists which are often unable to reach unanimous interpretation of the patient's status. Therefore, reliable distinction between these conditions is essential for appropriate patient management.

The fact that increases in enhancing lesion volume in 20-30% of patients is due to treatment effects rather than tumor progression, prevents appropriate treatment in ~50% of patients with brain tumors. Some of these patients undergo unnecessary surgeries or treatment changes when continuation of the current treatment should be the correct choice, while others do not receive the necessary surgery/treatment on time. In both cases, the wrong choice of treatment significantly hampers the patient's quality of life and survival. For patients suffering from these devastating diseases, with survival measured in months, taking the right decision at the right time is a matter of life and death.

Conventional MRI is currently unable to provide reliable distinction between tumor progression and treatment effects such as pseudoprogression and radiation necrosis. MR spectroscopy (MRS) can distinguish residual or recurrent tumors from pure treatment-related necrosis, but not from mixed necrosis and tumor tissue. Diffusion weighted MRI (DWMRI) and diffusion-tensor MRI have also been assessed for differentiating tumor/necrosis after RT, however, the specificity of DWMRI is less than MRS. FDG-PET has been shown to be useful in differentiating RN from recurrence, but the reported sensitivity/specificity of FDG PET in the brain are low. There is limited, but increasing evidence that PET with amino acid tracers may contribute to the differentiation between treatment effects and recurrence. Whether these techniques will also allow a reliable distinction between pseudoprogression and real progression is yet to be determined.

The most studied MRI methodology in this context is perfusion-weighted MRI (PWI), applied for assessing microvasculature parameters. The most commonly applied PWI methods are dynamic contrast-enhanced MRI (DCE MRI) and dynamic susceptibility-weighted contrast MRI (DSC MRI). Parametric maps derived from DCE and DSC have been proposed for assessing response to therapy. Treatment induced changes typically show decreased relative cerebral blood volume (rCBV), whereas recurrence shows high rCBV. Still, most of these studies show some degree of overlap between the two disease entities. In addition, using fast acquisition techniques has the disadvantages of low spatial resolution and high sensitivity to susceptibility artifacts. Due to these limitations, in many cases the data is inconclusive and significant results are mostly obtained by averaging over the entire enhancing lesion while important information regarding the location and shape of small active tumor regions may be limited. This effect stands out especially in the case of GBM, where pseudoprogression hardly ever describes a status with no residual tumor (unlike the case of brain metastases and RN where complete tumor resolution is more likely to occur), as we know that the vast majority of all GBM patients, including those experiencing pseudoprogression, eventually recur.

SUMMARY OF THE INVENTION

According to an aspect of some embodiments of the present invention there is provided apparatus for operating MRI, comprising: a control for operating an MRI scanner to carry out an MRI scan of an organ of a subject; an input for receiving first and second MRI scans respectively at the beginning and end of a predetermined time interval post contrast administration; a subtraction map former for forming a subtraction map from the first and the second MRI scans by analyzing the scans to distinguish between two primary populations, a slow population, in which contrast clearance from the tissue is slower than contrast accumulation, and a fast population in which clearance is faster than accumulation; and an output to provide an indication of distribution of the two primary populations, wherein the control is configured to carry out the first scan at least five minutes and no more than twenty minutes post contrast administration and to carry out the second scan such that the predetermined time period is at least twenty minutes.

According to an aspect of some embodiments of the present invention there is provided apparatus for operating MRI, comprising: an MRI Scanner configured for performing a 3D MRI scan; an input for receiving first and second MRI scans of an organ of a subject respectively at the beginning and end of a predetermined time interval post contrast administration from the MRI scanner; a subtraction map former for forming a subtraction map from the first and the second MRI scans by analyzing the scans to distinguish between two primary populations, a slow population, in which contrast clearance from the tissue is slower than contrast accumulation, and a fast population in which clearance is faster than accumulation; and an output to provide an indication of distribution of the two primary populations, wherein the control is configured to carry out the first scan and the second scan such that the predetermined time period is at least twenty minutes.

According to some embodiments of the invention the subtraction map former comprises an intensity map constructor for constructing, for each magnetic resonance image, an intensity map, wherein the subtraction map describes variations in concentration of the contrast agent in the organ by detecting dissimilarities among a pair of intensity maps.

According to some embodiments of the invention the predetermined time period is any one of the group consisting of: more than twenty minutes, more than thirty minutes, more than forty minutes, more than fifty minutes, more than sixty minutes, more than seventy minutes, more than eighty minutes, more than ninety minutes, more than a hundred minutes, seventy minutes, seventy five minutes and ninety minutes.

According to some embodiments of the invention the subtraction map former is configured for assigning a representative intensity value for a selected ROI in each magnetic resonance image and determining a time-dependence of the representative intensity value.

According to some embodiments of the invention the subtraction map former is configured for differentiating between morphologically active tumor represented by the fast population, and a non-tumoral tissue represented by the slow population.

According to some embodiments of the invention the input receives from the MRI scanner at least one additional MRI scans before the first MRI scan, the MRI scans being acquired post contrast administration, and wherein the subtraction map former is configured for forming a first subtraction map using the additional MRI scan and the second MRI scan, and a second subtraction map using the first MRI scan and the second MRI scan.

According to some embodiments of the invention the subtraction map former is configured for forming a third map having regions corresponding to the slow population as obtained from the first map, and regions corresponding to the fast population as obtained from the second map.

According to some embodiments of the invention the slow population corresponds to an abnormal but non-tumoral tissue region.

According to some embodiments of the invention the abnormal but non-tumoral tissue region corresponds to a treatment effect.

According to some embodiments of the invention the abnormal but non-tumoral tissue region corresponds to an inflammation.

According to some embodiments of the invention the abnormal but non-tumoral tissue region corresponds to BBB disruption.

According to some embodiments of the invention the apparatus is configured to carry out image pre-processing.

According to some embodiments of the invention the preprocessing comprises registration.

According to some embodiments of the invention the preprocessing comprises correction for intensity variations.

According to some embodiments of the invention the apparatus comprises a registration unit for carrying out registration between corresponding MRI images.

According to some embodiments of the invention the registration comprises a rigid body registration.

According to some embodiments of the invention the registration comprises an elastic registration to allow for head movements and resulting distortions between respective scans.

According to some embodiments of the invention the elastic registration comprises dividing each slice of a respective scan into to a grid of volumes, and allowing each volume to move freely in three dimensions until a sum of the absolute values of the intensity difference between the two time points reaches a minimum.

According to some embodiments of the invention the apparatus comprises a smoothing and interpolation unit for smoothing a 3 dimensional translation matrix resulting from the registration using circular smearing, and interpolating to obtain translation values per pixel.

According to some embodiments of the invention the apparatus comprises a data processor configured for estimating a progression time of a tumor, based on initial growth rate in the fast population.

According to an aspect of some embodiments of the present invention there is provided a method for analyzing MRI of an organ of a subject, comprising: receiving a first and a second MRI scan at the beginning and end of a predetermined time interval post contrast administration, wherein the time interval begins at least five minutes and no more than ten minutes post contrast injection; forming a subtraction map from the first and the second MRI scans by analyzing the scans to distinguish between two primary populations, a slow population, in which contrast clearance from the tissue is slower than contrast accumulation, and a fast population in which clearance is faster than accumulation; and providing an indication of distribution of the two primary populations, wherein the predetermined time period is at least twenty minutes.

According to an aspect of some embodiments of the present invention there is provided a method for analyzing MRI of an organ of a subject, comprising: receiving a first and a second 3D MRI scan at the beginning and end of a predetermined time interval post contrast administration; forming a subtraction map from the first and the second 3D MRI scans by analyzing the scans to distinguish between two primary populations, a slow population, in which contrast clearance from the tissue is slower than contrast accumulation, and a fast population in which clearance is faster than accumulation; and providing an indication of distribution of the two primary populations, wherein the predetermined time period is at least twenty minutes.

According to some embodiments of the invention the forming comprises constructing, for each magnetic resonance image, an intensity map, wherein the subtraction map describes variations in concentration of the contrast agent in the organ by detecting dissimilarities among a pair of intensity maps.

According to some embodiments of the invention the method further comprising using the map to distinguish between residual tumor post-surgery and post-surgical changes.

According to some embodiments of the invention the predetermined time period is any one of the group consisting of: more than twenty minutes, more than thirty minutes, more than forty minutes, more than fifty minutes, more than sixty minutes, more than seventy minutes, more than eighty minutes, more than ninety minutes, more than a hundred minutes, seventy minutes, seventy five minutes and ninety minutes.

According to an aspect of some embodiments of the present invention there is provided a method comprises receiving at least one additional MRI scans before the first MRI scan, the additional MRI scan being acquired post contrast administration, and wherein the forming the subtraction map comprises forming a first subtraction map using the additional MRI scan and the second MRI scan, and a second subtraction map using the first MRI scan and the second MRI scan.

According to some embodiments of the invention the method comprises identifying the slow population using the first map, and for identifying the fast population using the second map.

According to some embodiments of the invention the method comprises identifying the slow population using the first map but not the second map, and for identifying the fast population using the second map but not the first map.

According to some embodiments of the invention the method comprises forming a third map having regions corresponding to the slow population as obtained from the first map, and regions corresponding to the fast population as obtained from the second map.

According to some embodiments of the invention the method comprises assigning a representative intensity value for each magnetic resonance image and determining a time-dependence of the representative intensity value.

According to some embodiments of the invention the method comprises generating a graph describing the time-dependence.

According to some embodiments of the invention the method comprises determining, from the subtraction map, whether tumour tissue is present, by comparing drainage of the contrast agent from blood vessels with contrast agent take up in the tissue.

According to some embodiments of the invention the method comprises differentiating between morphologically active tumor represented by the fast population, and a non-tumoral tissue represented by the slow population.

According to some embodiments of the invention the method comprises carrying out image preprocessing.

According to some embodiments of the invention the preprocessing comprising registration.

According to some embodiments of the invention the preprocessing comprising correction for intensity variations.

According to some embodiments of the invention the correction for intensity variations comprises calculating, for each MRI image separately, an intensity variation map consisting of large scale intensity variations therein and then subtracting the intensity variation map from the respective image.

According to some embodiments of the invention the method comprises estimating a progression time of a tumor, based on initial growth rate in the fast population.

According to some embodiments of the invention the method comprises using the maps for differentiation between tumor progression and radiation necrosis.

According to some embodiments of the invention the method comprises depiction of tumors in the organ after treatment with chemotherapy and/or radiation-based treatments, for differentiation between tumor progression and pseudoprogression.

According to an aspect of some embodiments of the present invention there is provided a method for managing tumor treatment in patients, comprising: receiving a first and a second 3D MRI scan at the beginning and end of a predetermined time interval post contrast administration; forming a subtraction map from the first and the second 3D MRI scans by analyzing the scans to distinguish between two primary populations, a slow population, in which contrast clearance from the tissue is slower than contrast accumulation, and a fast population in which clearance is faster than accumulation; and providing an indication of distribution of the two primary populations, wherein the predetermined time period is at least twenty minutes; using the subtraction map and the indication to distinguish between tumor and non-tumor tissue and thereby to provide information for determination of further treatment.

According to some embodiments of the invention the the subject has a cancer of a type selected from the group consisting of a brain tumor, Ewing sarcoma, a Head and neck tumor, a lung cancer, a colon and rectum cancer, a breast cancer, a prostate cancer, a urinary cancer, a uterine cancer, a bladder cancer, an oral cancer, a pancreatic cancer, a stomach cancer, an ovarian cancer, a liver cancer, a laryngeal cancer, a thyroid cancer, a esophageal cancer, and a testicular cancer.

According to some embodiments of the invention the organ is selected from the group consisting of brain, colon, prostate, bladder, breast, chest, lung, liver, bones and bone marrow, ovary, kidneys, spleen, thyroid gland, pancreas, head and neck, extremities, skin, lymph nodes, brain, colon, prostate, breast, lung, liver, bones and bone marrow, ovary, pancreas, head and neck, skin, abdomen, eyes, heart, stomach.

Some embodiments of the present invention are used for depiction of a space occupying lesion (SOL) in the organ after treatment, for differentiation between disease progression and treatment effects.

According to some embodiments of the invention the SOL comprises at least one object selected from the group consisting of a brain tumor, a primary brain tumor and a brain metastasis.

According to some embodiments of the invention the SOL comprises at least one object selected from the group consisting of an AVM, a cavernoma, a meningioma, a chordoma and a rare tumor.

According to some embodiments of the invention the treatment is selected from the group consisting of a chemotherapy, a ionizing radiation therapy, a radiation therapy, a focused radiation therapy, radiosurgery, gamma-knife therapy, intensity modulated therapy, a physical therapy, a thermal therapy, an electrical therapy, an electromagnetic therapy, a radiofrequency therapy, an ultrasound therapy, focused-ultrasound therapy, Transcranial magnetic stimulation, electroporation therapy, laser therapy, cryogenic therapy, anti-angiogenic therapy, immuno-therapy, genetic-based therapy, therapy based on convection-enhanced delivery, and any combination thereof.

According to some embodiments of the invention the treatment the SOL comprises high-grade glioma, and the treatment comprises chemotherapy, ionizing radiation therapy and a combination of chemotherapy, ionizing radiation therapy.

According to some embodiments of the invention the treatment the SOL comprises brain metastasis, and the treatment comprises ionizing radiation therapy, including whole brain radiation therapy and focused radiation therapy such as, but not limited to, radiosurgery and gamma knife therapy.

Some embodiments of the present invention are used for depiction of residual tumor post surgery.

Some embodiments of the present invention are used for guiding a local treatment of tumor. According to some embodiments of the invention the local treatment is at a spatial resolution of less than 5 mm, more preferably less than 2 mm, more preferably 1 mm or less.

Some embodiments of the present invention are used for detecting active tumor within bleeding regions.

Some embodiments of the present invention are used for differentiating malignant transformation from treatment effects in treated low grade tumors.

Some embodiments of the present invention are used for depiction of tumors in the organ after treatment with anti-angiogenic treatments and studying the mechanism of action and response patterns of anti-angiogenic drugs.

Some embodiments of the present invention are used for depiction of tumors in the organ after treatment with radiation-based treatments, for differentiation between tumor progression and radiation necrosis.

Some embodiments of the present invention are used for depiction of tumors in the organ after treatment with radiation-based treatments, for differentiation between tumor progression and pseudoprogression.

Some embodiments of the present invention are used for differentiation between progression of brain space occupying lesion (SOL) and treatment effects following focused radiation treatments such as radiosurgery and gamma knife treatments.

According to some embodiments of the invention the MRI is of a subject diagnosed with GBM, wherein the subtraction map former is configured to identify changes in a volume of the fast population volume, and wherein the output is configured to indicate progression when the increment is above a predetermined threshold.

Some embodiments of the present invention are used for identifying change in a volume of the fast population volume, wherein a level of increment above a predetermined threshold indicates tumor progression.

Some embodiments of the present invention are used for differentiating open AVM from at least one of closed AVM and treatment effects.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 9A-9F illustrate two examples in which mappings according to the present embodiments contrast tumor progression effectively against pseudo-progression;

FIG. 10 illustrates MRI scans and mapping according to the present embodiments of the breast cancer patient of example 4 before and after surgery;

Figure 15:
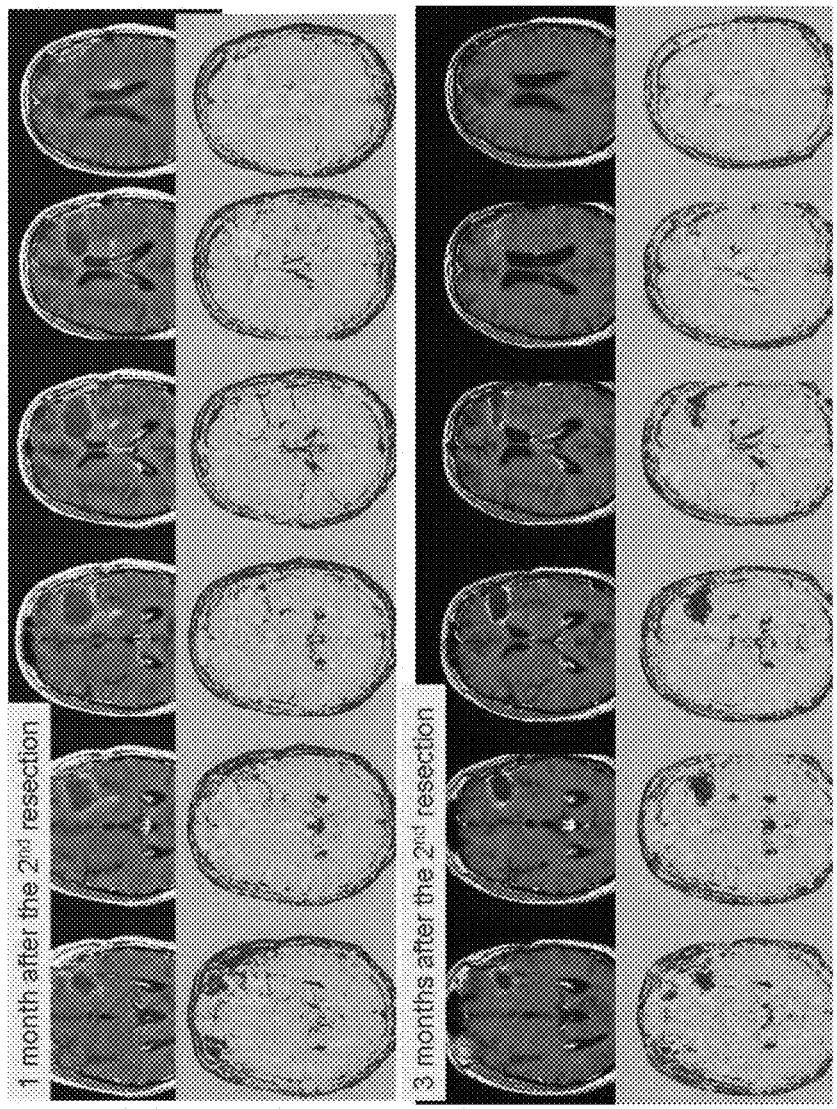
Figure 16:
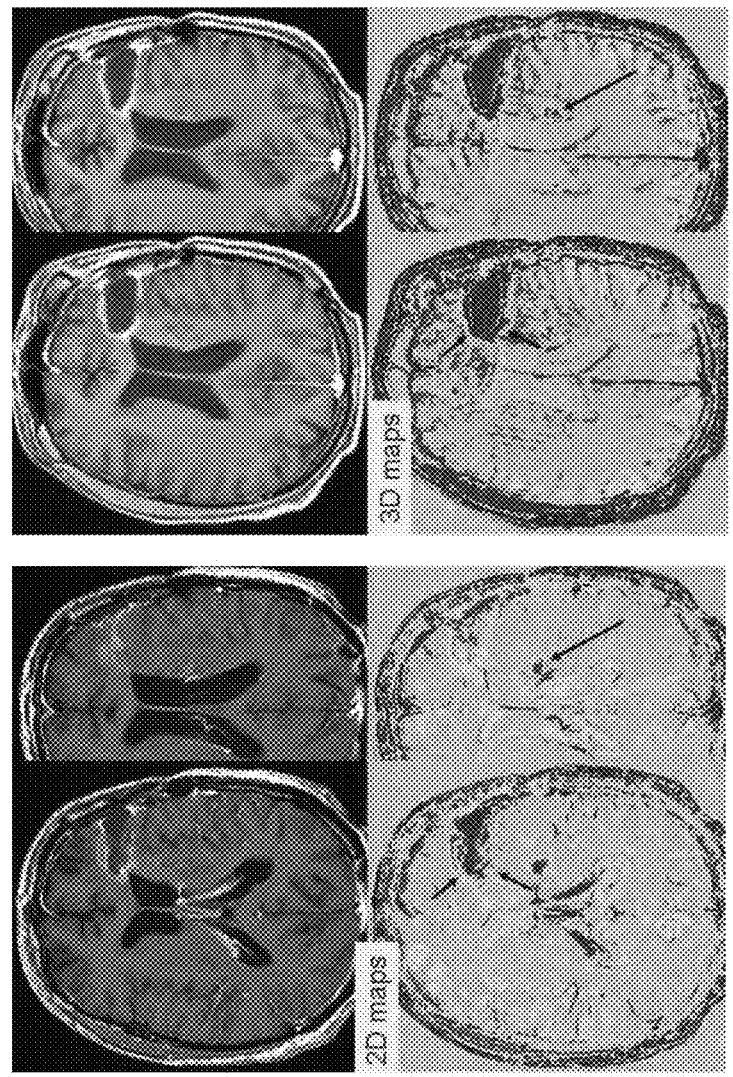
Figure 17:
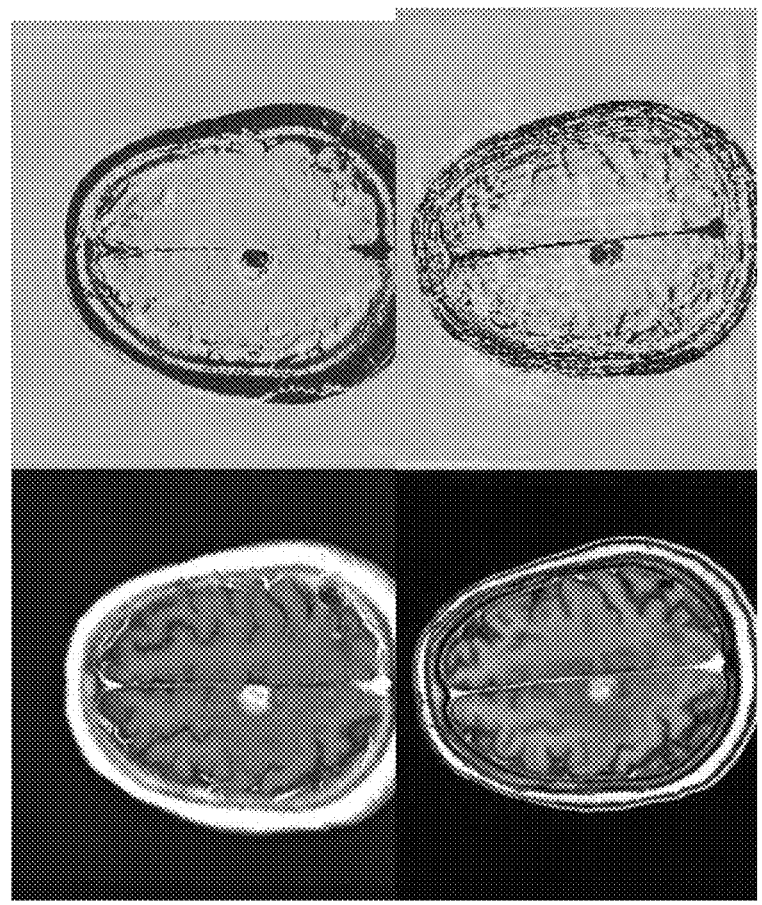
Figure 19:
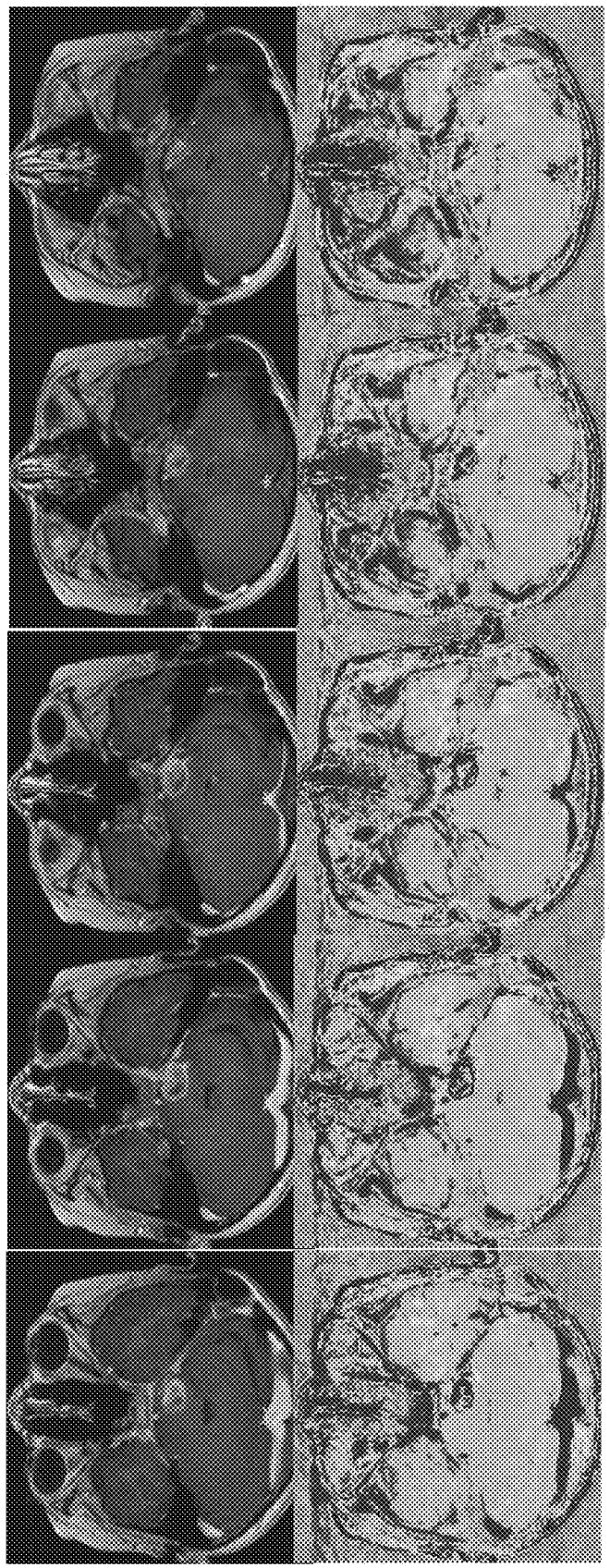
Figure 20A:
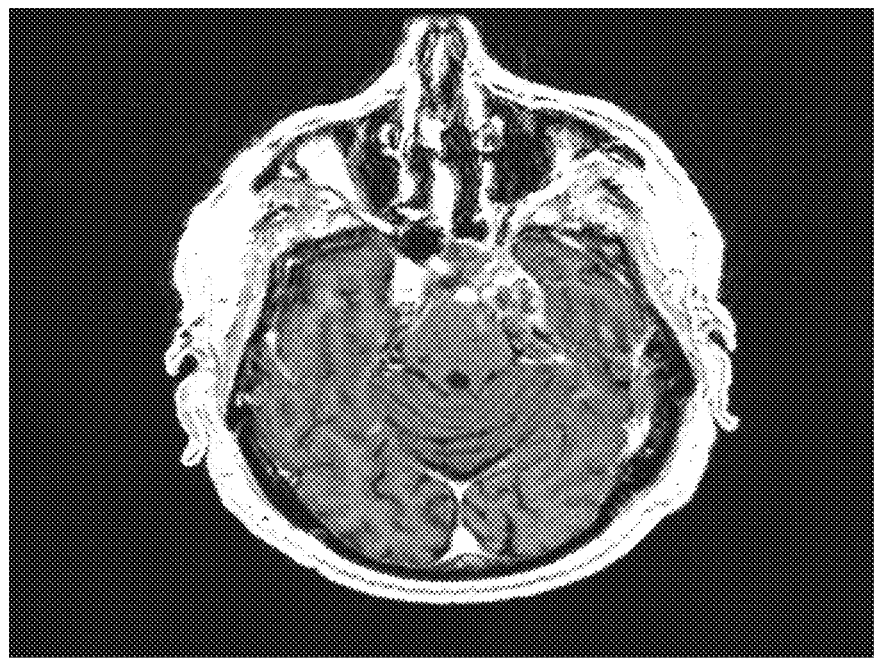
Figure 20B:
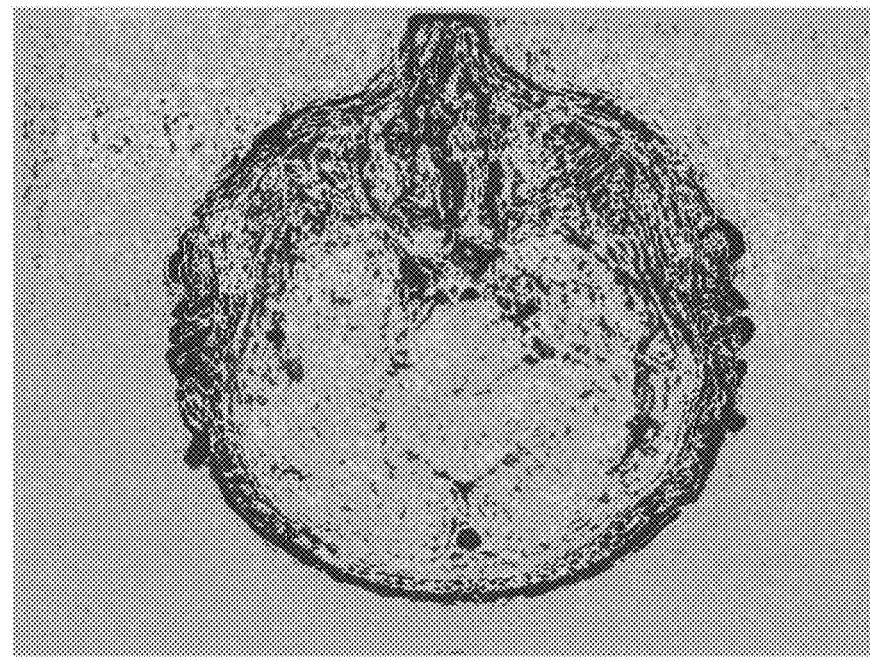
Figure 21A:
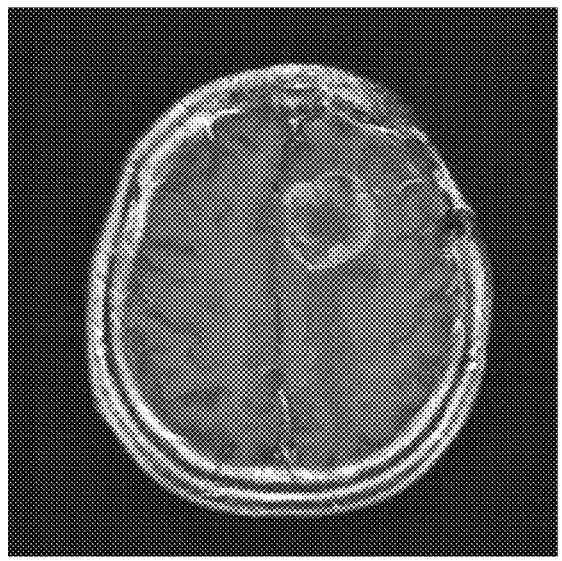
Figure 21B:
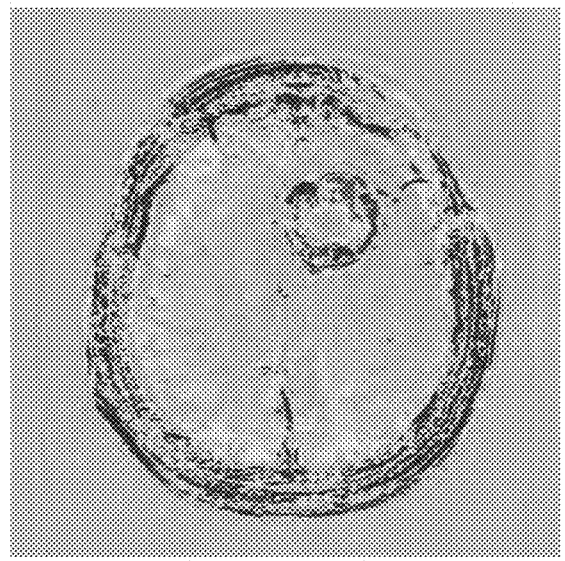
Figure 23A:
Figure 23B:
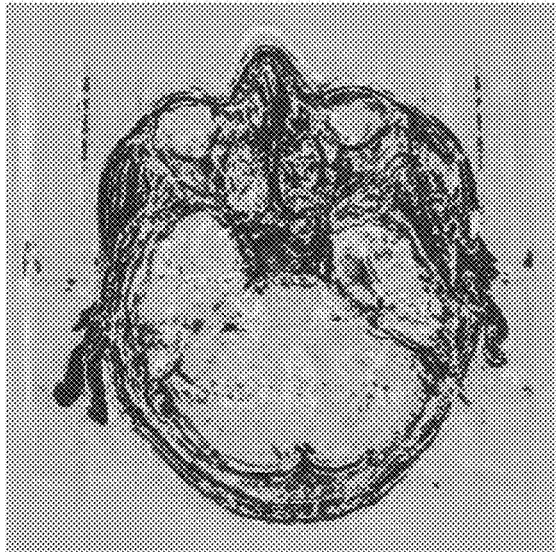
Figure 24A:
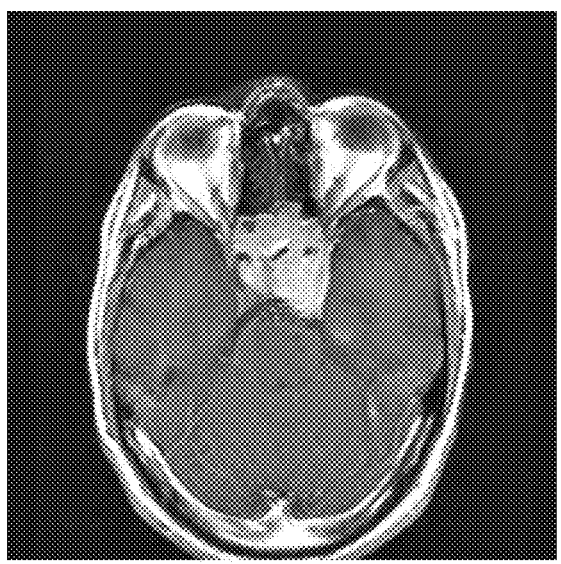
Figure 24B:
Figure 28B:
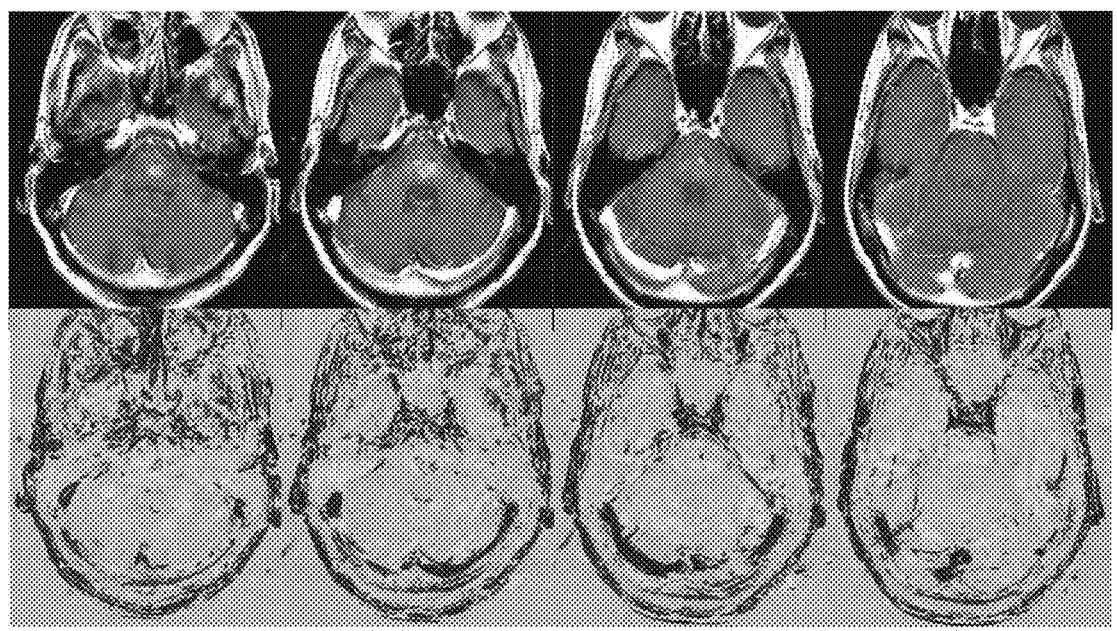
Figure 29A:
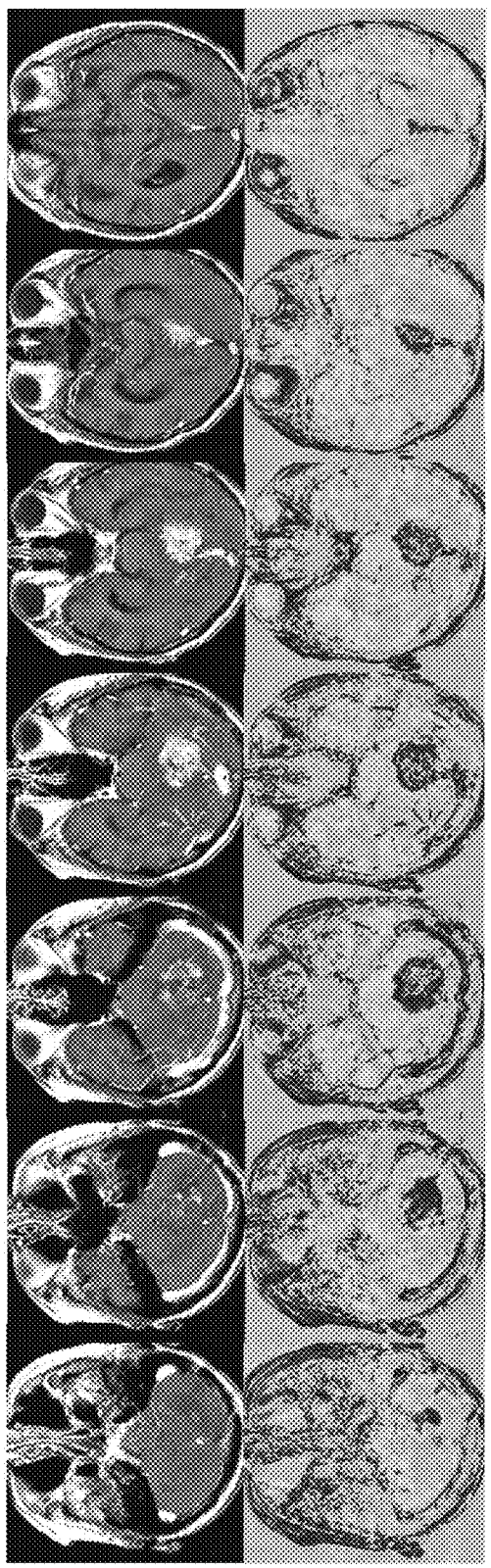
Figure 29B:
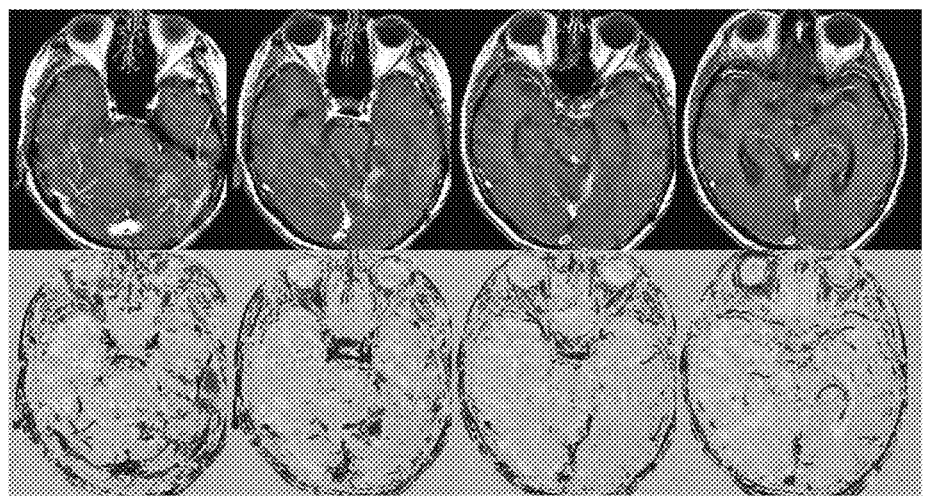
Figure 30A:
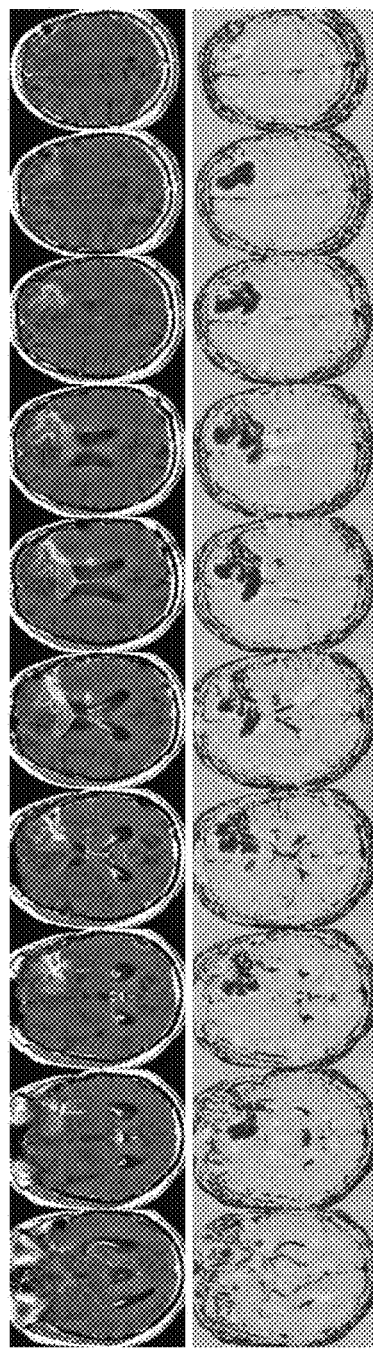
Figure 30B:
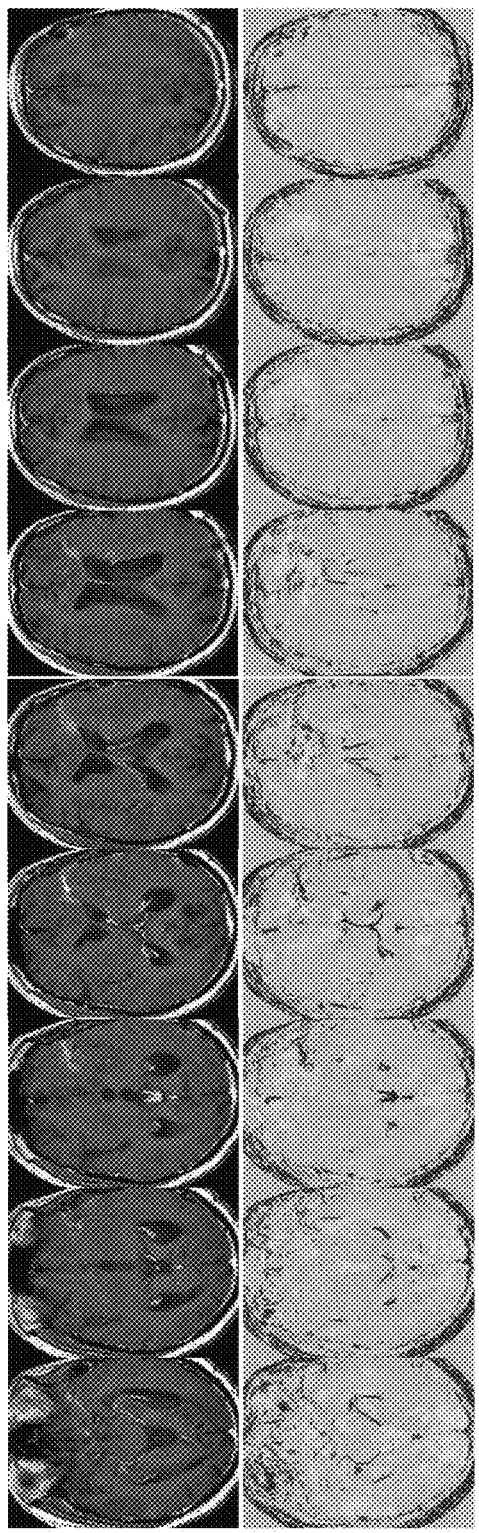
Figure 31:
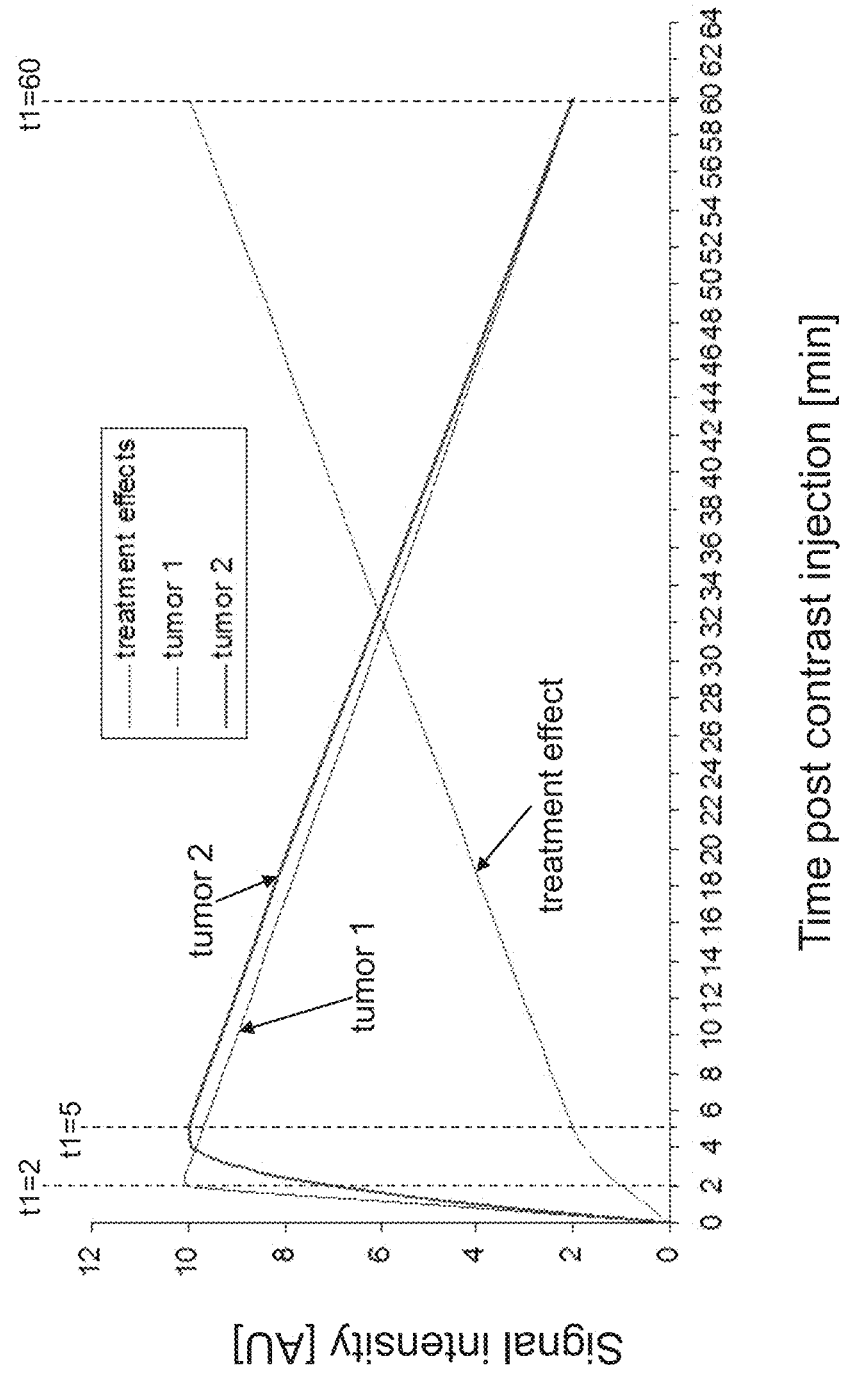

FIG. 15 illustrates 2D MRI scanning and maps acquired 1 months and three months after a second resection in the tumor patient of example 9 indicating that most of the tumor has been removed 1 month after the surgery but recurrence was detected 3 months post surgery;

FIG. 16 shows 2D conventional MRI and mapping left, and 3D conventional and mapping right of the same patient as in FIG. 15, with the 3D mapping clearly showing that the tumor has recurred;

FIG. 17 illustrates 2D and 3D conventional MRI and mappings according to the present embodiments of the patient of Example 10, with a brain metastasis of ovarian cancer, in which the overall tumor volume seen in the two maps is similar;

FIGS. 18A-18I show examples of application of the technique according to some embodiments of the present invention to patients with AVM;

FIG. 19 show examples of application of the technique according to some embodiments of the present invention to a child with an anaplastic chordoma;

FIGS. 20A and 20B show examples of application of the technique according to some embodiments of the present invention to a patient recruited after stereotactic radiosurgery of a chordoma with suspected radiation necrosis;

FIGS. 21A and 21B show examples of application of the technique according to some embodiments of the present invention to a patient after stereotactic surgery treatment of anaplastic meningioma;

FIGS. 22A-D show examples of application of the technique according to some embodiments of the present invention to a patient previously diagnosed with a low grade non-enhancing glioma in the brain stem and spine;

FIGS. 23A and 23B show examples of application of the technique according to some embodiments of the present invention to a patient after surgical removal of a hypofisal adenoma;

FIGS. 24A and 24B show examples of application of the technique according to some embodiments of the present invention to a patient with petroclival meningioma after stereotactic radiosurgery (SRS);

FIGS. 25A-B show examples of application of the technique according to some embodiments of the present invention to rats with CNS1 glioma;

FIG. 26A-D show examples of application of the technique according to some embodiments of the present invention to dogs with spontaneous glioma;

FIG. 27A-B show examples of application of the technique according to some embodiments of the present invention to mice with U87 (human) glioma;

FIGS. 28A and 28B show examples of application of the technique according to some embodiments of the present invention to a patient having malignant melanoma diagnosed with a bleeding lesion in the brain;

FIGS. 29A and 29B show examples of application of the technique according to some embodiments of the present invention to a patient cerebellar metastasis of breast cancer after stereotactic radiosurgery;

FIGS. 30A and 30B show examples of application of the technique according to some embodiments of the present invention to a patient with GBM after 2 resections and treatment with chemoradiation; and FIG. 31 shows estimated signal intensity (in arbitrary units) as a function of the time after injection of contrast agent for signals corresponding to two tumors, and for a signal corresponding to a treatment effect.

DESCRIPTION OF SPECIFIC EMBODIMENTS OF THE INVENTION

The present invention, in some embodiments thereof, relates to method and apparatus for producing magnetic resonance (MR)-based maps and, more particularly, but not exclusively to using such maps to identify and study tumors.

The present embodiments can be applied to any MR image of any part of the body, including, without limitation, brain, colon, prostate, bladder, breast, chest, lung, liver, bones and bone marrow, ovary, kidneys, spleen, thyroid gland, pancreas, head and neck, extremities, skin, lymph nodes, brain, colon, prostate, breast, lung, liver, bones and bone marrow, ovary, pancreas, head and neck, skin, abdomen, eyes, heart, stomach. The present embodiments are particularly useful for analyzing tumors or tissues which are suspected as tumors.

The present embodiments provide an MRI-based methodology providing high resolution maps with clear differentiation between tumor and non-tumoral tissues in patients having one or more tumors, unattainable by current imaging methods. This enablement system is based on delayed contrast extravasation MRI.

The present embodiments are useful also the analysis of tissues in subjects having a cancer or subjects being suspected as having a cancer. Typically, the cancer is of a solid tumor cancer. Representative examples of solid tumor cancers for which the technique of the present embodiments is applicable, include, without limitation, brain tumors, Ewing sarcoma, Head and neck tumors, lung cancer, colon and rectum cancer, breast cancer, prostate cancer, urinary cancer, uterine cancer, bladder cancer, oral cancer, pancreatic cancer, stomach cancer, ovarian cancer, liver cancer, laryngeal cancer, thyroid cancer, esophageal cancer, lymphomas, leukemias, and testicular cancer. The present embodiments are useful for the analysis of tissues in subjects having primary tumors, secondary tumors, metastatic tumors, intra-cranial tumors and extra-cranial.

While the embodiments below are described with a particular emphasis to brain tumors, it is to be understood that more detailed reference to brain tumors is not to be interpreted as limiting.

In various exemplary embodiments of the invention two sets of MR images are acquired. A first set of MR images is taken such that the MR scan begins t1 minutes after injection of contrast agent, and a second set of MR images is taken such that the MR scan begins t2 minutes after injection of contrast agent, wherein t1 is at least 2 and preferably less than 20, and the difference t2-t1 is at least 20, optionally and preferably at least 60, optionally and preferably less than 120. For example, t1 can be from about 3 to about 20, or from about 3 to about 15, or from about 3 to about 10, or from about 4 to about 10, or from about 5 to about 10, or from about 3 to about 7, e.g., about 3 or about 4 or about 5 or about 6 or about 7 or about 8 or about 9 or about 10; and t2 can be from about 60 to about 120, or from about 60 to about 105, or from about 65 to about 85, or from about 70 to about 80, e.g., about 70 or about 75 or about 80. Each measurement typically requires from about 2 to about 6 min of MR scanning, and the subject can be allowed to exit the MR scanner between the two time points.

The MR images are then used to calculate maps clearly depicting tumoral regions in one color (for example, blue) and non-tumor regions (including treatment effects, inflammatory-related pathological and, in case of brain MRI, other types of non-tumoral BBB disruption) in a different color (for example, red), based on their contrast accumulation or clearance patterns. The images can be acquired on any clinical MR scanner using the conventional type/dose of contrast agents and the resulting maps provide high resolution depiction of the tissues with an easy to interpret color code. Data analysis is model-independent and optionally and preferably comprises image pre-processing (for overcoming acquisition-related artifacts) and subtraction of the early images (acquired t1 minutes post contrast injection) from the late images (acquired t2 minutes post contrast injection).

A map can be constructed for the same subject more than once, wherein each such map is constructed by subtracting an MR scan taken t1 minutes after injection of contrast agent from an MR scan taken t2 minutes after injection of contrast agent. For example, a first map can be constructed before a treatment and a second map can be constructed after a treatment, so as to assess the effect of the treatment.

The assessment of the effect of the treatment can include, but is not limited to, assessing the responsiveness of the tumor to the treatment (e.g., whether the size of the tumor has changed), distinguishing between an active tumor and a tissue region which is not a tumor but which is abnormal, for example, due to treatment effects, assessing tumor progression or lack thereof, assessing tumor pseudo-progression, assessing whether there is residual tumor after treatment. The maps of the present embodiments can also be used to detect tumors within bleeding regions.

The maps can be used to assess the effect of any therapy employed for the purpose of affecting, decreasing or eliminating a tumor or any other pathology, including, without limitation, arteriovenous malformation (AVM), such as, but not limited to, pelvic AVM, kidney AVM, liver AVM, spinal AVM, brain AVM, and pulmonary AVM. For example, the therapy can comprise chemotherapy, such as a drug, and/or a radiation-based therapy. The therapy can include a second therapeutic agent, such as a gene-specific or non-gene-specific therapeutic agent, such as an siRNA, antisense RNA, triple helix RNA, ribozyme, antibody, or small molecule inhibitor. The therapy can comprise at least one of chemotherapy, a ionizing radiation therapy, a radiation therapy, a focused radiation therapy, radiosurgery, gamma-knife therapy, intensity modulated therapy, a physical therapy, a thermal therapy, an electrical therapy, an electromagnetic therapy, a radiofrequency therapy, an ultrasound therapy, focused-ultrasound therapy, Transcranial magnetic stimulation, electroporation therapy, laser therapy, cryognic therapy, anti-angiogenic therapy, immuno-therapy, genetic-based therapy, therapy based on convection-enhanced delivery. The therapy can comprise a proliferation based therapy. Non-limiting examples of proliferation based therapies include an alkylating agent, a nitrosourea, an antimetabolite, an anthracyclin, a topoisomerase II inhibitor, spindle poison, and a mitotic inhibitor. Any combination of two or more of the above therapies with or without an additional therapy other than any of the above therapies is also contemplated.

When more than one map is constructed for the same subject, for example for the purpose of assessing response to treatment over a period of several weeks, months or years, the time t1 is preferably approximately the same (with a tolerance of up to 2 minutes, more preferably up to 1 minute, more preferably up to 30 seconds) for all the maps that are constructed for the subject. The time t2 can be the same or different as desired but preferably at least 60 minutes after t1. The differences between the t2 times among maps of the same subject can be from 0 minutes to 50 minutes. For example, before treatment t1 can equal 5 minutes and t2 can equal 60 minutes, and after treatment t1 can equal 5 minutes and t2 can be at least 70 minutes or at least 80 minutes or at least 110 minutes.

A map can optionally and preferably be constructed for the same subject, for the same MRI exam, more than once, using three or more MRI series. For example, two or more values of the time t1 can be employed, wherein a separate map is constructed for each value of the time t1. As a representative example, a series of MR images can be taken such that the scan begins t1(0) minutes after injection of contrast agent, another series of MR images can be taken such that the scan begins t1(1) minutes after the injection of the contrast agent, and an additional series of MR images can be taken such that the scan begins t2 minutes after injection of contrast agent, where t1(0) is less than t1(1), and t1(1) is less or equals t1 as defined above, for example t1(0) can be less than 3, e.g., 2, t1(1) can be from about 3 to about 20, e.g., 5, and t2 can be at least 60 but less than 120. From these three series, two maps can be constructed. A first map can be constructed by subtracting the series corresponding to t1(0) from the series corresponding to t2, and a second map can be constructed by subtracting the series corresponding to t1(1) from the series corresponding to t2. It was unexpectedly found by the present inventors that the first map is more accurate for determining locations of non-tumoral regions and the second map is more accurate for determining locations of tumoral regions. Optionally, a third map is also constructed by combining the information of both maps. Preferably the non-tumoral regions of the third map are extracted from the first map and the tumoral regions of the third map are extracted from the second map.

In some embodiments of the present invention the subtraction maps are blood vessel function maps.

The present inventors validated the obtained maps histologically by comparing the pre-surgical maps with histological samples acquired from 51 lesions obtained from 47 patients with primary and metastatic brain tumors (first 20 patients listed in Zach et al, PLOS One 2012). In most cases regions marked on the maps as tumoral regions were determined to consist of morphologically active tumor and regions marked on the maps as non-tumor regions were histologically found to be non-tumor abnormal tissues. Taking into account all histological samples the sensitivity was found to reach 99% and the positive predictive value 95%. The maps optionally and preferably may thus be used for clinical decisions.

Preferably, a T1-weighted MRI pulse sequence is employed. In some embodiments of the invention, the MR scan employs a pulse sequence of a type known as 3D MR. A representative example of a 3D MRI technique suitable for the present embodiments include, without limitation, fast spoiled prepared gradient echo.

The advantage of using 3D MRI is that higher resolution can be achieved (important both for correct interpretation of the patient status as well as for high precision treatment planning) and the 3D information allows the physician to observe the pathology from any angle. In some embodiments a 1 mm$^3$ resolution is used, compared to 5 mm slice resolution in 2D MRI.

Successfully using t1 which is about 5 minutes or more, but preferably not more than 10 minutes was a surprise. Previous work described herein uses t1=2 minutes, since the time is measured from the administration of contrast agent, and given that the signal rise in the blood vessels is fast, the working assumption would be to take the first image as soon as possible.

When studying the dependence of the signal rise on the time post contrast injection for different regions in the pathological areas, it was unexpectedly found that, on average, tumor tissues reach peak signal intensity at different and longer times than normal blood vessels. Without wishing to be bound to any particular theory, the present inventors provides the following explanation for the discovered surprising effect.

Leakiness of the blood vessels causes ongoing accumulation of contrast agent in the tissue. Therefore, the signal intensity of tumor tissues for t1 which is, for example, 10 minutes may reach higher values that that of 2 min, resulting in a larger absolute difference between t2 and t1, thus increased sensitivity to tumoral tissues. On the other hand, the sensitivity to treatment effects may be reduced since the signal of these types of tissues also rises between 2 and 10 minutes post contrast injection, thus reducing the absolute difference between t2 and t1.

FIG. 31 shows an estimated signal intensity (in arbitrary units) as a function of the time after injection of contrast agent for signals corresponding to two tumors (referred to in FIG. 31 as tumor 1 and tumor 2), and for a signal corresponding to a treatment effect. As shown, the treatment effects signal intensity keeps rising throughout the 60 minutes post contrast, the signal intensity of tumor 1 increases fast and then decreases fast, and the signal intensity of tumor 2 increases fast, but slower than tumor 1. In this example, for t1=2 min, the difference in signal intensity of the treatment effects between the two time points is 8.5, of tumor 1 is 8 and of tumor 2 is 5. For t1=5 min, the difference in signal intensity of the treatment effects between the two time points is 7 (thus decreased sensitivity than for t1=2 min), of tumor 1 is 7.7 (similar that of t1=2 min) and of tumor 2 is 8 (increased sensitivity than for t1=2 min).

It was found by the Inventors of the present invention that, as discussed above, by acquiring late MRI data up to twenty or more minutes, up to 60 or more minutes, or up to 75 min post contrast administration, or even up to 90 minutes or more, or even up to 100 minutes or more, or even up to 120 minutes or more, can add unique information regarding the late contrast clearance or accumulation component. Calculated maps of these unique enhancement and clearance characteristics were found to provide a clear distinction between tumor and non-tumoral tissues with high resolution and high sensitivity to subtle blood brain barrier disruption.

The current standard of care for newly diagnosed glioblastoma multiforme (GBM) is resection, when possible, followed by radiotherapy with concomitant and adjuvant temozolomide. Pseudoprogression is a radiographic term referring to early increase in enhancement seen post treatment with improvement/stability after a couple of months. Conventional MRI is currently unable to differentiate between tumor progression and pseudoprogression. Since the treatment depends greatly on this question, reliable distinction between the two conditions is crucial.

The methodology is based on delayed contrast extravasation MRI for calculating subtraction maps depicting unique characteristics with high resolution and high sensitivity to subtle blood brain barrier disruption. These maps provide clear depiction of tumor and non-tumoral components of enhancing GBM lesions.

In applicant's earlier work, twelve GBM patients undergoing standard chemoradiation were recruited and scanned by MRI three weeks after chemoradiation and every two months thereafter. Subtraction maps were calculated from high resolution MR images acquired up to 75 min after contrast administration. Two primary populations were determined: A slow population, in which contrast accumulation in the tissue was slower than contrast clearance, and a fast population in which clearance was faster than accumulation. Stereotactic biopsy samples confirmed the fast population to consist of morphological active tumor and the slow population to consist of non-tumoral tissues.

The volumes/intensities of the fast population were doubled when increasing the delay from 15 to 75 min suggesting increased sensitivity to tumor tissues at longer delays.

Significant correlation found between the maps and conventional contrast-enhanced MRI suggest that on average 50% of the enhancing lesion on conventional MRI does not represent morphological active tumor. The application for prediction of response to therapy was demonstrated by significant correlations between initial vessel function values and later tumor volumes on conventional MRI. Only one patient within this cohort showed no blue component in any of his images. This patient is currently progression free for three years after chemoradiation.

Subtraction maps based on the above-mentioned delays enable high resolution differentiation between tumor and non tumoral tissues. The information provided allows for appropriate patient management, both in deciding whether to operate on a patient with radiologic deterioration, continue chemoradiation or change to a second line non-surgical treatment. The present maps may also be applied for planning resection in the most efficient and safe manner and for early prediction of response to therapy, thus enabling selection of patients susceptible to benefit from the treatment.

The application of the maps of the present embodiments for routine patient monitoring, exposes new patterns of response, even to known therapies (moreover for new therapies), since the maps allow depiction of the real tumor burden and thus changes in the tumor in response to therapy. For example, the term pseudoprogression was realized in the last few years and in various papers authors refer to pseudoprogression as a separate condition of pure treatment effects. In a cohort of 39 patients with primary brain tumors recruited post chemoradiation to a study performed according to some embodiments of the present invention no a patient with pure treatment effects has been observed. The present inventors have thus concluded that such conditions are rare. Two of the patients were recruited with no residual tumor post surgery (no blue component in the maps) and they are currently disease free and under follow-up nearly 1 and 3 years post chemoradiation. Either than those, all the other 37 patients, even those showing significant treatment effects in the maps, showed some component of active tumor throughout their follow-ups. The ability to easily differentiate tumor from non-tumoral tissues enabled the technique of the present embodiments to determine the pattern of pseudoprogression as significant increase in the non-tumoral component (e.g., red region on the map), with a stable, (or slower increase or decrease of the), tumor component (e.g., blue region on the map). Using the maps the present inventors found that progression is characterized by increasing blue/tumor volumes (while lesion volume on contrast-enhanced T1-MRI does not necessarily change) and response to treatment is characterized by stable or decreasing blue/tumor volumes. These clear observations were not attainable without the high resolution reliable differentiation between tumor and non-tumoral tissues provided by the maps. In the case of brain metastases, we have learned that even when a component of morphologically active tumor exists in the maps, it can be stable for long periods (up to 9 months in our cohort of 53 recruited patients) enabling postponing resection till increase in the blue/tumor volume is noticed.

Due to improved treatment protocols and extended survival radiation-induced neuro-toxicity of patients with tumors undergoing radiation-based therapies has become a major concern and efforts to minimize unnecessary exposure of surrounding normal tissue without compromising treatment efficacy are of increasing interest. The ability of our maps to depict morphologically active tumor regions with high resolution may thus be applied for accurate radiation treatment planning by localizing the treatment to the tumor/blue regions in our maps thus enabling efficient treatments with minimum toxicity to normal surrounding tissues.

The maps of the present embodiments can be used for guiding a local treatment of tumor. The local treatment is optionally and preferably at a spatial resolution of less than 5 mm, more preferably less than 2 mm, more preferably 1 mm or less. The spatial resolution of the treatment refers to the accuracy of the treatment tool, and not necessarily to the size of the treated region. In a representative example, the maps of the present embodiments are loaded onto the navigation systems in the operating room for accurate targeting of invasive procedures such as guided biopsies, surgeries and implantation of treatment devices. The maps of the present embodiments can also be loaded onto radiation-based treatment planning workstation for accurate targeting of radiation-based treatments such as, but not limited to, intensity modulated radiotherapy, radiosurgery and gamma-knife treatments.

An increasing concern regarding radiation injury, hampers the option of applying high dose radiation treatment to the surgery site after resection of metastases. A further application of the maps optionally and preferably can be to differentiate residual tumor from post surgery changes, thus allowing selecting patients who will benefit from post surgery radiation and use the maps for targeting the treatment only to regions of residual tumor.

The present embodiments are also useful also for improving patient management, for example, by differentiating tumor progression from treatment effects, of any type of solid tumor.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1A:
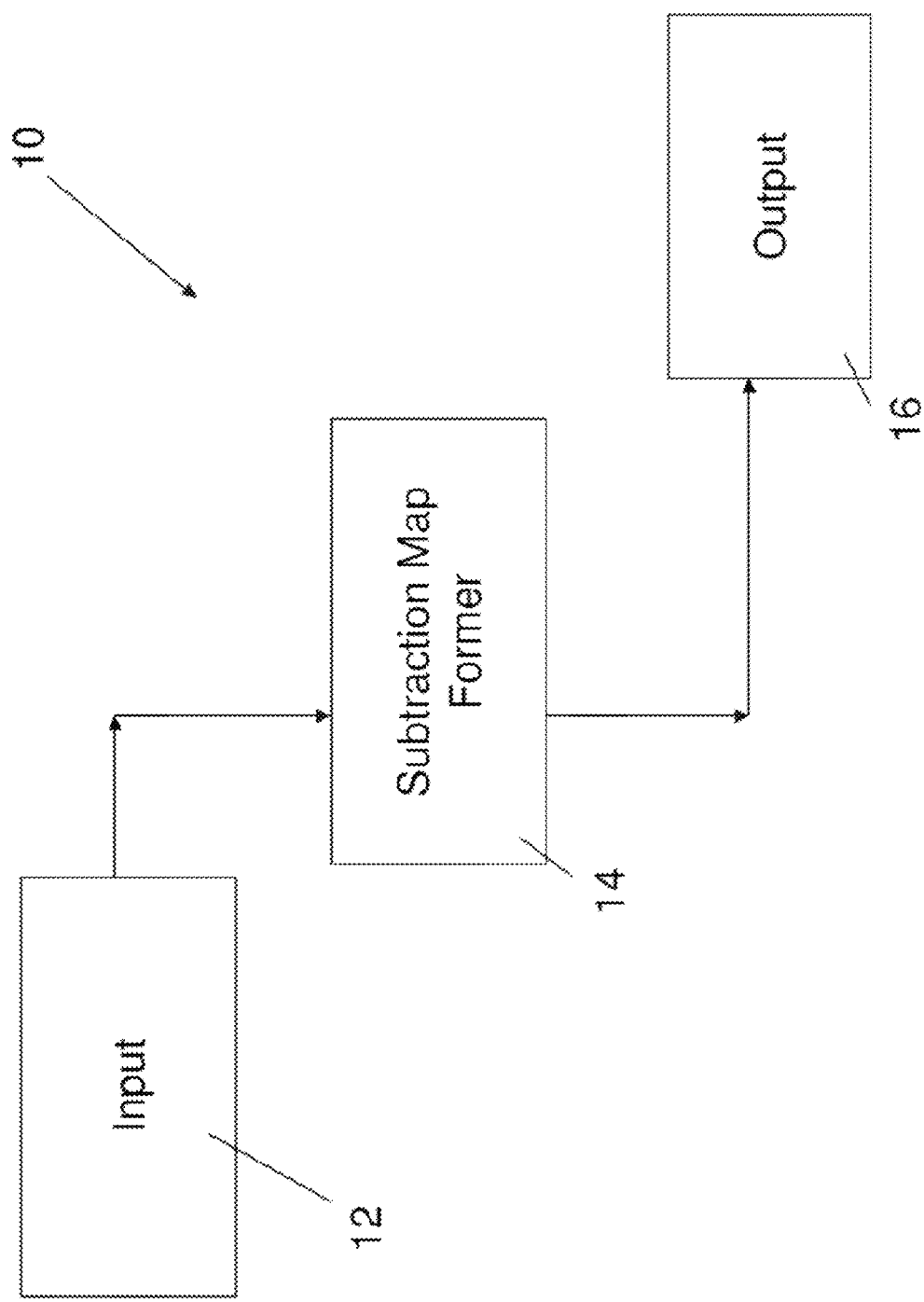
FIG. 1A is a simplified block diagram showing imaging apparatus for producing subtraction maps according to applicant's earlier application.

Reference is now made to FIG. 1A which illustrates apparatus 10 for analyzing tissue, such as, but not limited to, brain tissue, comprising an input 12 for receiving a first and a second MRI series at the beginning and end of a predetermined time interval, and a subtraction map former 14. The subtraction map former forms a subtraction map from the two MRI series by analyzing the series to distinguish between two primary populations, a slow population, in which contrast clearance from the tissue is slower than contrast accumulation, and a fast population in which clearance is faster than accumulation. An output 16 provides an indication of distribution of the two primary populations. In the present embodiments, the time period between the two series is at least twenty minutes. The time period may additionally exceed thirty minutes, or even forty minutes, or fifty minutes, or sixty minutes, or seventy minutes, or eighty minutes, or ninety minutes, or a hundred minutes. Specifically, time periods used may be seventy minutes, or seventy five minutes or ninety minutes.

Figure 1B:
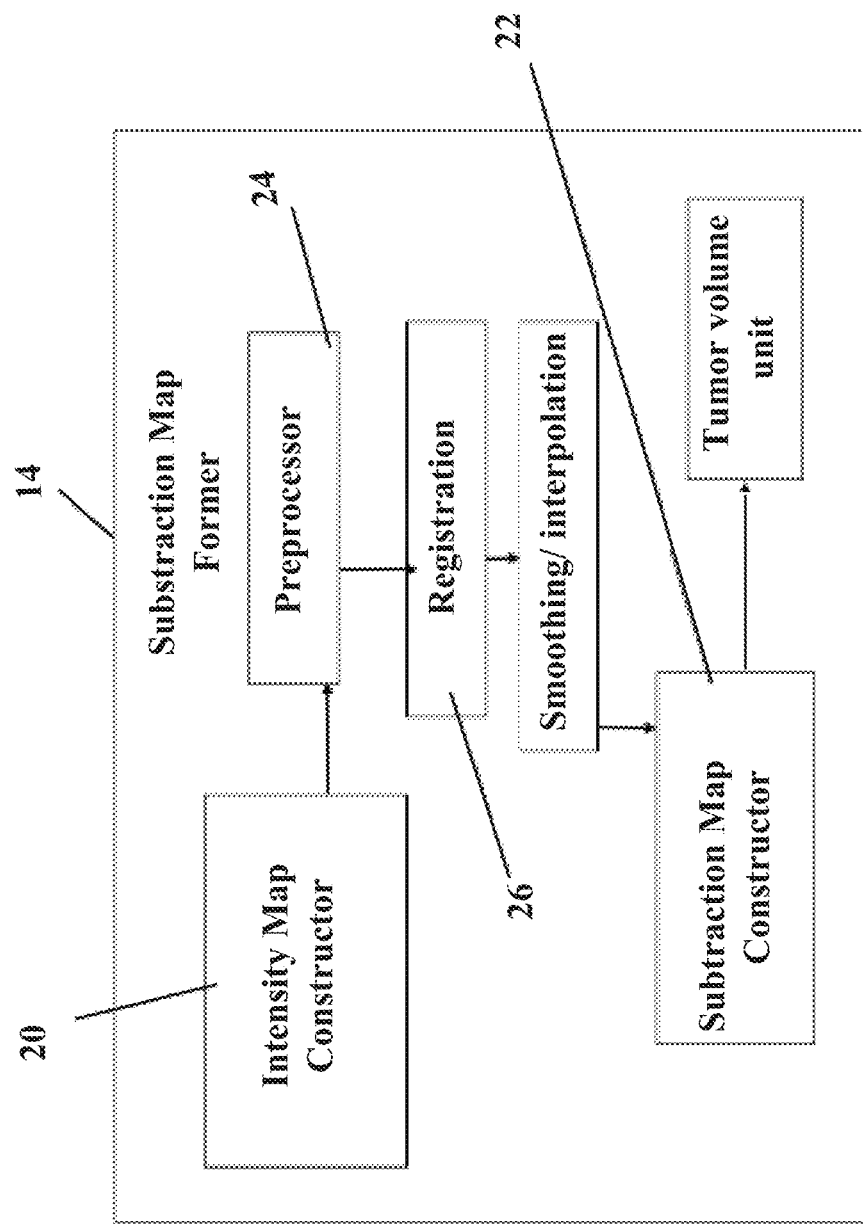
FIG. 1B is a simplified block diagram showing the subtraction map former of FIG. 1A in greater detail.

Reference is now made to FIG. 1B which shows the subtraction map former of FIG. 1A in greater detail. The subtraction map former includes an intensity map constructor 20 for constructing, for each magnetic resonance image, an intensity map. A subtraction map constructor 22 constructs a subtraction map describing variations in concentration of the contrast agent in the tissue under analysis by detecting dissimilarities among a pair of intensity maps.

The subtraction map former 14 may assign a representative intensity value for each magnetic resonance image and determining a time-dependence of the representative intensity value.

The subtraction map former may generate a graph describing the time-dependence.

The input 12 may typically use high resolution 2D or 3D T1-weighted MR images (T1-MRIs).

The subtraction map former may use the subtraction map to assess whether tumor tissue is present or whether what appears to be tumor tissue is mere treatment effect, by comparing drainage of the contrast agent versus contrast agent take up.

The image may be pre-processed at preprocessor 24, prior to subtraction. Preprocessor 24 can includes a circuit and computer readable medium storing instructions to be carried by the circuit for preprocessing the image. The preprocessing may involve at least one of:

a) correction for intensity variations; and
b) image registration.

Correction for intensity variations may comprise calculating, for each MR image separately, an intensity variation map consisting of large scale intensity variations therein and then subtracting the intensity variation map from the respective image.

A registration unit 26 carries out registration between corresponding MR images. Registration unit 26, can be, for example, a dedicated circuitry. Registration may comprise a rigid registration or alternatively an elastic registration, to allow for head movements between the two series.

Elastic registration may comprise dividing each slice of a respective series into to a grid of volumes, and allowing each volume to move freely in three dimensions until a sum of the absolute values of the intensity difference between the two time points reaches a minimum. A three-dimensional translation matrix is generated to match between the two images.

Figure 1C:
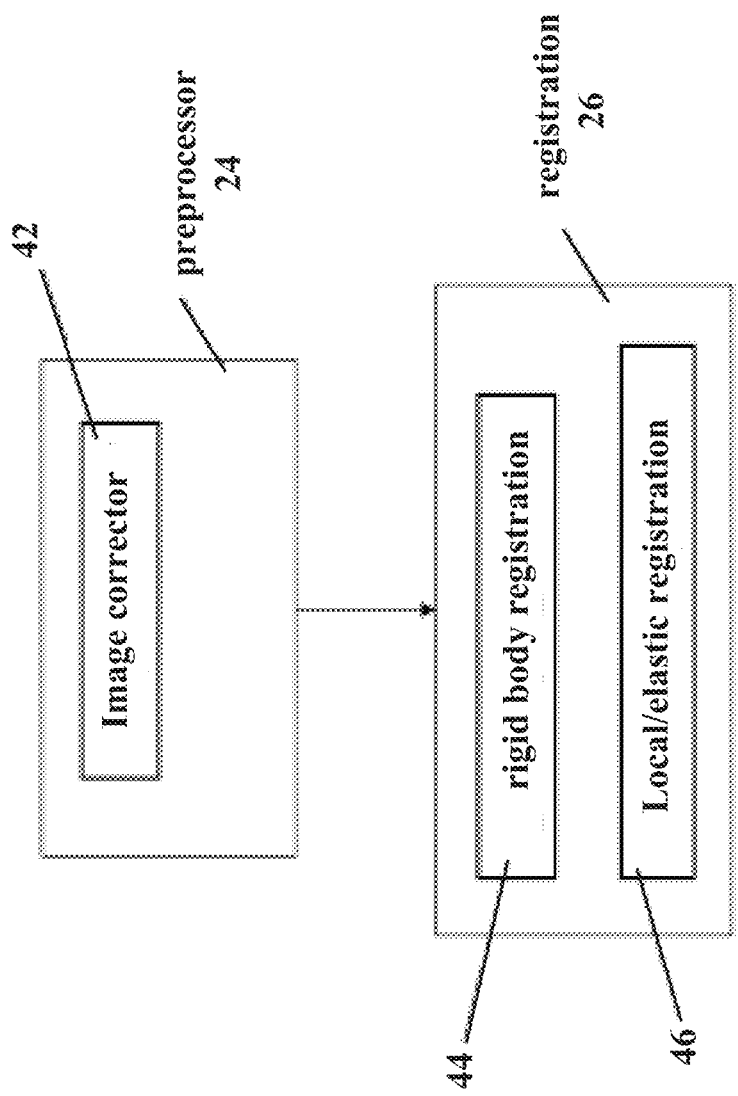
FIGS. 1C and 1F are simplified block diagram showing registration unit and image corrector.
Figure 1D:
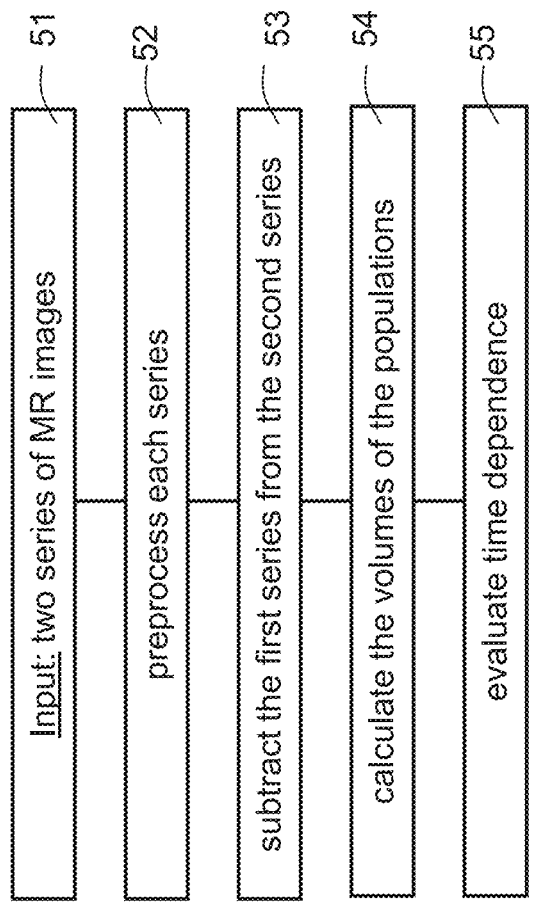
FIGS. 1D and 1E are flowchart diagrams describing a procedure for constructing subtraction maps, according to applicant's earlier application.
Figure 1E:
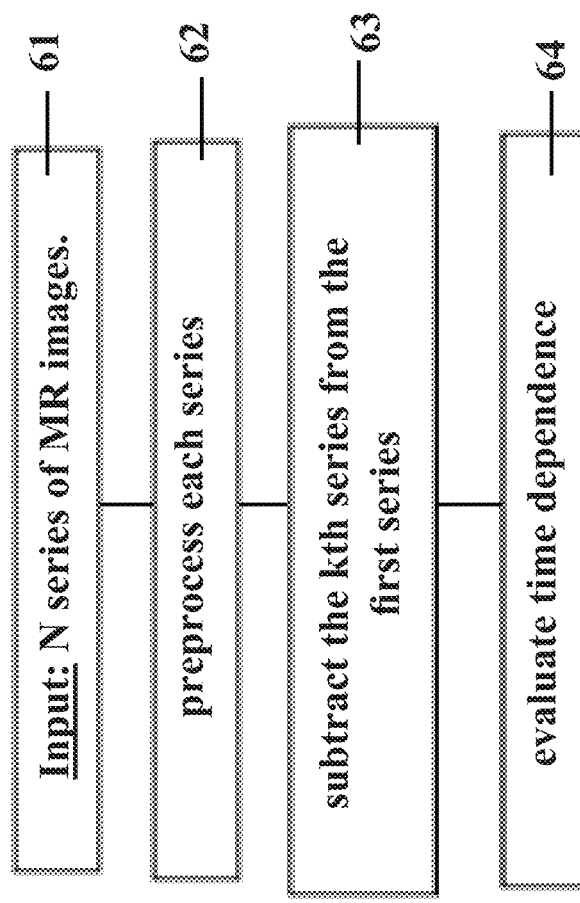
Figure 1F:
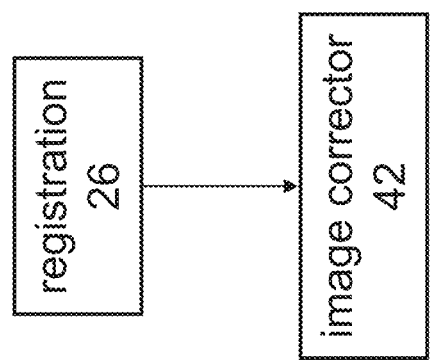

FIGS. 1C and 1F are simplified block diagram showing registration unit 26 and image corrector 42 in greater detail. Preprocessor 24 optionally and preferably comprises an image corrector 42 which performs intensity correction on each image of the MR images. This can be done by calculating an intensity variation map consisting of the large scale intensity variations. In various exemplary embodiments of the invention the map is then subtracted from the original image resulting in a flattened image.

The flattened image is transmitted from image corrector 42 to registration unit 26. In some embodiments, preprocessor 24 is configured to apply the intensity variation correction to the registered images. In these embodiments image corrector 42 receives the images from registration unit 26, as schematically illustrated in FIG. 1F.

Registration unit 26 optionally and preferably comprises a rigid body registration unit or circuitry 44 and a local or elastic registration unit or circuitry 46.

Rigid body registration unit or circuitry 44 is preferably configured to apply a rigid body registration to the second MRI series in order to register it to the first MRI series. The rigid body registration can include, for example, a 6 parameter (rigid body) spatial transformation. The registration can optionally and preferably include execution of least square procedure. Local or elastic registration unit or circuitry 46 is preferably configured to apply elastic registration in order to register the second MRI series to the first MRI series to correct for distortions induced in the MRIs by the organ movements.

The registration optionally and preferably comprises statistical parametric mapping. Following is a preferred process for performing the registration according to some embodiments of the present invention. The process performs a global registration applied to a region-of-interest in the image. For example, when the MR images are brain MR images, a region-of-interest which is the brain can be defined, and the global registration can be a whole brain registration.

The process can optionally and preferably perform a procedure for increasing the spatial precision of the global registration. Preferably, a segmentation procedure is employed. Suitable segmentation procedure includes, without limitation, voxel-based morphometric procedure available within the MATLAB® software (The MathWorks, Inc. Natick, MA, U.S.A). A decreasing kernel width can be employed based on the segmentation. The decreasing kernel can optionally and preferably be of the type "Full Width Half Max" (FWHM). When the image includes a brain MRI, a decreasing kernel width with cerebral spinal fluid (CSF) weighting can be employed.

In various exemplary embodiments of the invention a local registration is applied following the global registration. The local registration is optionally and preferably applied to a sliding slab taken along a slice plane of the MRI. For example, the main MRI slice plane can be used. The size of the sliding slab can be fixed to a predetermined value. Alternatively a sliding slab having a varying size can be employed. A typical size of a sliding slab according to some embodiments of the present invention is from about 0.5 cm to about 2 cm, e.g., about 1 cm. Such sizes can be used as fixed sizes for a fixed size sliding slab or as initial or average sizes for a varying size sliding slab. In some embodiments of the present invention the process performs a procedure for increasing the spatial precision of the local registration. This procedure can be similar to the procedure described above, except that it is applied to the sliding slab instead of the whole region-of-interest.

A smoothing and interpolation unit 28 may be located after the registration unit. Smoothing and interpolation unit 28 can be, for example, a dedicated circuitry. The three-dimensional translation matrix resulting from the elastic registration may be smoothed using circular smearing, and then interpolated to obtain translation values per pixel.

The intensity variation correction performed by image corrector 42 may optionally and preferably comprise radiofrequency (RF) inhomogenity correction. The RF inhomogenity correction optionally and preferably sets the mean signal intensity of a region-of-interest (e.g., the brain, for brain MRI) within both registered images to the same value. The RF inhomogenity correction optionally and preferably comprises three-dimensional filtering applied to each of the registered images in order to obtain smoothed images that can be used for normalizing the non-corrected data. In some embodiments of the present invention, pixels or voxels located outside a region-of-interest of the image (e.g., the brain, for brain MRI) are assigned with synthetic intensity values. For example, these pixels or voxels can be assigned with the mean signal intensity of the region-of-interest before filtering.

The three-dimensional filtering can be of any type. Representative examples of filters suitable for the present embodiment include, without limitation, Gaussian filters, convolution filters, median filters, separable filters and non-separable filters. Typically, Gaussian filtering is employed.

In some embodiments of the present invention the processor applies a dynamic normalization to the images, preferably, once registered, more preferably once registered and corrected. The dynamic normalization defines the dynamic of the differentiating properties (e.g., colors) displayed by the map. The dynamic normalization optionally and preferably employs a procedure that automatically identifies pixels or voxels that are within non-vessel regions in the image and pixels or voxels within vessel regions in the image. The non-vessel regions can include any region in which no blood vessel has been identified. For example, for a brain MRI, a representative example of a non-vessel region is a region identified as white matter.

Once the regions are identified, a reference level and a strongest signal decrease (due to contrast clearance between time t1 and time t2) are determined. These values are then defined as a subtraction map reference value and a subtraction map negative span, respectively. The subtraction map negative span represents the lowest negative value within the map. A similar procedure can be employed to define a subtraction map positive span, which represents highest positive value within the map. The subtraction map reference value, the subtraction map negative span and the subtraction map positive span are then used to define the differentiating properties (e.g., colors) displayed by the map. For example, regions on the map for which the subtraction results in a negative value can be displayed in different color range than regions on the map for which the subtraction results in a positive value.

In use, an initial enhancing lesion portion may be determined from the first series, which would typically be made two to ten minutes after contrast injection, as further detailed hereinabove. A threshold is optionally and preferably determined from intensity distribution histograms of the enhancing lesion and surrounding regions and is applied to define narrower region-of-interests (ROIs) that include only enhancing portions of the lesion. The narrower ROIs are thus defined over an entire enhancing region in each slice.

A lesion volume unit 30 may count a number of pixels in the enhancing portions of the ROIs and to multiply by a volume represented by a single pixel to provide a resulting volume as a parameter for assessment of tumor response. The tumor volume unit can be, for example, a dedicated circuitry.

In various exemplary embodiments of the invention the enhancing volume is calculated from the first series, acquired at time t1. Within this ROI, a count of the pixels or voxels that correspond to tumoral regions (e.g., blue voxels) can be obtained and their sum can optionally and preferably be defined as representing the tumor volume. Thus, the enhancing volume can consist of both blue and red pixels or voxels. The blue pixels or voxels are optionally and preferably counted and are used for calculating the tumor volume while the red pixels or voxels are optionally and preferably counted and used for calculating the volume of treatment effects.

FIGS. 1D and 1E are flowchart diagram describing a procedure for constructing subtraction maps, according to some embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Referring to FIG. 1D, at 51, 2 series of MR images are obtained. A first series can be acquired soon after contrast administration and a second series can be acquired after a predetermined time period as further detailed hereinabove.

At 52, the tow series are preprocessed, for example, by applying registration and/or intensity correction as further detailed hereinabove. At 53, the pre-processed first series is subtracted from the pre-processed second series. At 54, the volumes of the various populations (such as, but not limited to, the slow and fast populations) that appear in the maps are calculated.

Optionally and preferably the subtraction maps are used during a longitudinal follow-up of a patient. In these embodiments a time dependence is evaluated (55) throughout the follow-up of the patient. For example, parameter calculated from the maps at different follow-up time points of a patient can be used for predicting and/or monitoring the response of the patient for treatment. For example, the change in blue volume between the first 2 follow-up time points of a patient can be used for prediction of time-to-progression.

In some embodiments of the present invention more than 2 series of MR images are obtained. A representative example of these embodiments is illustrated in FIG. 1E. Thus, at 61 N series of MR images are obtained. The first series is preferably acquired soon after contrast administration, as further detailed hereinabove. The additional N−1 are preferably acquired at various time points thereafter. At 62 each series is preprocessed as further detailed hereinabove. At 63, the pre-processed first series is subtracted from the pre-processed kth series (k>1). At 64, a time dependence can be evaluated. For example, the signal of each pixel (or some ROI) in the maps can be calculated as a function of time post administration. A mathematical fitting procedure can be applied so as to fit the time dependence to a mathematical model. The fit can then be used for extracting information from the temporal behavior signal. For example, the fit can be used to extract permeability of the blood vessel, tissue density, and the like.

An application of the present embodiments involves depiction of tumors, particularly but not necessarily brain tumors, after treatment with anti-angiogenic treatments and studying the mechanism of action and response patterns of anti-angiogenic drugs.

A further application involves depiction of tissue disorders, particularly but not necessarily brain disorders, after treatment with radiation-based treatments, for differentiation between disease progression and radiation necrosis.

A further application of the present embodiments allows for differentiation between progression of brain space occupying lesion (SOL) and treatment effects following radiosurgical treatment.

As mentioned above, the first scan can be taken between 2 and 10 minutes, more preferably at least 5 minutes but not more than 10 minutes, after contrast injection.

As further mentioned above, better resolution may be achieved, using 3D MRI, to effectively distinguish between progression and pseudoprogression of the tumor, where pseudoprogression is most likely to be related to effects of the treatment (surgery, radiotherapy and chemotherapy).

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. The following examples demonstrate how improved management of patients is made possible by use of the present embodiments.

In the Examples below, the maps of the present embodiments are presented in colors wherein morphologically active tumors are shown in blue and non-tumoral regions are shown in red.

Example 1

Figure 2A:
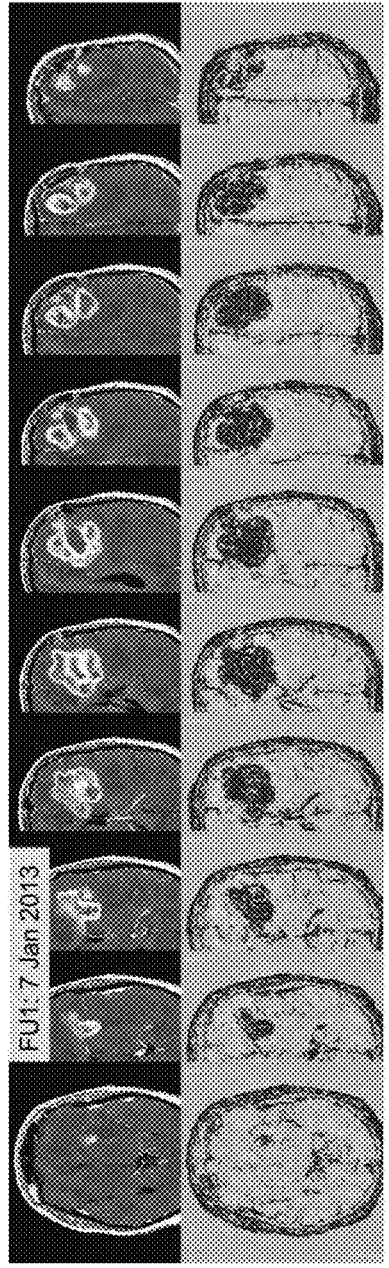
FIGS. 2A and 2B show conventional MRI and mapping according to the present embodiments, carried out on either side of a two and a half week interval on the patient of Example 1.
Figure 2B:
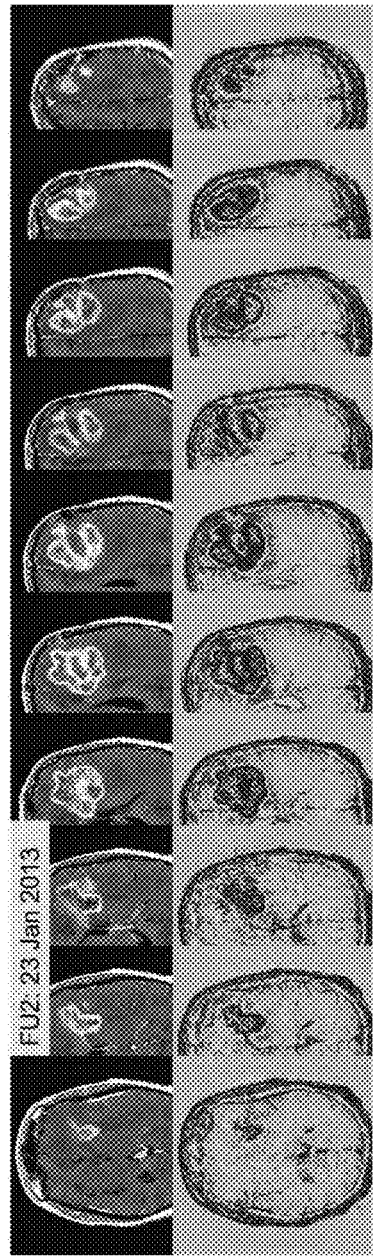

Referring now to FIG. 2A, an example of newly diagnosed GBM involves 49 year old male. The patient, with newly diagnosed GBM, underwent gross total resection at Sheba Medical Center followed by chemoradiation. The patient was recruited to the present study 1 week after chemoradiation with clinical deterioration. Conventional MRI showed a large partially enhancing lesion with low rCBV (FIG. 2A top). The maps (FIG. 2A below) showed that only part of the enhancing volume (on T1-MRI) consisted of morphologically active tumor (blue):

The patient was stabilized on steroids. The neuro-oncologist was determined to continue treatment with TMZ. The neurosurgeon was concerned surgery may be necessary. Referring now to FIG. 2B, the patient was rescanned 2.5 weeks later. Conventional MRI (including T1, T2, FLAIR, DWI and DSC PWI) showed no significant change. The maps (FIG. 2B below) showed significant increase in the active tumor volume with the addition of light blue regions surrounding the enhancing regions, suspected as infiltration of tumoral vasculature:

The patient underwent a second surgery 2 days later with results shown in FIGS. 3A-3H.

Figure 3B:
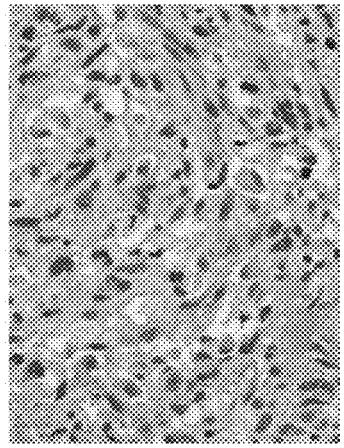
FIGS. 3A-3H show the histology of samples of the patient of Example 1 after surgery.
Figure 3D:
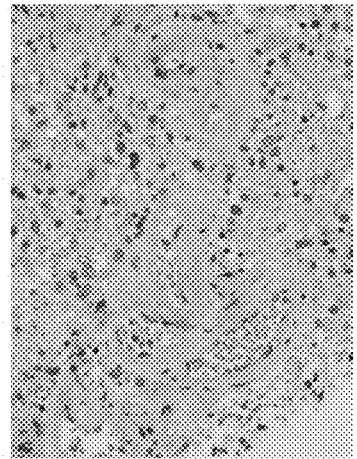
Figure 3A:
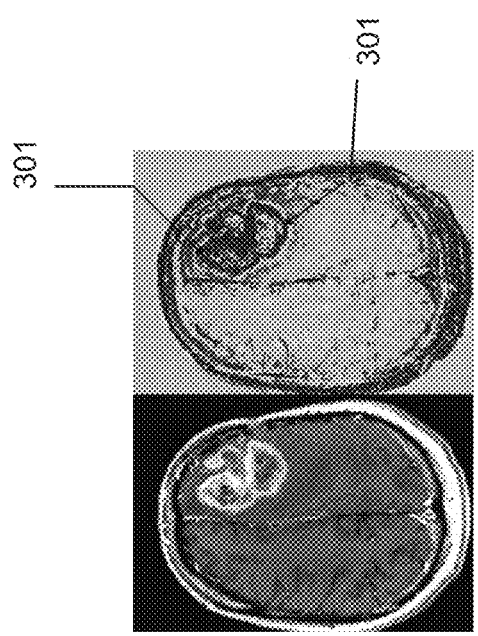
Figure 3C:
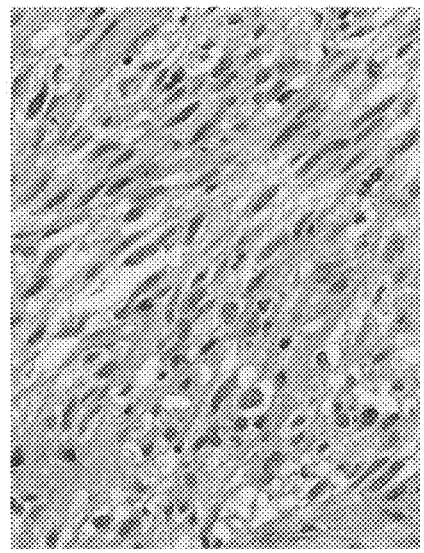
Figure 3F:
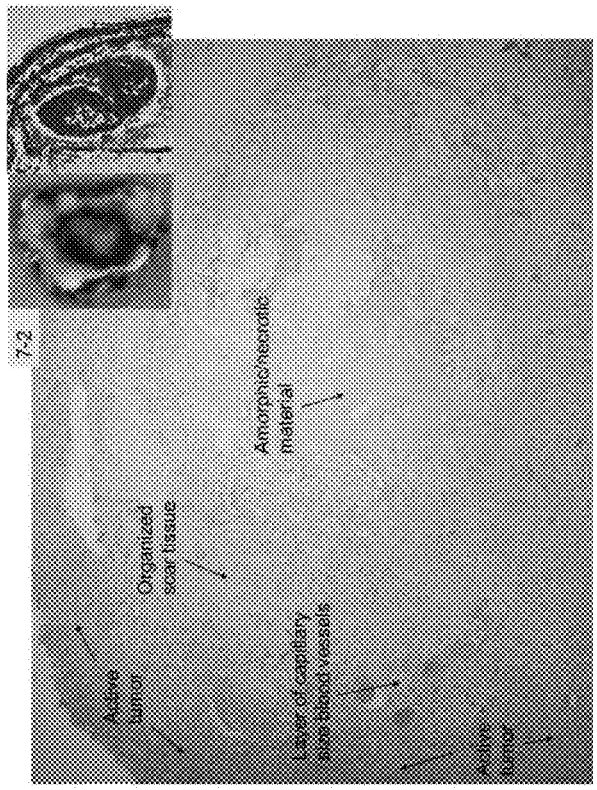
Figure 3H:
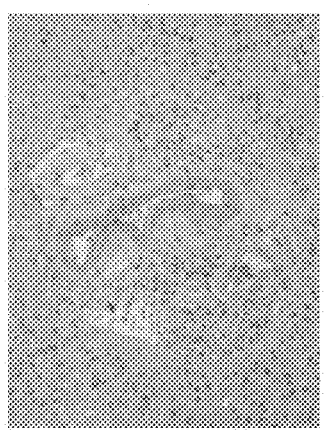
Figure 3E:
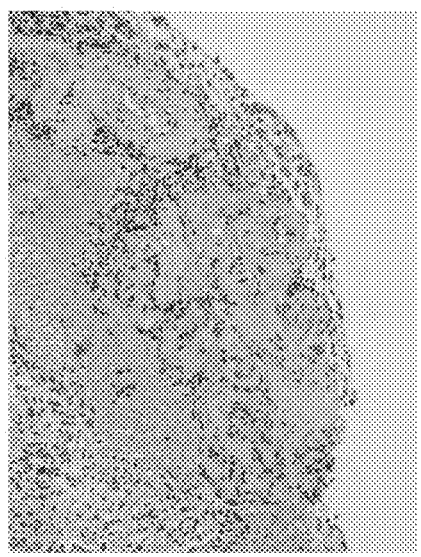
Figure 3G:
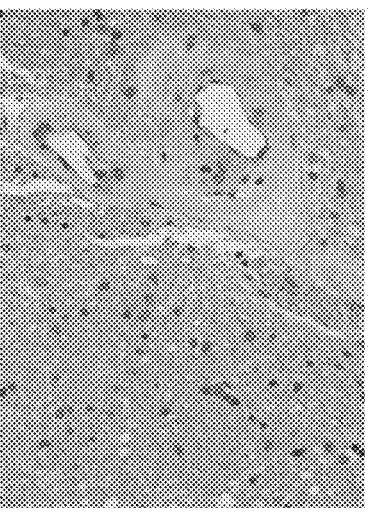

Histology of samples taken from various blue regions (see reference 301 in FIG. 3A) showed a highly cellular tumor in FIG. 3B. FIG. 3C shows some regions of splitting of cells, and the tumor was highly vascularized in many regions as seen in FIG. 3E.

In this patient significant light blue regions were depicted surrounding the enhancing region of the tumor (as seen in several previous cases). The only available histology of these regions has until now all been from a single patient. The histology shows infiltration of abnormal blood vessels in normal appearing brain surrounding the tumor. We believe this may be explained by abnormal vasculature in normal-appearing/infiltrative regions of surrounding brain. In this case part of the tumor was resected, showing the anatomy of the tumor and some of the surrounding brain tissue, as per FIGS. 3D and 3G.

Part of this tumor was resected en-block (FIG. 3F) showing the typical anatomy of the tumor, consisting of a necrotic center surrounded by a thick rim of morphologically active tumor, in excellent agreement with the calculated maps (top right).

Figure 4:
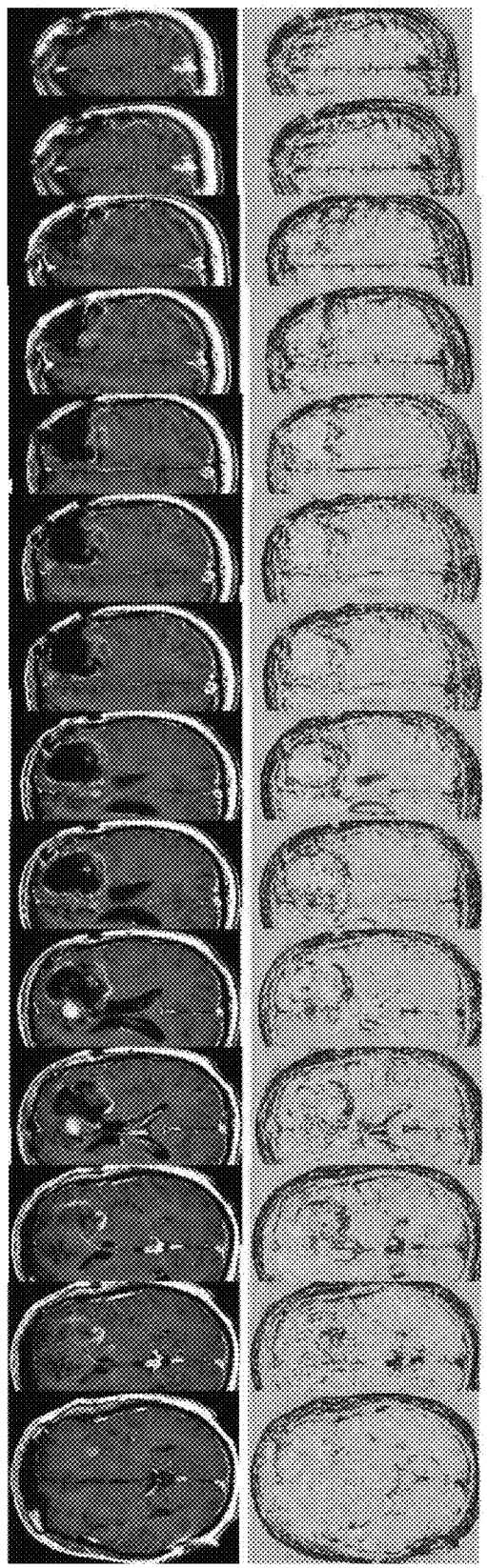
FIG. 4 is a one month post surgery MRI scan together with mapping according to the present embodiments, indicating success of the surgery and removal of the tumor in the patient of Example 1.

Referring now to FIG. 4, the patient was scanned 1 month post surgery and his maps showed the surgery was successful and most of the tumor was removed;

Example 2

Newly diagnosed GBM: A 50 year old male with newly diagnosed GBM underwent gross total resection at Sheba Medical Center followed by chemoradiation. 1 month after chemoradiation, increased enhancing volume was noted on contrast-enhanced T1-MRI with no clinical deterioration. PWI was inconclusive. The patient consulted with physicians at Sheba and Hadassah Medical Centers who could not advise whether he should be operated or continue TMZ treatment since they were unable to determine if the radiological deterioration was due to tumor progression or treatment effects. Referring now to FIGS. 5A-5E, the patient was recruited to our study and his maps (FIG. 5A bottom) showed significant volume of active tumor (blue) surrounding the previous surgery site:

Therefore, it was decided to re-operate on the patient.

Figure 5A:
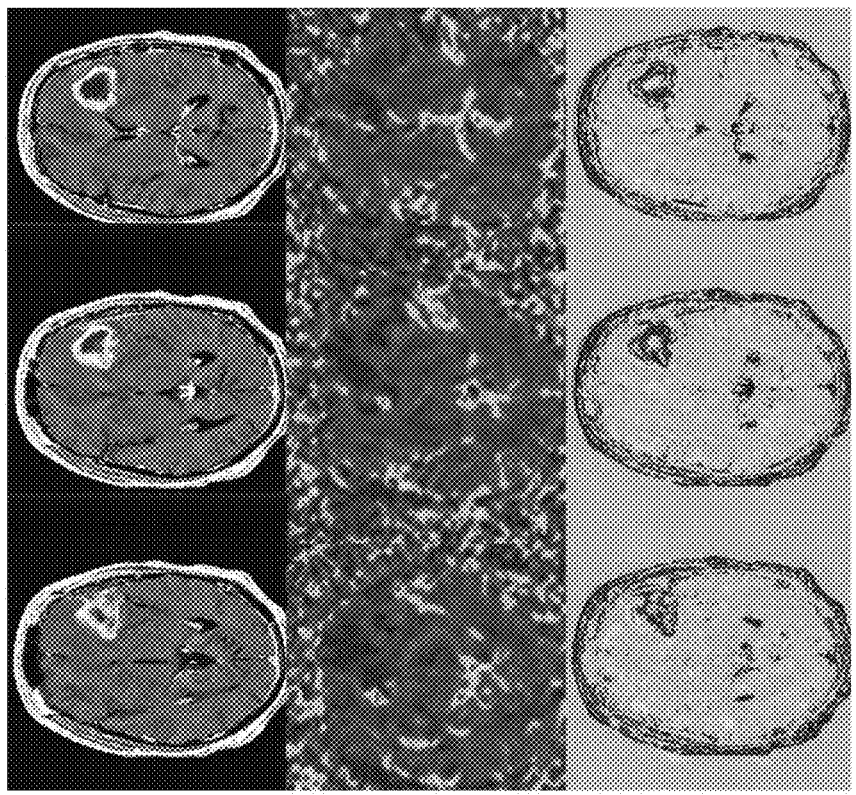
FIGS. 5A-5E are an initial MRI scan and mapping and histology samples for the patient of Example 2.
Figure 5C:
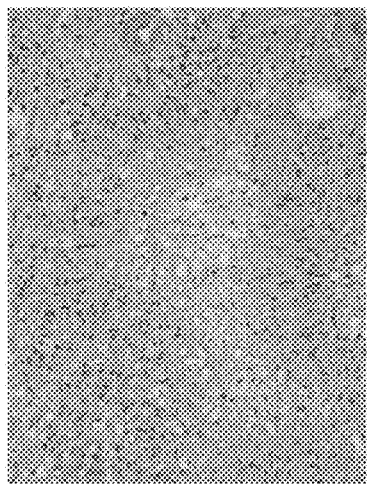
Figure 5E:
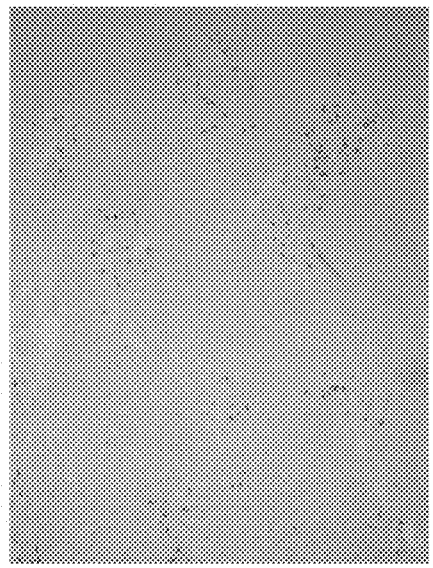
Figure 5B:
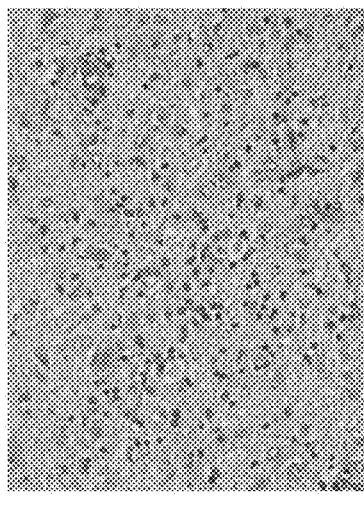
Figure 5D:
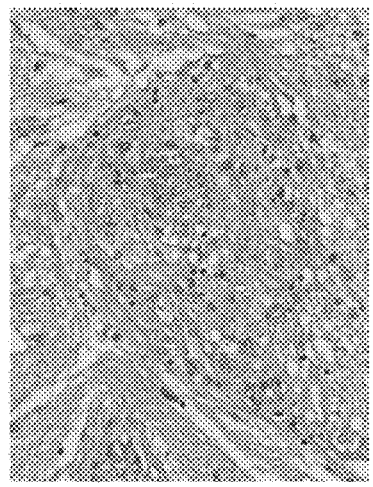

In this case, as per FIG. 5B, histology did not show a high density tumor and very little mitosis. But there were many clusters of small cells which raised suspicions of proliferation. FIG. 5C shows regions with palisading necrosis. As shown in FIG. 5D, these regions showed abnormal blood vessels such as the gulmeroloid vessel below.

Later staining of these regions with ki67 showed multiple foci of proliferating cells (8-10%) confirming the diagnosis of morphologically active tumor, as shown in FIG. 5E.

Figure 6:
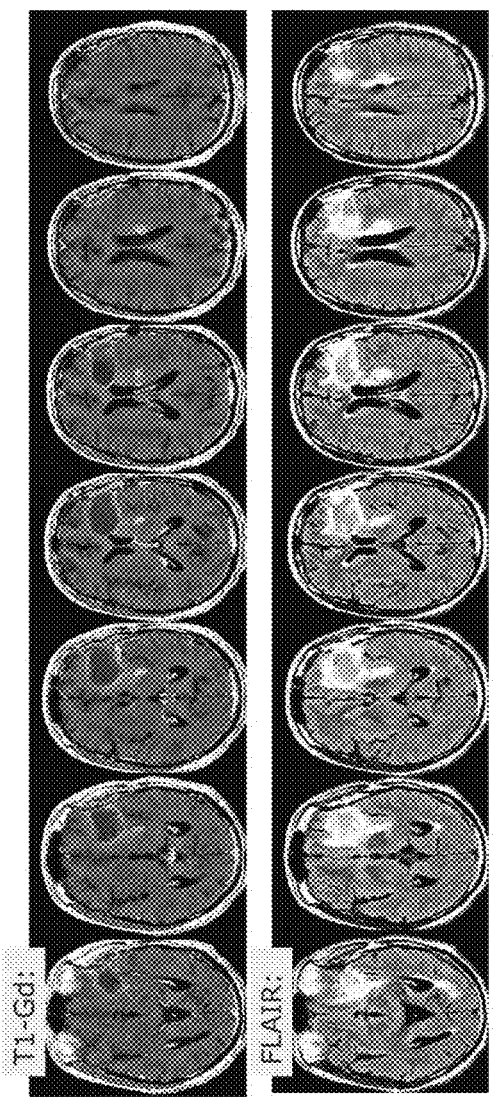
FIG. 6 is an MRI scan of the patient of Example 7 two weeks post surgery.

The patient was re-admitted to the hospital two weeks post surgery due to wound healing problems. Conventional MRI acquired at this time showed significant new enhancing regions suspected as tumor progression, as shown in FIG. 6.

Figure 7:
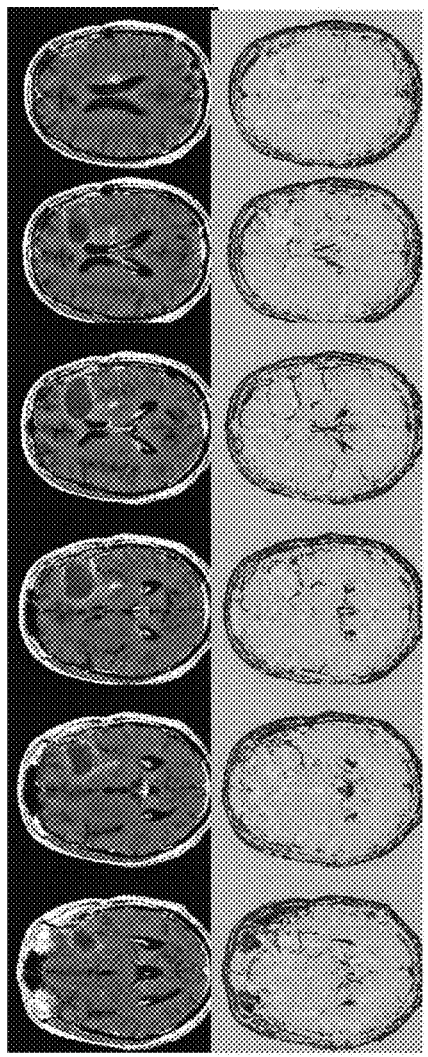
FIG. 7 is an MRI scan and mapping according to the present embodiments, of the patient of Example 2 four weeks post surgery.

Another two weeks later (4 weeks post surgery) the patient was scanned, as in FIG. 7, and the maps showed the surgery was successful, most of the tumor had been removed and the new enhancing regions were consistent with inflammation and not with tumor.

The patient has shown significant clinical improvement and continued TMZ and follow-up.

Example 3

Figure 8:
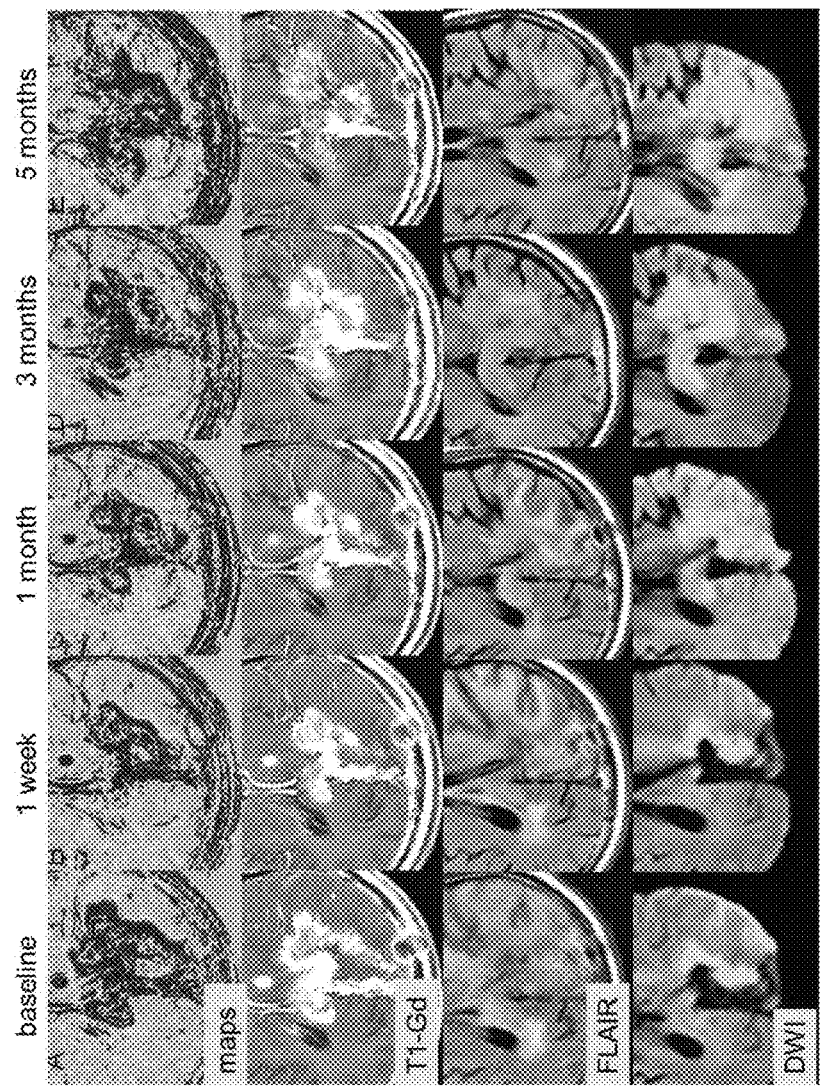
FIG. 8 shows MRI scans and mapping of the patient of Example 3 at successive time intervals.

Recurrent GBM: Referring now to FIG. 8, a 58 year old male with recurrent GBM was recruited 7 month after diagnosis prior to initiation of Bevacizumab treatment. At diagnosis the patients was operated on and received chemoradiation followed by TMZ. Six months later, at progression, the patient underwent a second resection and was recruited to the present Bevacizumab study 1 month after the second surgery, prior to initiation of the Bevacizumab treatment. At this point his enhancing lesion consisted of nearly 50% tumor according to the maps. Three months after initiation of Bevacizumab treatment conventional MRI showed improvement but the maps showed significantly larger blue/tumor volume, consistent with clinical deterioration. Following this scan the patient was treated with re-irradiation (in parallel with continuing Bevacizumab) and was stabilized. The next follow-up showed no significant change on conventional MRI but significant treatment response in the maps (a large percentage of the blue/tumor volume turned into red/non-tumor). The patient lived another ~7 months after this last MRI scan.

Example 4

GBM—Progression Vs Pseudoprogression: Examples of progression are characterized in the maps by increased blue/tumor volumes, and pseudoprogression is characterized in the maps by increased red volume with stable/decreased or slower increase in the blue/tumor volume. Two examples in GBM patients post chemoradiation are given in FIGS. 9A-F.

Referring now to FIGS. 9A-9F, in the first example (top row), the total enhancing volume has increased by 16% between 3 weeks (A) and 2.5 months (B) and then remained 17% above the initial volume (C) at 6.5 months post treatment. The blue volume slightly increased by 2% in the first 2.5 months (A, B) and then significantly increased to 57% above the initial volume at 6.5 months (C) while the red volume increased by 39% in the first 2.5 months (A, B) and decreased to 61% below the initial volume by 6.5 months (C). This patient progressed 6.5 months post treatment when he was referred to surgery. Histology showed ~70% of the lesion to consist of active tumor in agreement with the pre-surgical maps.

In the second example (bottom row of FIGS. 9A-9F), the total enhancing volume increased by 34% between 3 weeks (D) and 4.2 months (E) post chemoradiation, and then decreased to 33% below the initial volume (F) 9 months post treatment. The blue volume slightly increased by 6% in the first 4 months (D, E) and then significantly decreased to 47% below the initial volume at 9 months (F) while the red volume increased by 51% in the first 4.2 months (D, E) and decreased to 13% above the initial volume by 9 months (F). It was determined that the patient was experiencing pseudoprogression at 4.2 months. The patient progressed 11.6 months post treatment and was switched to Bevacizumab.

Example 5

Breast Cancer Brain Metastasis: Referring now to FIG. 10, a 49 year old female with a breast cancer brain metastasis was recruited 6 months post SRS with a small blue/tumor component. In the next follow-up, 3 months later, the blue component increased significantly. The patient was operated and histology showed active tumor in agreement with the pre-surgical maps. Maps calculated from the MRI acquired 1 month post surgery showed residual tumor surrounding the surgery site. At three months post surgery the blue volume had increased. The patient received radiation therapy and in the next follow-up, 3 months post radiation therapy, there was no residual blue/tumor component. The patient is stable and continuing follow-up.

Figure 11:
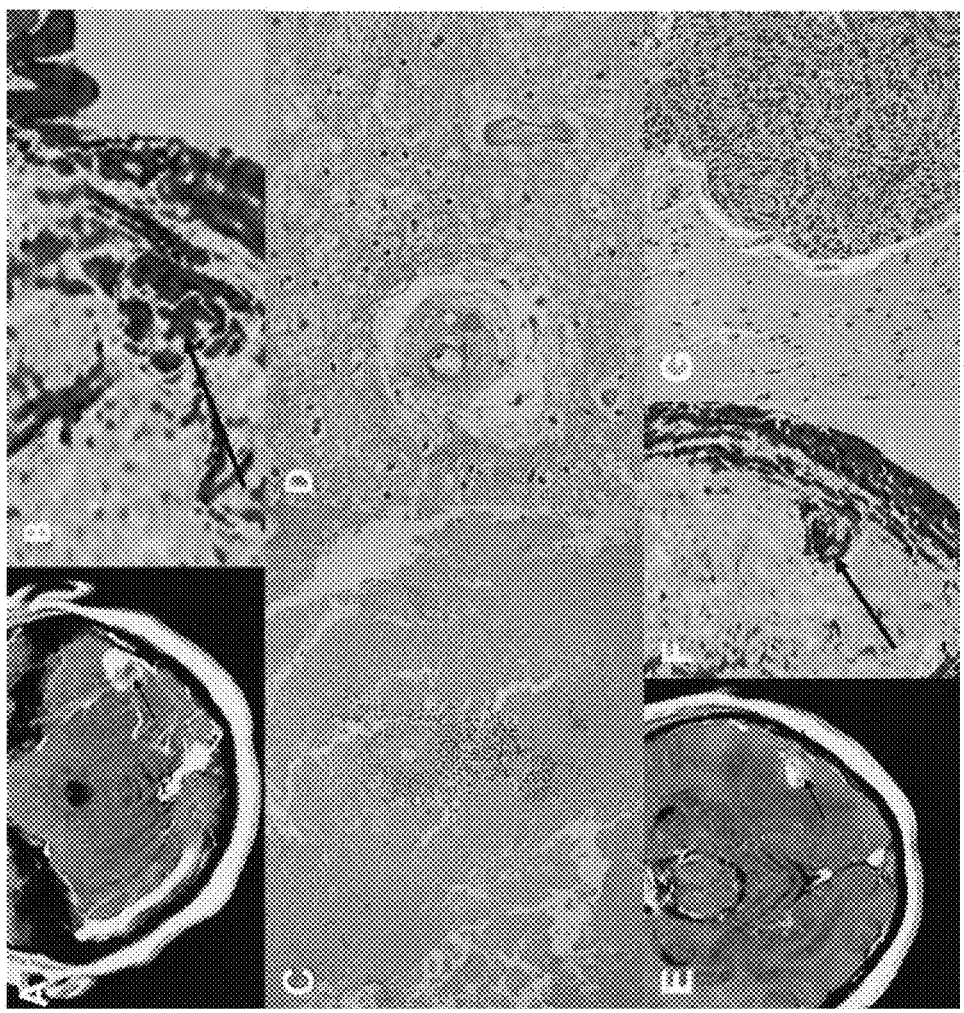
FIG. 11 illustrates histology for the patient in FIG. 10.

Comparison of the pre-surgical maps (B, F) with histology (C, D, G) for this patient is shown in FIG. 11. The sample taken from a red region marked by arrows in A and B shows a small tumor foci, surrounding a viable blood vessel, within a larger region of necrosis (C, magnification ×100). An example of necrotic blood vessels within the necrotic region (×400) is shown in D. Another sample, taken from a blue region on the border of normal brain marked by arrows in E and F, shows a highly cellular tumor adjacent to normal cortex (G, ×200).

Example 6

Figure 12:
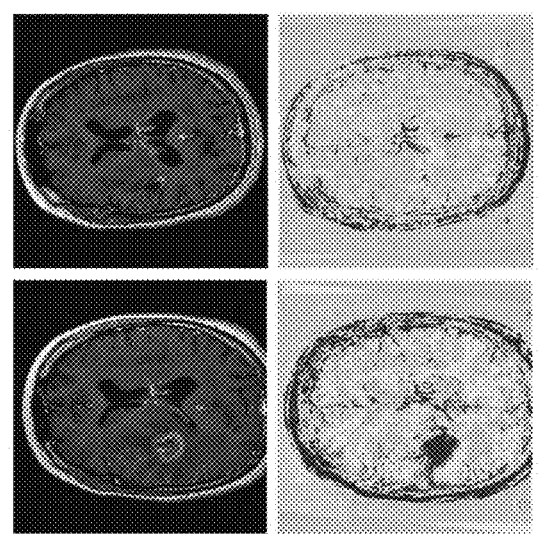
FIG. 12 illustrates MRI scans and mapping according to the present embodiments for melanoma brain metastasis and Example 6.

Melanoma brain metastasis: Referring to FIG. 12, a 57 years old female with a melanoma brain metastasis was recruited 4 months post SRS with an enhancing lesion showing red (reflecting radiation necrosis) in the maps. The patient has been followed for 13 months with no additional treatment. The lesion has nearly completely resolved.

Example 7

Figure 13:
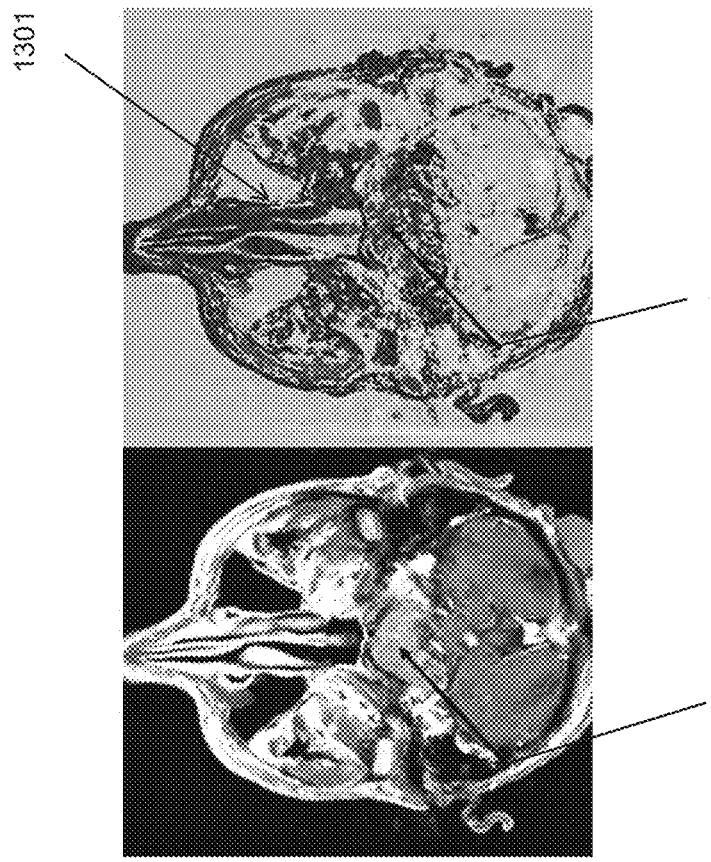
FIG. 13 illustrates an MRI scan and mapping of head and neck cancer according to example 7.

Reference is now made to FIG. 13 which shows an example of head and neck (extra cranial tumor) cancer, in which a patient with head and neck cancer ~1 year post chemoradiation was referred to the present inventors with a question of tumor progression versus treatment effects. The tumor is depicted in the maps (see reference 1301) as mainly blue, with no red component, suggesting tumor progression and not treatment effects. The patient died a few months later.

Using Different Delays and 3D Imaging Sequences:

The maps presented above were calculated from spin-echo T1-weighted MR images of 5 mm slices (with 0.5 mm gap between slices) acquired ~2 min after contrast injection and ~75 min (on average, range of 60-90 min after contrast injection) after contrast injection.

Since the contrast agent signal decays exponentially, we realized that the time of the delayed point can be flexible and the maps are not significantly changed when acquiring the late point at for example 90 min instead of 75 min post contrast.

The time of which the first images are acquired post contrast may have a larger effect on the resulting maps. For example, the signal of a lesion consisting of high concentration of normal blood vessels will increase fast after contrast injection (together with the increase of the blood due to the high concentration of the contrast agent) and will reach the maximal signal intensity within the first minute after contrast injection. Therefore, in order to obtain maximum sensitivity of the maps of the present embodiments to the change in signal intensity between the two data points it would be optimal to acquire the first data point soon after contrast injection. Since practically all our patients undergo DSC PWI during or immediately after contrast injection, the earliest we could acquire the first data point was ~2 min after contrast injection.

Still, in the case of brain tumors, there are additional factors affecting the time of the peak intensity. For example, a tumor consisting of certain BBB disruption patterns resulting in relatively slow accumulation of the contrast agent in the extracellular region, may reach the peak signal intensity of 5, 10 or even 15 min after contrast injection. In this case, it would be preferred to set the first time at some delay after contrast injection in order to maximize the difference in signal intensity between the two time points and thus increase the sensitivity to tumor tissues.

In the current study, we acquired our previously presented maps (using spin echo T1-weighted MRI with 5 mm slice thickness and 0.5 mm gap) with the first time point set at 2 min post contrast injection and the second point set at ~75 min (on average) post contrast. In addition, we have acquired additional sets of T1-weighted MR images using a 3D FSPGR MR sequences acquired 4-6 min post contrast injection (early point) and ~80 min post contrast injection (late point).

Using the 3D sequence provides increased sensitivity to the tumoral tissue due to the high spatial resolution (1 mm slice thickness instead of 5.5 mm) and thus increasing the sensitivity to small tumoral regions.

Figure 14:
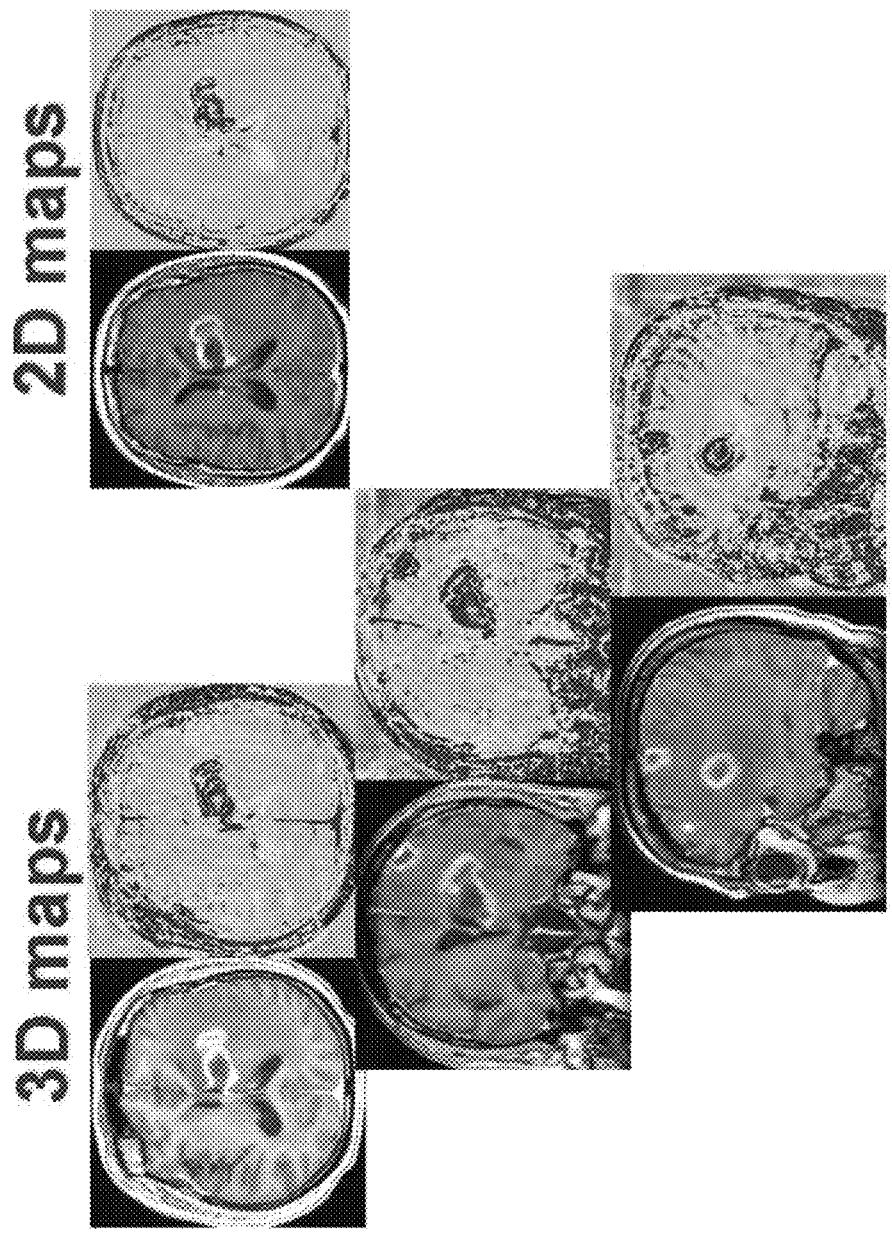
FIG. 14 shows two-dimensional and three-dimensional MRI scans and mapping according to the present embodiments of the patient of example 8 and showing three brain metastases of lung cancer.

In addition, in some tumors which reach the peak signal intensity later after the contrast injection, the 3D maps presented larger regions (i.e. increased sensitivity to tumoral regions) than those depicted in the regular maps. Examples are shown in FIG. 14, which is discussed in greater detail below.

As we generally use additional time points post contrast injection (between 2 min after contrast injection to 75 min post contrast injection) in order to obtain more information regarding the physiology of the tissues by studying the clearance/accumulation patterns of the contrast as a function of time, we may change the resolution of the 3D information in order to shorten the acquisition time at each point (for example reducing the resolution from 1 mm slices to 2 mm slices will cut down the acquisition time by nearly a factor of 2). This way we can still keep the 3D quality of the data but obtain more data points at relatively short acquisition times.

The Advantages of Using the 3D Maps:

The 3D maps enable a high resolution (pixels size of ~1 $mm^3$) depiction of tumor and non-tumoral tissues thus providing information regarding much smaller lesions and higher sensitivity to tumoral tissues than that obtained by the 2D maps. The 3D maps can also be used to obtain 3D views of the pathology thus assisting the physician in studying the pathology as well as plan high precision treatments.

The 3D maps are calculated from the 3D MRI data used for planning/performing precise procedures such biopsies, surgeries, focused radiation therapy, implantation of devices/shunts and more. The fact that the 3D maps of the present embodiments are of the same format, the same resolution and naturally registered to the conventional 3D data used in the neuronavigation/RT-planning workstations, makes their application for these procedures straightforward. Using the same tools they used before, the physicians can now target their treatment precisely at the tumoral tissue.

As illustrated in the examples, the 3D maps do not merely provide greater resolution, but actually allow the user to distinguish more effectively between tumor and treatment changes.

Data Acquisition Parameters for the 3D Data:

*3D T1-weighted FSPGR MR images were acquired on a 1.5 T Interventional Optima General Electric MR scanner with the following parameters: TE/TR=2.1/7.4, TI=400, Flip angle 20°, 1 acquisition, 1 mm slice thickness, BW=31 KHz, Matrix 256×256, 1 slab of 80 slices with a voxel size of 0.94×0.94×1 $mm^3$. Total acquisition time ~6 min. 5 min after injection and 80 min post injection.

*3D T1-weighted FSPGR MR images were acquired on a 3 T Signa HD XT General Electric MR scanner with the following parameters: TE/TR=3.1/7.54, TI=400, Flip angle 20°, 1 acquisition, 1 mm slice thickness, BW=31 KHz, Matrix 256×256, 1 slab of 80 slices with a voxel size of 0.94×0.94×1 $mm^3$. Total acquisition time ~6 min. 4 min after injection and 80 min post injection.

Example 8

Example 8 exemplifies use of 2D and 3D maps. Referring now to FIG. 14, a patient with 3 brain metastases of lung cancer was scanned by our 2D (D) and 3D (A-axial view, B-coronal view, C-sagittal view) maps. One can see the high sensitivity to the thin rim of active tumor (blue) provided by the 3D maps. The ability to view the lesions from different directions, obtained by the 3D information, makes it ideal for planning/performing high precision procedures.

Example 9

In an example of recurrent GBM post surgery, a 50 year old patient underwent subtotal gross tumor resection followed by chemoradiation and adjuvant Temozolomide. Three months after the resection, due to a recurrent tumor depicted in our maps the patient underwent a second resection. One month post surgery the maps showed no residual tumor. The maps presented in FIG. 15 were calculated from MR images acquired 3 months after the second resection showing the recurrent tumor surrounding the surgery site.

FIG. 15 shows 2D maps acquired 1 month and 3 months after the second resection showing that most of the blue/tumor tissue has been removed (1 month post surgery) but recurrence was observed 3 months post surgery.

FIG. 16 shows 2D (left) and 3D (right) maps acquired 3 months after the second resection showing recurrent tumor. It can be seen that the 3D maps (slice resolution 1 mm, $1^{st}$ time point acquired 5 min post contrast injection) show larger regions of recurrent tumor surrounding the surgery site, arrows) than the 2D maps (slice resolution 5.5 mm, 1$^{st}$ time point acquired 2 min post contrast injection). In addition, it is possible to see a small distant tumoral region (adjacent to the ventricle, arrow) which could not be detected in the 2D maps due to its small dimensions but is depicted in the 3D maps.

Example 10

Referring now to FIG. 17, a patient with a brain metastasis of ovarian cancer was scanned by both 2D (top) and 3D (bottom) maps. In this case the 3D maps present higher resolution but the overall tumor volume seen in the two types of maps is similar.

Example 11

This Example demonstrate the ability of the present embodiments to differentiate open arteriovenous malformation (AVM) from closed AVM and from treatment effects.

Nine patients with AVM were recruited. Examples of three treated lesions are shown in FIGS. 18A-I. Blood vessels appear blue in the maps and treatment effects such as radiation necrosis appear red. FIGS. 18A-C (top row) show contrast-enhanced T1-weighted MRI, FIGS. 18D-F (middle row) show the calculated maps, and FIGS. 18G-I (bottom row) show rCBV maps.

FIGS. 18A-I demonstrate patients with arteriovenous malformation, 3.5 years after 5 embolization treatments (FIGS. 18A, 18D, 18G), 2 weeks after stereotactic radiosurgery (FIGS. 18B, 18E, 18H) and 3 years after embolization and fractional stereotactic radiosurgery (FIGS. 18C, 18F, 18I).

Blue regions in the maps thus represent open AVM regions. FIGS. 18A-I shows an example of a closed AVM (left column) an open AVM (middle column) and a partially open AVM with radiation necrosis (right column).

Other vascular disorders can be analyzed using the same or similar techniques. For example, the technique allows depiction of cavernoma within a bleeding region.

Example 12

This example demonstrates the ability of the present embodiments to differentiate tumor from treatment effects, in cases of rare tumors.

An 8 years old boy was recruited with an anaplastic chordoma, previously treated by stereotactic radiosurgery and now showing increased enhancement suspected for radiation necrosis. FIG. 19 shows the obtained MRI (top row) and the constructed maps (bottom row). The maps show significant portion of active tumor. The boy was referred to surgery.

A 63 years old patient recruited 1 year after stereotactic radiosurgery of a chordoma with suspected radiation necrosis. FIG. 20A shows the obtained MRI and FIG. 20B shows the constructed map. The map shows radiation necrosis.

A patient was recruited 3 years after stereotactic surgery treatment of anaplastic meningioma with a question of tumor versus treatment effects. FIG. 21A shows the obtained MRI and FIG. 21B shows the constructed map. The map show significant component of active tumor and the patient was resected.

Figure 22A:
Figure 22B:
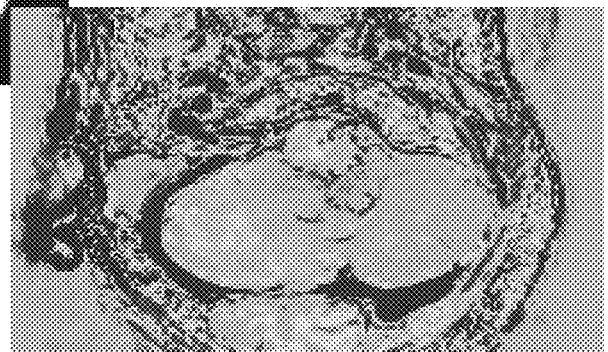
Figure 22C:
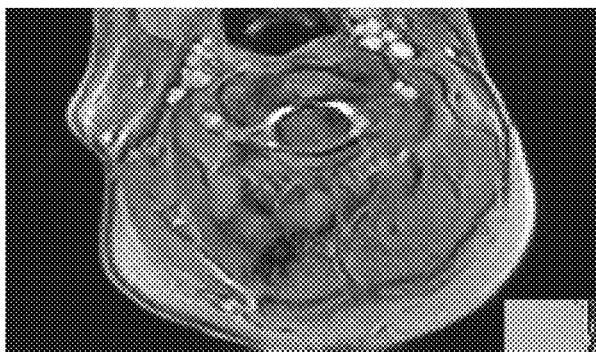
Figure 22D:
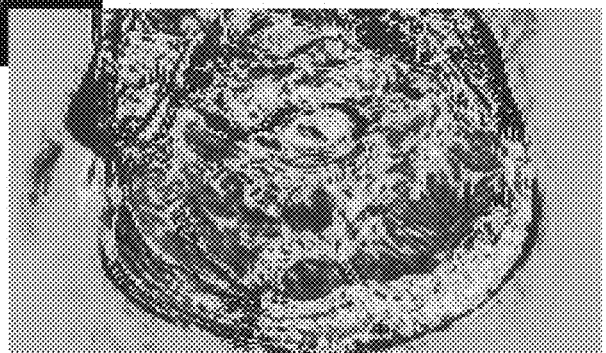

A patient previously diagnosed with a low grade non-enhancing glioma in the brain stem and spine, recruited to the study with new enhancements in the spine suspected for radiation necrosis. FIGS. 22A and 22C show the obtained MRI and FIGS. 22B and 22D show the constructed maps. One lesion was determined by the maps to be active tumor (FIG. 22B) while the other was determined to be treatment effects (FIG. 22D).

A patient was recruited 1 month after surgical removal of a hypofisal adenoma with a question of residual tumor post surgery. FIG. 23A shows the obtained MRI and FIG. 23B shows the constructed map. The map allows determining the existence of residual tumor.

A patient with petroclival meningioma was recruited 6 years post SRS with a question of tumor versus radiation necrosis. FIG. 24A shows the obtained MRI and FIG. 24B shows the constructed map. The map shows significant volumes of active tumor.

Example 13

This example demonstrate the application of the maps of the present embodiments for animals. FIG. 25A shows MRI obtained from rats with CNS1 glioma, and FIG. 25B shows the respective constructed map. FIGS. 26B and 26D show MRI obtained from dogs with spontaneous glioma, and FIGS. 26A and 26C show the respective constructed maps. FIG. 27A shows MRI obtained from nude mice with U87 (human) glioma, and FIG. 27B shows the respective constructed map.

Example 14

This example demonstrates the ability of the maps of the present embodiments to detect active tumor within bleeding regions.

A patient with malignant melanoma was recruited after diagnosis of a bleeding lesion in the brain stem with a question of existence of active tumor within the bleeding region.

FIG. 28A shows MRI (top row) and constructed maps (bottom row) obtained before treatment, and FIG. 28B shows MRI (top row) and constructed maps (bottom row) obtained four months after treatment by radiation. The maps show significant tumor volume within the bleeding prior to treatment and four months following treatment the tumor volume decreased significantly.

Example 15

This example demonstrates the ability of the maps of the present embodiments to monitor the response of breast cancer brain metastases to Avastin. In addition, this example demonstrates the advantage of the maps over conventional MRI in studying the action of the drug. There is current dispute weather Avastin affects active tumor or only treatment effects. The current example demonstrates the ability of the maps to show that the drug had direct effect on the tumor component and not only on the treatment effects component.

A patient with cerebellar metastasis of breast cancer was recruited 2 years after stereotactic radiosurgery with suspected radiation necrosis. FIG. 29A shows MRI (top row) and constructed maps (bottom row) obtained before treatment, and FIG. 29B shows MRI (top row) and constructed maps (bottom row) obtained after treatment with Avastin.

The maps showed significant tumor and radiation necrosis before treatment, and remarkable response of both components following treatment.

Example 16

This example demonstrates the ability of the maps of the present embodiments to monitor the response of GBM to Avastin.

A patient with GBM was recruited after 2 resections and treatment with chemoradiation.

FIG. 30A shows MRI (top row) and constructed maps (bottom row) obtained before treatment, and FIG. 30B shows MRI (top row) and constructed maps (bottom row) obtained after treatment. The maps show both the tumor and the treatment-effects components.

Example 17

Histological evaluations of 51 lesions resected from 47 patients were compared with the pre-surgical maps. In addition, 7 of the lesions were resected en-block and 62 biopsied samples were obtained from 21 of the patients. Histological data of 29 lesions obtained from 12 patients with primary brain tumors and 15 patients with metastatic brain tumors are listed in Table 1. Histological evaluation consisted of blinded pathological reports, focused mainly on the existence/absence of active tumor in all the material examined by the pathologist, and non-blinded histological evaluation of the biopsies and en-block samples.

Taking into account the blinded radiological reports, complete agreement between the pre-surgical maps of the present embodiments and histology was found in 47 of 51 resected lesions suggesting sensitivity and positive predictive value (PPV) to active tumor of 100% and 92% respectively. Adding the non-blinded data of 62 biopsied samples and 7 en-block samples, resulted in sensitivity and PPV of 99% and 95% respectively. Disagreement between the maps of the present embodiments and histology were found in 4 cases. In 3 cases of brain metastases, the pre-surgical maps showed ~85% red and ~15% blue while no tumor was found in histology. Still, a blue rim surrounding the surgery site appeared 1-4 months post-surgery in all 3 patients suggesting residual/recurrent tumor. The fourth case was of GBM patient who underwent gross total resection 4 months prior to recruitment followed by one course of radiation and one course of TMZ. In this case the maps of the present embodiments showed a blue/tumor volume of 3.3 ml at recruitment and of 12.8 ml months later, prior to surgery. Despite the rapid growth in blue/tumor volume, histology determined the tumor to be quiescent.

TABLE 1

List of biopsied and whole samples, maps characteristics and histological evaluation

| Sample # | Lesion # | Patient # | map characteristics | Histological description | Clinical diagnosis |
|---|---|---|---|---|---|
| 1 | 1 | 1 | Sample taken from medial blue region | Cellular tumor with dilated blood vessels with thick walls | AA post chemoradiation |
| 2 | 1 | 1 | Sample taken from lateral blue region | Cellular tumor | AA post chemoradiation |
| 3 | 1 | 1 | Sample taken from periventricular blue region | Cellular tumor with dilated blood vessels | AA post chemoradiation |
| 4 | 1 | 1 | Sample taken from central red region | Mostly radiation necrosis with reactive astrocytes. There are small regions with non-active tumor | AA post chemoradiation |
| 1 | 2 | 2 | Sample taken from lower blue region | Highly cellular active tumor | GBM post chemoradiation |
| 2 | 2 | 2 | Sample taken from higher blue region | Highly cellular active tumor | GBM post chemoradiation |
| 1 | 3 | 3 | Sample taken from light blue region adjacent to the periphery of the tumor | atypical cells and proliferating blood vessels in the infiltrating zone | GBM post chemoradiation |
| 2 | 3 | 3 | Sample taken from blue region in the deep frontal region of the tumor mass | highly cellular and highly vascularized tumor and cellular atypia | GBM post chemoradiation |
| 3 | 3 | 3 | Sample taken from central red region on the border of a blue region | a large necrotic region bordered by a highly vascularized tumor | GBM post chemoradiation |

TABLE 1-continued

List of biopsied and whole samples, maps characteristics and histological evaluation

| Sample # | Lesion # | Patient # | map characteristics | Histological description | Clinical diagnosis |
|---|---|---|---|---|---|
| 4 | 3 | 3 | Sample taken on the border between a blue region and adjacent light blue region in surrounding brain | active tumor and abnormal vessels in the peripheral/ infiltrating region | GBM post chemoradiation |
| 5 | 3 | 3 | Sample taken from light blue region surrounding the tumor and adjacent to the ventricles | normal brain and infiltrating zone with abnormal blood vessels | GBM post chemoradiation |
| 6 | 3 | 3 | Sample taken en-block from a region showing a red center surrounded by a thick blue rim | En-block sample: Central necrotic region surrounded by highly cellular and highly vascularized rim of tumor | GBM post chemoradiation |
| 1 | 4 | 4 | Sample taken from lower blue region | Active tumor showing hypercellularity, cellular atypia and mitoses | GBM post chemoradiation |
| 2 | 4 | 4 | Sample taken from anterior blue region | Active tumor showing hypercellularity, cellular atypia and mitoses | GBM post chemoradiation |
| 3 | 4 | 4 | Sample taken from superior blue region | Active tumor showing hypercellularity with cellular atypia, mitoses, vascular proliferation and pseudopalisading necrosis | GBM post chemoradiation |
| 4 | 4 | 4 | Sample from posterior blue region | Active tumor showing hypercellularity, cellular atypia and mitoses | GBM post chemoradiation |
| 1 | 5 | 5 | Sample taken from blue peripheral region | Highly cellular active tumor | Malignant melanoma brain metastasis |
| 2 | 5 | 5 | Sample taken from central red/green region adjacent to surrounding blue region | Necrosis and hemorrhages on the border of the tumor region | Malignant melanoma brain metastasis |
| 1 | 6 | 6 | Sample taken from blue peripheral region reaching the dura | Active tumor adjacent to the dura | Malignant melanoma brain metastasis |
| 2 | 6 | 6 | Sample taken from a blue region within the main tumor mass | Active tumor with dilated blood vessels | Malignant melanoma brain metastasis |
| 3 | 6 | 6 | Sample taken from a blue region at the medial peripheral region of the tumor mass | Active tumor with dilated blood vessels | Malignant melanoma brain metastasis |
| 1 | 7 | 7 | Sample taken from frontal blue region | Active tumor with small regions of necrosis | GBM post chemoradiation |

TABLE 1-continued

List of biopsied and whole samples, maps characteristics and histological evaluation

| Sample # | Lesion # | Patient # | map characteristics | Histological description | Clinical diagnosis |
|---|---|---|---|---|---|
| 2 | 7 | 7 | Sample taken from frontal red region | necrosis | GBM post chemoradiation |
| 3 | 7 | 7 | Sample taken from posterior red region | necrosis | GBM post chemoradiation |
| 4 | 7 | 7 | Sample taken from lower region of mixed red/blue | Necrosis with regions of active tumor | GBM post chemoradiation |
| 1 | 8 | 8 | Sample taken from peripheral blue region | Active lymphoma tumor | Diffuse large B cell lymphoma |
| 1 | 9 | 9 | Sample taken from lateral blue region | Highly cellular tumor with multiple foci of palicadig necrosis | GBM post Avastin |
| 2 | 9 | 9 | Sample taken from lateral blue region | Highly cellular tumor with multiple foci of palicadig necrosis | |
| 3 | 9 | 9 | Sample taken from red region within a larger blue region | Scattered pieces of tissue with one region of necrosis and the rest tumor | |
| 4 | 9 | 9 | Sample taken from central blue region | Highly cellular tumor with mitosis and palicading necrosis | |
| 1 | 10 | 10 | Non-biopsied lesion: Mixed regions of blue and red surrounding the previous surgery site | Active tumor is represented by moderately cellular areas with numerous gemistocytes showing palisading necrosis. Mitoses are not detected but ki67 is positive in numerous small clusters of cells within the areas showing palisading necrosis. A proliferation of up to 8-10% of the cells is seen in these clusters. Radiation necrosis and changes are also present | GBM post chemoradiation |
| 1 | 11 | 11 | Non-biopsied lesion: Mixed blue/red regions | Glioblastoma showing vascular proliferation and tumor necrosis | GBM post Avastin |
| 1 | 12 | 12 | Non-biopsied lesion: Mostly blue regions surrounding the previous surgery site | Anaplastic oligodendroglioma. WHO grade III. The tumor shows brisk mitotic activity, vascular proliferation and necrosis | Anaplastic oligodendroglioma. |
| 1 | 13 | 13 | Non-biopsied lesion: Red lesion surrounded by a thin blue rim (16% of the lesion volume) | Pure radiation necrosis | Breast cancer brain metastasis |
| 1 | 14 | 14 | Non-biopsied lesion: lesion consisting of 24% blue regions | Lesion consisting radiation necrosis and ~15% active tumor | Breast cancer brain metastasis |

TABLE 1-continued

List of biopsied and whole samples, maps characteristics and histological evaluation

| Sample # | Lesion # | Patient # | map characteristics | Histological description | Clinical diagnosis |
|---|---|---|---|---|---|
| 1 | 15 | 15 (1st operation) | Non-biopsied lesion: Lesion consisting of 46% blue regions | Lesion consisting of ~50% active tumor and ~50% radiation necrosis | Breast cancer brain metastasis |
| 1 | 16 | 15 (2nd operation) | Non-biopsied lesion: lesion showing red with thin blue rim | Active tumor was found | Breast cancer brain metastasis |
| 1 | 17 | 16 | Non-biopsied lesion: Lesion with central red core surrounded by a thick blue rim | Central necrosis surrounded by active tumor | Non Small Cell Lung Cancer brain metastasis Lesion resected en-block |
| 1 | 18 | 17 | Non-biopsied lesion: Red lesion surrounded by a thin blue rim (16% of the lesion volume) | Pure RN | Non Small Cell Lung Cancer brain metastasis |
| 1 | 19 | 18 (1st operatopm) | Non-biopsied lesion: Blue lesion with a red center | Metastatic squamous cell carcinoma | Non Small Cell Lung Cancer brain metastasis Lesion resected en-block |
| 1 | 20 | 18 (2nd operation) | Non-biopsied lesion: Lesion within previous surgery site, mostly blue | Squamous cell carcinoma from lung with less differentiations and spindling than in the previous surgery | Non Small Cell Lung Cancer brain metastasis Lesion resected en-block |
| 1 | 21 | 19 | Non-biopsied lesion: Mostly blue lesion | Adeno carcinoma is present | Adeno carcinoma of unknown source |
| 1 | 22 | 20 | Non-biopsied lesion: Large lesion, mixed blue, red, green | Papillary tumor, radiation necrosis and hemorrhages are present | Non Small Cell Lung Cancer brain metastasis |
| 1 | 23 | 21 | Non-biopsied lesion: Mostly blue lesion | Metastatic carcinoma is present | Non Small Cell Lung Cancer brain metastasis |
| 1 | 24 | 22 | Non-biopsied lesion: Mostly blue lesion | Active tumor is present, with regions of dilated tumor vessels and hemorrhages within the tumor with adjacent normal brain | Malignant melanoma brain metastasis Lesion resected en-block |
| 1 | 25 | 23 | Non-biopsied lesion: Red lesion with thin blue rim (16% of the lesion volume) | Mainly brain fragments with reactive changes and some fragments of pure radiation necrosis | Non Small Cell Lung Cancer brain metastasis |
| 1 | 26 | 24 | Non-biopsied lesion: Blue lesion extending to a red lesion surrounded by a thin blue rim | Active tumor is present | Non Small Cell Lung Cancer brain metastasis Lesion resected en-block |
| 1 | 27 | 25 | Non-biopsied lesion: Red lesion with a thin blue rim | Active tumor is present | Yolk Sac Carcinoma brain metastasis Lesion resected en-block |
| 1 | 28 | 26 | Non-biopsied lesion: Lesion consisting of a red rim surrounded by a blue rim | Meningioma with necrotic area. Atypical meningioma WHO grade II. EMA positive. Ki67 positive in ~25% of the cells. CD34 focally positive. BC12 and PR negative. | Atypical meningioma |

TABLE 1-continued

List of biopsied and whole samples, maps characteristics and histological evaluation

| Sample # | Lesion # | Patient # | map characteristics | Histological description | Clinical diagnosis |
|---|---|---|---|---|---|
| 1 | 29 | 27 | Non-biopsied lesion: Mostly blue mass surrounding previous surgery site | Quiescent tumor with very little regions of RN. Hypercellularity due to the presence of histiocytes and hyperplasia of microglia and scattered non-proliferating small cells of uncertain identity. In addition, large radiated tumor astrocytes. | GBM post chemoradiation |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. Apparatus for operating MRI, comprising:
a control for operating an MRI scanner to carry out an MRI scan of an organ of a subject;
an input for receiving first and second MRI scans respectively at the beginning and end of a predetermined time interval post contrast administration, wherein said beginning of said predetermined time interval is at least three minutes and no more than twenty minutes post contrast administration, and wherein said end of said predetermined time interval is at least twenty minutes after said beginning of said predetermined time interval;
an image processor having a circuit configured for forming a subtraction map from said first and said second MRI scans by analyzing said scans to distinguish between two primary populations, a slow population, in which contrast clearance from the tissue is slower than contrast accumulation, and a fast population in which clearance is faster than accumulation;
a registration unit having a circuit for carrying out registration between corresponding MRI images; and
a smoothing and interpolation unit having a circuit for smoothing a translation matrix resulting from said registration using circular smearing, and interpolating to obtain translation values per pixel; and
an output converting said scans to a displayed subtraction map on which distributions of said two primary populations are distinguished, wherein a distribution of said fast population corresponds to a tumoral tissue region and a distribution of said slow population corresponds to a non-tumoral tissue region;
wherein said control is configured to carry out said first scan at said beginning of said predetermined time interval, and to carry out said second scan at said end of said predetermined time interval.

2. The apparatus according to claim 1, wherein said registration comprises a rigid body registration.

3. The apparatus according to claim 1, wherein said registration comprises an elastic registration to allow for head movements and resulting distortions between respective scans.

4. Apparatus for operating MRI, comprising:
an MRI Scanner configured for performing an MRI scan using a 3D MRI pulse sequence;
an input for receiving first and second MRI scans of an organ of a subject respectively at the beginning and end of a predetermined time interval post contrast administration from said MRI scanner;
an image processor having a circuit configured for forming a subtraction map from said first and said second MRI scans by analyzing said scans to distinguish between two primary populations, a slow population, in which contrast clearance from the tissue is slower than contrast accumulation, and a fast population in which clearance is faster than accumulation;
a registration unit having a circuit for carrying out registration between corresponding MRI images; and
a smoothing and interpolation unit having a circuit for smoothing a translation matrix resulting from said registration using circular smearing, and interpolating to obtain translation values per pixel; and
an output converting said scans to a displayed subtraction map on which distributions of said two primary populations are distinguished, wherein a distribution of said fast population corresponds to a tumoral tissue region and a distribution of said slow population corresponds to a non-tumoral tissue region;

wherein said control is configured to carry out said first scan and said second scan such that said predetermined time interval is at least twenty minutes.

5. The apparatus of claim 4, wherein said circuit of said image processor is configured for constructing, for each magnetic resonance image, an intensity map, wherein the subtraction map describes variations in concentration of the contrast agent in said organ by detecting dissimilarities among a pair of intensity maps.

6. The apparatus according to claim 4, wherein said predetermined time interval is any one of the group consisting of: more than twenty minutes, more than thirty minutes, more than forty minutes, more than fifty minutes, more than sixty minutes, more than seventy minutes, more than eighty minutes, more than ninety minutes, more than a hundred minutes, seventy minutes, seventy five minutes and ninety minutes.

7. The apparatus according to claim 4, wherein said circuit of said image processor is configured for assigning a representative intensity value for a selected ROI in each magnetic resonance image and determining a time-dependence of said representative intensity value.

8. The apparatus according to claim 4, wherein said tumor is a morphologically active tumor.

9. The apparatus according to claim 4, wherein said input receives from said MRI scanner at least one additional MRI scans before said first MRI scan, said MRI scans being acquired post contrast administration, and wherein said circuit of said image processor is configured for forming a first subtraction map using said additional MRI scan and said second MRI scan, and a second subtraction map using said first MRI scan and said second MRI scan.

10. The apparatus according to claim 9, wherein said circuit of said image processor is configured for identifying said slow population using said first map, and for identifying said fast population using said second map.

11. The apparatus according to claim 10, wherein said circuit of said image processor is configured for forming a third map having regions corresponding to said slow population as obtained from said first map, and regions corresponding to said fast population as obtained from said second map.

12. The apparatus according to claim 9, wherein said circuit of said image processor is configured for identifying said slow population using said first map but not said second map, and for identifying said fast population using said second map but not said first map.

13. The apparatus according to claim 4, wherein said slow population corresponds to an abnormal but non-tumoral tissue region.

14. The apparatus according to claim 13, wherein said abnormal but non-tumoral tissue region corresponds to at least one of a treatment effect, an inflammation, and BBB disruption.

15. The apparatus according to claim 4, further configured to carry out image pre-processing.

16. The apparatus according to claim 15, wherein said preprocessing comprises correction for intensity variations.

17. The apparatus of claim 15, wherein said correction for intensity variations comprises calculating, for each MRI image separately, an intensity variation map consisting of large scale intensity variations therein and then subtracting said intensity variation map from the respective image.

18. The apparatus according to claim 4, further comprising a data processor configured for estimating a progression time of a tumor, based on initial growth rate in said fast population.

19. The apparatus according to claim 4, in use for depiction of residual tumor post surgery.

20. The apparatus according to claim 4, in use for analysis of extra-cranial tumors.

21. The apparatus of claim 4, wherein said 3D MRI pulse sequence comprises fast spoiled prepared gradient echo.

22. Method for analyzing MRI of an organ of a subject, comprising:
operating an MRI scanner to generate a first and a second MRI scan respectively at the beginning and end of a predetermined time interval post contrast administration, wherein the beginning of said predetermined time interval is at least five minutes and no more than ten minutes post contrast injection, and wherein the end of said predetermined time interval is at least twenty minutes after the beginning of said predetermined time interval;
forming, by an image processor, a subtraction map from said first and said second MRI scans by analyzing said scans to distinguish between two primary populations, a slow population, in which contrast clearance from the tissue is slower than contrast accumulation, and a fast population in which clearance is faster than accumulation;
applying registration between corresponding MRI images, smoothing a translation matrix resulting from said registration using circular smearing, and interpolating to obtain translation values per pixel; and
converting said scans to a displayed subtraction map on which distributions of said two primary populations are distinguished wherein a distribution of said fast population is corresponds to a tumoral tissue region and a distribution of said slow population corresponds to a non-tumoral tissue region.

23. The method of claim 22, wherein said forming comprises constructing, for each magnetic resonance image, an intensity map, wherein said subtraction map describes variations in concentration of the contrast agent in said organ by detecting dissimilarities among a pair of intensity maps.

24. The method of claim 23, further comprising using said map to distinguish between residual tumor post-surgery and post-surgical changes.

25. The method according to claim 22, wherein said predetermined time interval is any one of the group consisting of: more than twenty minutes, more than thirty minutes, more than forty minutes, more than fifty minutes, more than sixty minutes, more than seventy minutes, more than eighty minutes, more than ninety minutes, more than a hundred minutes, seventy minutes, seventy five minutes and ninety minutes.

26. The method according to claim 22, further comprising determining, from said subtraction map, whether tumor tissue is present, by comparing drainage of the contrast agent from blood vessels with contrast agent take up in the tissue.

27. The method of claim 22, further comprising using said subtraction map for analysis of extra-cranial tumors.

28. Method for analyzing MRI of an organ of a subject, comprising:
operating an MRI scanner to generate a first MRI scan and a second MRI scan at the beginning and end of a predetermined time interval post contrast administration, wherein said operating comprises applying a 3D MRI pulse sequence;
forming, by an image processor, a subtraction map from said first and said second MRI scans by analyzing said scans to distinguish between two primary populations, a slow population, in which contrast clearance from the tissue is slower than contrast accumulation, and a fast population in which clearance is faster than accumulation; and converting said scans to a displayed subtraction map on which distributions of said two primary populations are distinguished, wherein a distribution of said fast population corresponds to a tumoral tissue region and a distribution of said slow population corresponds to a non-tumoral tissue region;

wherein said predetermined time interval is at least twenty minutes.

29. The method according to claim 28, comprising depiction of tumors in said organ after treatment with chemotherapy and/or radiation-based treatments, for differentiation between tumor progression and pseudoprogression.

30. The method of claim 28, wherein said 3D MRI pulse sequence comprises fast spoiled prepared gradient echo.

31. The method of claim 28, further comprising using said subtraction map for analysis of extra-cranial tumors.

32. Apparatus for operating MRI, comprising:
a control for operating an MRI scanner to carry out an MRI scan of an organ of a subject;
an input for receiving first and second MRI scans respectively at the beginning and end of a predetermined time interval post contrast administration, wherein said beginning of said predetermined time interval is at least three minutes and no more than twenty minutes post contrast administration, and wherein said end of said predetermined time interval is at least twenty minutes after said beginning of said predetermined time interval;
an image processor having a circuit configured for forming a subtraction map from said first and said second MRI scans by analyzing said scans to distinguish between two primary populations, a slow population, in which contrast clearance from the tissue is slower than contrast accumulation, and a fast population in which clearance is faster than accumulation; and
an output converting said scans to a displayed subtraction map on which distributions of said two primary populations are distinguished, wherein a distribution of said fast population corresponds to a tumoral tissue region and a distribution of said slow population corresponds to a non-tumoral tissue region;
wherein said control is configured to carry out said first scan at said beginning of said predetermined time interval, and to carry out said second scan at said end of said predetermined time interval;
the apparatus being used for analysis of extra-cranial tumors.

33. Apparatus for operating MRI, comprising:
an MRI Scanner configured for performing an MRI scan using a 3D MRI pulse sequence;
an input for receiving first and second MRI scans of an organ of a subject respectively at the beginning and end of a predetermined time interval post contrast administration from said MRI scanner;
an image processor having a circuit configured for forming a subtraction map from said first and said second MRI scans by analyzing said scans to distinguish between two primary populations, a slow population, in which contrast clearance from the tissue is slower than contrast accumulation, and a fast population in which clearance is faster than accumulation; and
an output converting said scans to a displayed subtraction map on which distributions of said two primary populations are distinguished, wherein a distribution of said fast population corresponds to a tumoral tissue region and a distribution of said slow population corresponds to a non-tumoral tissue region;
wherein said control is configured to carry out said first scan and said second scan such that said predetermined time interval is at least twenty minutes;
the apparatus being used for analysis of extra-cranial tumors.

\* \* \* \* \*